United States Patent
Crew et al.

(10) Patent No.: US 7,659,274 B2
(45) Date of Patent: Feb. 9, 2010

(54) UNSATURATED MTOR INHIBITORS

(75) Inventors: Andrew Philip Crew, Farmingdale, NY (US); Douglas S. Werner, Farmingdale, NY (US); Paula A. R. Tavares, Farmingdale, NY (US)

(73) Assignee: OSI Pharmaceuticals, Inc., Melville, NY (US)

( * ) Notice: Subject to any disclaimer, the term of this patent is extended or adjusted under 35 U.S.C. 154(b) by 275 days.

(21) Appl. No.: 11/657,156

(22) Filed: Jan. 24, 2007

(65) Prior Publication Data

US 2007/0254883 A1 Nov. 1, 2007

Related U.S. Application Data

(60) Provisional application No. 60/762,076, filed on Jan. 25, 2006.

(51) Int. Cl.
*A61K 31/4985* (2006.01)
(52) U.S. Cl. .............. 514/249; 544/350; 546/199; 549/59
(58) Field of Classification Search ............ 544/350
See application file for complete search history.

(56) References Cited

U.S. PATENT DOCUMENTS

| | | | |
|---|---|---|---|
| 5,869,485 A | 2/1999 | Missbach | |
| 6,001,839 A | 12/1999 | Calderwood et al. | |
| 2002/0156081 A1 | 10/2002 | Hirst et al. | |
| 2003/0073218 A1 | 4/2003 | Shokat et al. | |
| 2003/0187001 A1 | 10/2003 | Calderwood et al. | |
| 2005/0004142 A1 | 1/2005 | Adams et al. | |
| 2005/0130994 A1 | 6/2005 | Chen et al. | |
| 2006/0019957 A1 | 1/2006 | Crew et al. | |
| 2006/0084654 A1 | 4/2006 | Beck et al. | |
| 2006/0235031 A1 | 10/2006 | Arnold et al. | |
| 2007/0112005 A1 | 5/2007 | Chen et al. | |
| 2007/0149521 A1 | 6/2007 | Crew et al. | |
| 2007/0167383 A1 | 7/2007 | Roberts et al. | |
| 2007/0203143 A1 | 8/2007 | Sheppard et al. | |
| 2007/0280928 A1 | 12/2007 | Buck et al. | |
| 2007/0293516 A1 | 12/2007 | Knight et al. | |
| 2008/0032960 A1 | 2/2008 | Knight et al. | |
| 2009/0099174 A1 | 4/2009 | Smith | |
| 2009/0124638 A1 | 5/2009 | Shokat et al. | |

FOREIGN PATENT DOCUMENTS

| | | |
|---|---|---|
| WO | 2007115620 | 10/2007 |
| WO | 2007126841 | 11/2007 |

OTHER PUBLICATIONS

Bergstrom, D. et al. (1981) Journal of Organic Chemistry 46(7):1423-1431.
Bergstrom, D. et al. (1991) Journal of Organic Chemistry 56(19):5598-5602.
Bishop, A. et al. (1999) Journal of the American Chemical Society 121(4):627631.
Buzko, O. et al. (2002) Journal of Computer-Aided Design 16(2):113-127.
Hubbard, R.D. et al. (2007) Bioorganic & Medicinal Chemistry Letters 17(19):5406-5409.
International Preliminary Report on Patentability in PCT/US2006/044461.
International Search Report in PCT/US2006/044461.
International Search Report in PCT/US2007/002027.
Kinkade, C.W. et al. (2008) Journal of Clinical Investigation 118(9):3051-3064.
Legrier, M. et al. (2007) Cancer Research 67(23):11300-11308.
Papadimitrakopoulou, V. and Adjei, A.A. (2006) Journal of Thoracic Oncology 1(7): 749-751.
Prousek, J. (1984) Collection of Czechoslovak Chemical Communications 49(8):1788-1794.
Raslan, M.A. et al. (2000) Heteroatom Chemistry 11(2):94-201.
Seela, F. et al. (2000) Helvetica Chimica Acta 83(5):910-927.
Schram, K. et al. (1974) Journal of Carbohydrates, Nucleosides, Nucleotides 1(1):39-54.
Written Opinion of the International Search Authority in PCT/US2006/044461.
Written Opinion of the International Search Authority in PCT/US2007/002027.

*Primary Examiner*—James O Wilson
*Assistant Examiner*—Brian McDowell

(57) ABSTRACT

Compounds represented by Formula (I)

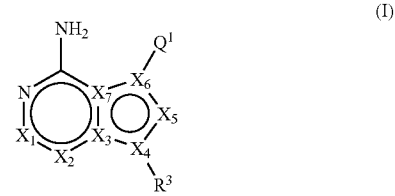

or a pharmaceutically acceptable salt thereof, are inhibitors of mTOR and useful in the treatment of cancer.

3 Claims, No Drawings

UNSATURATED MTOR INHIBITORS

This application claims the benefit of U.S. Patent Application No. 60/762,076, filed Jan. 25, 2006.

BACKGROUND OF THE INVENTION

The present invention is directed to bicyclic compounds that are inhibitors of mammalian Target Of Rapamycin (mTOR) kinase (also known as FRAP, RAFT, RAPT, SEP). In particular, the present invention is directed to fused bicyclic compounds that are mTOR inhibitors useful in the treatment of cancer.

International Patent Publication WO 2001 019828 describes the preparation of heteroaromatic amines as protein kinase inhibitors. International Patent Publication WO 2005/047289 describes pyrrolopyrimidine compounds useful in treatment of cancer.

It has been shown that high levels of dysregulated mTOR activity are associated with variety of human cancers and several hamartoma syndromes, including tuberous sclerosis complex, the PTEN-related hamartoma syndromes and Peutz-Jeghers syndrome. Although rapamycin analogues are in clinical development for cancer as mTOR kinase inhibitor, the clinical out come with CCI-779 is just modest in breast and renal cancer patients. This is probably because rapamycin partially inhibits mTOR function through raptor-mTOR complex (mTORC1). It has been also found that ⅔ of the breast cancer and ½ of renal cancer patients are resistant to rapamycin therapy. With a recent discovery of rictor-mTOR complex (mTORC2) which is involved in phosphorylation of AKT (S473) that is important in regulation of cell survival and modulation of PKCα that plays a major role in regulation of actin cytoskeletal organization in a rapamycin-independent manner, and inhibition of these activities of mTOR is probably important for broader antitumor activity and better efficacy. Therefore, it is desirable to develop novel compounds that are direct inhibitors of mTOR kinase, which would inhibit mTORC1 and mTORC2.

Rapamycin, a macrolide antibiotic has been shown to specifically inhibit mTOR kinase activity in vitro and in vivo in several studies. Although precise mechanism by which rapamycin inhibits mTOR function is not well understood, it is known that rapamycin first binds to FKBP12 (FK506 binding protein) and then binds to FRB domain of mTOR and thus inhibit mTOR activity by inducing conformational changes, which inhibits substrate binding. Rapamycin has been widely used as a specific mTOR inhibitor in preclinical studies to demonstrate role of mTOR in signal transduction and cancer. But rapamycin was not developed as a cancer therapy because of stability and solubility problems even though significant antitumor activity was observed in the NCI screening programme. However, synthesis of rapamycin analogues with superior solubility and stability properties has led to run the clinical trails with CCI-779, RAD001 and AP23573. The most advanced rapamycin analogue, CCI-779 has shown modest anti-tumor activity in Phase II breast, renal carcinoma and mantle cell lymphoma clinical trials.

The Tor genes were originally identified in yeast as the targets of the drug rapamycin. The structurally and functionally conserved mammalian counter part of yeast TOR, mTOR was later discovered. mTOR is a member of the phosphoinositide kinase-related kinase (PIKK) family, but rather than phosphorylating phosphoinositides, phosphorylates proteins on serine or threonine residues. Genetic studies have shown that mTOR is essential for cell growth and development in fruit flies, nematodes and mammals, and the disruption of the genes encoding mTOR results in lethality in all species. Several studies have demonstrated that mTOR has a central role in controlling cell growth, proliferation and metabolism. mTOR regulates a wide range of cellular functions, including translation, transcription, mRNA turnover, protein stability, actin cytoskeletal organization and autophagy. There are two mTOR complexes in mammalian cells. MTOR complex I (mTORC1) is a raptor-mTOR complex, which mainly regulates cell growth in a rapamycin-sensitive manner whereas mTOR complex II (mTORC2) is a rictor-mTOR complex, which regulates cytoskeletal organization in a rapamycin-insensitive manner.

The best-characterized function of mTOR in mammalian cells is regulation of translation. Ribosomal S6 kinase (S6K) and eukaryotic initiation factor 4E binding protein 1 (4E-BP1), the most extensively studied substrates of mTOR, are key regulators of protein translation. S6K is the major ribosomal protein kinase in mammnalian cells. Phosphorylation of S6 protein by S6K selectively increases the translation of mRNAs containing a tract of pyrimidines motif; these mRNAs often encode ribosomal proteins and other translational regulators. Thus, S6K enhances overall translation capacity of cells. 4E-BP1, another well-characterized mTOR target, acts as a translational repressor by binding and inhibiting the eukaryotic translation initiation factor 4E (eIF4E), which recognizes the 5' end cap of eukaryotic mRNAs. Phosphorylation of 4E-BP1 by mTOR results in a dissociation of 4E-BP1 from eIF4E, thereby relieving the inhibition of 4E-BP1 on eIF4E-dependent translation initiation. eIF4E overexpression enhances cell growth and transforms cells by increasing the translation of a subset of key growth-promoting proteins, including cyclin D1, c-Myc and VEGF. Therefore, mTOR-dependent regulation of both 4E-BP1 and S6K might be one mechanism by which mTOR positively regulates cell growth. mTOR integrates two of the most important extracellular and intracellular signals involved in the regulation of cell growth: growth factors and nutrients. Growth factor, such as insulin or IGF1 and nutrients, such as amino acids or glucose, enhance mTOR function, as evidenced by an increased phosphorylation of S6K and 4E-BP1. Rapamycin or dominant negative mTOR inhibits these effects, indicating that mTOR integrates the regulation of signals from growth factors and nutrients.

Signalling pathways that are upstream and downstream of mTOR are often deregulated in variety of cancers, including breast, lung, kidney, prostate, blood, liver, ovarian, thyroid, GI tract and lymphoma. Oncogenes including overexpressed receptor tyrosine kinases and constitutively activated mutant receptors activate PI3K-mediated signaling pathways. Additional alterations of the PI3K-mTOR pathway in human cancers include amplification of the p110 catalytic subunit of PI3K, loss of PTEN phosphatase function, amplification of AKT2, mutations in TSC1 or TSC2, and overexpression or amplification of eIF4E or S6K1. Mutation or loss of heterozygosity in TSC1 and TSC2 most often give rise to Tuberous Sclerosis (TSC) syndrome. TSC is rarely associated with malignant tumors, although patients with TSC are at risk for malignant renal cancer of clear-cell histology. Although inactivation of TSC might not lead to malignancy per se, deregulation of this pathway seems crucial for angiogenesis in developing malignancies. TSC2 regulates VEGF production through mTOR-dependent and -independent manner.

With the recent discovery of rapamycin independent function of mTOR (by mTOR2) in phosphorylation AKT (at S473) that is important in regulation of cell survival and modulation of PKCα, which plays a major role in regulation of actin cytoskeletal organization, it is believed that inhibition of mTOR function by rapamycin is partial. Therefore, discovery of a direct mTOR kinase inhibitor, which would completely inhibit the function of both mTORC1 and mTORC2, is required for broader anti-tumor activity and better efficacy. Here we describe the discovery of direct mTOR kinase inhibitors, which can be used in the treatment of variety of cancers—including breast, lung, kidney, prostate, blood, liver, ovarian, thyroid, GI tract and lymphoma—and other indications such as rheumatoid arthritis, hamartoma syndromes, transplant rejection, IBD, multiple sclerosis and immunosuppression.

Recent success of Tarceva™, an EGFR kinase inhibitor for the treatment of NSCLC and prior success with Gleevec™ for the treatment of CML indicate that it is possible to develop selective kinase inhibitors for the effective treatment of cancers. Although there are several anti-cancer agents including kinase inhibitors, there is still continuing need for improved anti-cancer drugs, and it would be desirable to develop new compounds with better selectivity, potency or with reduced toxicity or side effects.

Thus, it is desirable to develop compounds that exhibit mTOR inhibition in order to treat cancer patients. Further, such compounds may be active in other kinases such as, for example, PI3K, Src, KDR, to add efficacy in breast, non-small cell lung cancer (NSCLC), renal cell carcinoma, mantle cell lymphoma, endometrial cancers, or other hamartoma syndromes.

SUMMARY OF THE INVENTION

Compounds represented by Formula (I)

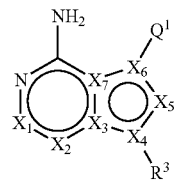

(I)

or a pharmaceutically acceptable salt thereof, are inhibitors of mTOR and useful in the treatment of cancer.

DETAILED DESCRIPTION OF THE INVENTION

The compounds of the present invention are represented by Formula (I)

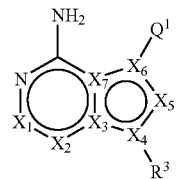

(I)

or a pharmaceutically acceptable salt thereof, wherein:
$X_1$, and $X_2$ are each independently N or C-$(E^1)_{aa}$;
$X_5$ is N, C-$(E^1)_{aa}$, or N-$(E^1)_{aa}$;
$X_3$, $X_4$, $X_6$, and $X_7$ are each independently N or C;
wherein at least one of $X_3$, $X_4$, $X_5$, $X_6$, and $X_7$ is independently N or N-$(E^1)_{aa}$;

$R^3$ is $C_{0-10}$alkyl, cyclo$C_{3-10}$alkyl, aminomethylcyclo$C_{3-10}$alkyl, bicyclo$C_{5-10}$alkyl, aryl, heteroaryl, aralkyl, heteroaralkyl, heterocyclyl or heterobicyclo$C_{5-10}$alkyl any of which is optionally substituted by one or more independent $G^{11}$ substituents;
$Q^1$ is -A-$(K)_m$
A is vinyl or acetylenyl
K is independently, hydrogen, —N($C_{0-8}$alkyl)($C_{0-8}$alkyl), hydroxyl, halogen, oxo, aryl (optionally substituted with 1 or more $R^{31}$ groups), hetaryl (optionally substituted with 1 or more $R^{31}$ groups), $C_{0-6}$alkyl, —$C_{0-8}$alkyl$C_{3-8}$cycloalkyl, —$C_{0-8}$alkyl-NR$^{311}$S(O)$_{0-2}$R$^{321}$, —$C_{0-8}$alkyl-NR$^{311}$S(O)$_{0-2}$NR$^{321}$R$^{331}$, —$C_{0-8}$alkyl-NR$^{311}$CO$_2$R$^{321}$, —$C_{0-8}$alkyl-CON(R$^{311}$) S(O)$_{0-2}$R$^{321}$, —$C_{0-8}$alkyl-S(O)$_{0-2}$NR$^{311}$R$^{321}$, —$C_{0-8}$alkyl-NR$^{311}$COR$^{321}$, —$C_{0-8}$alkyl-NR$^{311}$CONR$^{321}$R$^{331}$, —$C_{0-8}$alkyl-CONR$^{311}$R$^{321}$, —$C_{0-8}$alkyl-CO$_2$R$^{311}$, —$C_{0-8}$alkyl-COR$^{311}$, —$C_{0-8}$alkylS(O)$_{0-2}$R$^{311}$, —$C_{0-8}$alkyl-O—$C_{1-8}$alkyl, —$C_{0-8}$alkyl-O—$C_{0-8}$alkyl$C_{3-8}$cycloalkyl, —$C_{0-8}$-alkyl-O—$C_{0-8}$alkylheterocycloalkyl, —$C_{0-8}$alkyl-O—$C_{0-8}$alkylaryl, —$C_{0-8}$alkyl-O—$C_{0-8}$alkylhetaryl, —$C_{0-8}$alkylaryl, —$C_{0-8}$alkylhetaryl, —$C_{0-8}$ alkylheterocyclyl, —$C_{0-8}$alkyl-S—$C_{0-8}$alkyl, —$C_{0-8}$ alkyl-S—$C_{0-8}$alkyl$C_{3-8}$cycloalkyl, —$C_{0-8}$alkyl-S—$C_{0-8}$alkylheterocycloalkyl, —$C_{0-8}$alkyl-S—$C_{0-8}$alkylaryl, —$C_{0-8}$alkyl-S—$C_{0-8}$alkylhetaryl, —$C_{0-8}$alkyl-N(R$^{311}$)—$C_{0-8}$alkyl, —$C_{0-8}$alkyl-N(R$^{311}$)—$C_{0-8}$alkyl$C_{3-8}$cycloalkyl, —$C_{0-8}$alkyl-N(R$^{311}$)—$C_{0-8}$alkylheterocycloalkyl, —$C_{0-8}$alkyl-N(R$^{311}$)—$C_{0-8}$alkylaryl, —$C_{0-8}$alkyl-N(R$^{311}$)—$C_{0-8}$alkylhetaryl, —$C_{0-8}$alkyl-NR$^{311}$R$^{321}$, —$C_{2-8}$alkenyl, —$C_{2-8}$alkynyl, NO$_2$, CN, CF$_3$, OCF$_3$, OCHF$_2$;

$R^{31}$, $R^{32}$, $R^{33}$, $R^{311}$, $R^{321}$, $R^{331}$, $R^{312}$, $R^{322}$, $R^{332}$, $R^{341}$, $R^{313}$, $R^{323}$, $R^{333}$, and $R^{342}$, in each instance, is independently $C_{0-8}$alkyl optionally substituted with 1-6 independent aryl, cyclyl, heterocyclyl, hetaryl, halo, —CON($C_{0-8}$alkyl)($C_{0-8}$alkyl), —CO($C_{0-8}$alkyl), —O$C_{0-8}$alkyl, —Oaryl, —Ohetaryl, —Oheterocyclyl, —S(O)$_{0-2}$aryl, —S(O)$_{0-2}$hetaryl, —S(O)$_{0-2}$heterocyclyl, —S(O)$_{0-2}$C$_{0-8}$alkyl, —N(C$_{0-8}$alkyl)(C$_{0-8}$alkyl), —N(C$_{0-8}$alkyl)CON(C$_{0-8}$alkyl)(C$_{0-8}$alkyl), —N(C$_{0-8}$ alkyl)CO(C$_{1-8}$alkyl), —N(C$_{0-8}$alkyl)CO (C$_{3-8}$cycloalkyl), —N(C$_{0-8}$alkyl)CO$_2$(C$_{1-8}$alkyl), —S(O)$_{1-2}$ N(C$_{0-8}$alkyl)C$_{0-8}$alkyl), —NR$^{11}$S(O)$_{1-2}$ (C$_{0-8}$alkyl), —CON(C$_{3-8}$cycloalkyl)(C$_{3-8}$cycloalkyl), —CON(C$_{0-8}$alkyl)(C$_{3-8}$cycloalkyl), —N(C$_{3-8}$cycloalkyl)CON(C$_{0-8}$alkyl)(C$_{0-8}$alkyl), —N(C$_{3-8}$cycloalkyl)CON(C$_{3-8}$cycloalkyl)(C$_{0-8}$alkyl), —N(C$_{0-8}$alkyl)CON(C$_{3-8}$cycloalkyl)(C$_{0-8}$alkyl), —N(C$_{0-8}$alkyl)CO$_2$(C$_{3-8}$cycloalkyl), —N(C$_{3-8}$ cycloalkyl)CO$_2$(C$_{3-8}$cycloalkyl), S(O)$_{1-2}$N (C$_{0-8}$ alkyl)(C$_{3-8}$cycloalkyl), —NR$^{11}$S(O)$_{1-2}$(C$_{3-8}$cycloalkyl), C$_{2-8}$alkenyl, C$_{2-8}$alkynyl, CN, CF$_3$, OH, or optionally substituted aryl substituents; such that each of the above aryl, heterocyclyl, hetaryl, alkyl or cycloalkyl groups may be optionally, independently substituted with —N(C$_{0-8}$alkyl)(C$_{0-8}$alkyl), hydroxyl, halogen, oxo, aryl, hetaryl, C$_{0-6}$alkyl, C$_{0-8}$alkylcyclyl, —C$_{0-8}$alkyl-N(C$_{0-8}$alkyl)—S(O)$_{0-2}$ —(C$_{0-8}$alkyl), —C$_{0-8}$alkyl-S(O)$_{0-2}$—N(C$_{0-8}$alkyl) (C$_{0-8}$alkyl), —C$_{0-8}$alkyl-N(C$_{0-8}$alkyl)CO(C$_{0-8}$alkyl), —C$_{0-8}$alkyl-N(C$_{0-8}$alkyl)CO—N(C$_{0-8}$alkyl)(C$_{0-8}$ alkyl), —C$_{0-8}$alkyl-CO—N(C$_{0-8}$alkyl)(C$_{0-8}$alkyl), —C$_{1-8}$alkyl-CO$_2$—C$_{0-8}$alkyl), —C$_{0-8}$alkylS(O)$_{0-2}$—(C$_{0-8}$alkyl), —C$_{0-8}$alkyl-O—C$_{1-8}$alkyl, —C$_{0-8}$alkyl-O—C$_{0-8}$alkylcyclyl, —C$_{0-8}$alkyl-O—C$_{0-8}$alkylheterocyclyl, —C$_{0-8}$alkyl-O—C$_{0-8}$alkylaryl, —C$_{0-8}$alkyl-O—C$_{0-8}$alkylhetaryl, —C$_{0-8}$alkyl-S—C$_{08}$alkyl, —C$_{0-8}$alkyl-S—C$_{0-8}$alkylcyclyl, —C$_{0-8}$alkyl-S—C$_{0-8}$alkylheterocyclyl, —C$_{0-8}$alkyl-S—C$_{0-8}$ alkylaryl, —C$_{0-8}$alkyl-S—C$_{0-8}$alkylhetaryl, —C$_{0-8}$ alkyl-N(C$_{0-8}$alkyl)-C$_{0-8}$alkyl, —C$_{0-8}$alkyl-N(C$_{0-8}$ alkyl)-C$_{0-8}$alkylcyclyl, —C$_{0-8}$alkyl-N(C$_{0-8}$alkyl)-C$_{0-8}$alkylheterocyclyl, —C$_{0-8}$alkyl-N(C$_{0-8}$alkyl)-C$_{0-8}$alkylaryl, —C$_{0-8}$alkyl-N(C$_{0-8}$alkyl)-C$_{0-8}$alkylhetaryl, C$_{2-8}$alkenyl, C$_{2-8}$alkynyl, NO$_2$, CN, CF$_3$, OCF$_3$, OCHF$_2$,
—C$_{0-8}$alkyl-C$_{3-8}$cycloalkyl,
—C$_{0-8}$alkyl-O—C$_{0-8}$alkyl,
—C$_{0-8}$alkyl-N(C$_{0-8}$alkyl)(C$_{0-8}$alkyl),
—C$_{0-8}$alkyl-S(O)$_{0-2}$—C$_{0-8}$alkyl, or
heterocyclyl optionally substituted with 1-4 independent C$_{0-8}$alkyl, cyclyl, or substituted cyclyl substituents;

E$^1$ in each instance is independently halo, —CF$_3$, —OCF$_3$, —OR$^2$, —NR$^{31}$R$^{32}$, —C(=O)R$^{31}$, —CO$_2$R$^{31}$, —CONR$^{31}$R$^{32}$, —NO$_2$, —CN, —S(O)$_{0-2}$R$^{31}$, —S(O)$_{0-2}$NR$^{31}$R$^{32}$, —NR$^{31}$C(=O)R$^{32}$, —NR$^{31}$C(=O)OR$^{32}$, —NR$^{31}$C(=O)NR$^{32}$R$^{33}$, —NR$^{31}$S(O)$_{0-2}$R$^{32}$, —C(=S)OR$^{31}$, —C(=O)SR$^{31}$, —NR$^{31}$C(=NR$^{32}$)NR$^{33}$R$^{31}$, —NR$^{31}$C(=NR$^{32}$)OR$^{33}$, —NR$^{31}$C(=NR$^{31}$)SR$^{31}$, —OC(=O)OR$^{31}$, —OC(=O)NR$^{31}$R$^{32}$, —OC(=O)SR$^{31}$, —SC(=O)OR$^{31}$, —SC(=O)NR$^{31}$R$^{32}$, C$_{0-10}$alkyl, C$_{2-10}$alkenyl, C$_{2-10}$alkynyl, —C$_{1-10}$alkoxyC$_{1-10}$alkyl, —C$_{1-10}$alkoxyC$_{2-10}$alkenyl, —C$_{1-10}$alkoxyC$_{2-10}$alkynyl, —C$_{1-10}$alkylthioC$_{1-10}$alkyl, —C$_{1-10}$alkylthioC$_{2-10}$alkenyl, —C$_{1-10}$alkylthioC$_{2-10}$alkynyl, cycloC$_{3-8}$alkyl, cycloC$_{3-8}$alkenyl, -cycloC$_{3-8}$alkylC$_{1-10}$ alkyl, -cycloC$_{3-8}$alkenylC$_{1-10}$alkyl, -cycloC$_{3-8}$ alkylC$_{2-10}$alkenyl, -cycloC$_{3-8}$alkenylC$_{2-10}$alkenyl, -cycloC$_{3-8}$alkylC$_{2-10}$alkynyl, -cycloC$_{3-8}$alkenylC$_{2-10}$alkynyl, -heterocyclyl-C$_{0-10}$alkyl, -heterocyclyl-C$_{2-10}$alkenyl, or -heterocyclyl-C$_{2-10}$alkynyl, any of which is optionally substituted with one or more independent halo, oxo, —CF$_3$, —OCF$_3$, —OR$^{31}$, —NR$^{31}$R$^{32}$, —C(=O)R$^{31}$, —CO$_2$R$^{31}$, —C(=O)NR$^{31}$R$^{32}$, —NO$_2$, —CN, —S(=O)$_{0-2}$R$^{31}$, —SO$_2$NR$^{31}$, —NR$^{31}$C(=O)R$^{32}$, —NR$^{31}$C(=O)OR$^{31}$, —NR$^{31}$C(=O)NR$^{32}$R$^{33}$, —NR$^{31}$S(O)$_{0-2}$R$^{31}$, —C(=S)R$^{31}$, —C(=O)SR$^{31}$, —NR$^{31}$C(=NR$^{32}$)NR$^{33}$R$^{31}$, —NR$^{31}$C(=NR$^{32}$)OR$^{33}$, —NR$^{31}$C(=NR$^{32}$)SR$^{33}$, —OC(=O)OR$^{31}$, —OC(=O)NR$^{31}$R$^{32}$, —OC(=O)SR$^{31}$, —SC(=O)OR$^{31}$, or —SC(=O)NR$^{31}$R$^{32}$ substituents;

or E$^1$ in each instance is independently aryl-C$_{0-10}$alkyl, aryl-C$_{2-10}$alkenyl, aryl-C$_{2-10}$alkynyl, hetaryl-C$_{0-10}$alkyl, hetaryl-C$_{2-10}$alkenyl, or hetaryl-C$_{2-10}$alkynyl, where the attachment point is from either the left or right as written, where any of which is optionally substituted with one or more independent halo, —CF$_3$, —OCF$_3$, —OR$^{31}$, —NR$^{31}$R$^{32}$, —C(O)R$^{31}$, —CO$_2$R$^{31}$, —C(=O)NR$^{31}$R$^{32}$, —NO$_2$, —CN, —S(O)$_{0-2}$R$^{31}$, —S(O)$_{0-2}$NR$^{31}$R$^{32}$, —NR$^{31}$C(=O)R$^{32}$, —NR$^{31}$C(=O)OR$^{32}$, —NR$^{31}$C(=O)NR$^{32}$R$^{33}$, —NR$^{31}$S(O)$_{0-2}$R$^{32}$, —C(=S)OR$^{31}$, —C(=O)SR$^{31}$, —NR$^{31}$C(=NR$^{32}$)NR$^{33}$R$^{31}$, —NR$^{31}$C(=NR$^{32}$)OR$^{33}$, —NR$^{31}$C(=NR$^{32}$)SR$^{33}$, —OC(=O)OR$^{31}$, —OC(=O)NR$^{31}$R$^{32}$, —OC(=O)SR$^{31}$, —SC(=O)OR$^{31}$, or —SC(=O)NR$^{31}$R$^{32}$ substituents;

in the cases of —NR$^{31}$R$^{32}$, —NR$^{311}$R$^{321}$, —NR$^{312}$R$^{322}$, —NR$^{332}$R$^{341}$, —NR$^{313}$R$^{323}$, and —NR$^{323}$R$^{333}$, the respective R$^{31}$ and R$^{32}$, R$^{311}$ and R$^{321}$, R$^{312}$ and R$^{322}$, R$^{331}$ and R$^{341}$, R$^{313}$ and R$^{323}$, and R$^{323}$ and R$^{333}$ are optionally taken together with the nitrogen atom to which they are attached to form a 3-10 membered saturated or unsaturated ring; wherein said ring in each instance independently is optionally substituted by one or more independent —N(C$_{0-8}$alkyl)(C$_{0-8}$alkyl), hydroxyl, halogen, oxo, aryl, hetaryl, C$_{0-6}$alkyl, —C$_{0-8}$alkylC$_{3-8}$cycloalkyl, —C$_{0-8}$alkyl-N(C$_{0-8}$alkyl)S(O)$_{0-2}$C$_{0-8}$alkyl, —C$_{0-8}$alkyl-N(C$_{0-8}$alkyl)S(O)$_{0-2}$N(C$_{0-8}$alkyl)( C$_{0-8}$alkyl), —C$_{0-8}$alkyl-N(C$_{0-8}$alkyl)CO$_2$(C$_{0-8}$alkyl), —C$_{0-8}$alkyl-CON((C$_{0-8}$alkyl))S(O)$_{0-2}$(C$_{0-8}$alkyl), —C$_{0-8}$alkyl-S(O)$_{0-2}$N(C$_{0-8}$alkyl)(C$_{0-8}$alkyl), —C$_{0-8}$alkyl-N(C$_{0-8}$alkyl)CO(C$_{0-8}$alkyl), —C$_{0-8}$alkyl-N(C$_{0-8}$alkyl)CON(C$_{0-8}$alkyl)(C$_{0-8}$alkyl), —C$_{0-8}$alkyl-CON(C$_{0-8}$alkyl)(C$_{0-8}$alkyl), —C$_{0-8}$alkyl-CO$_2$(C$_{0-8}$alkyl), —C$_{0-8}$alkylS(O)$_{0-2}$(C$_{0-8}$alkyl), —C$_{0-8}$alkyl-O—C$_{0-8}$alkyl, —C$_{0-8}$alkyl-O—C$_{0-8}$alkylcyclyl, —C$_{0-8}$alkyl-O—C$_{0-8}$alkylheterocycloalkyl, —C$_{0-8}$alkyl-O—C$_{0-8}$alkylaryl, —Oaryl, —C$_{0-8}$alkyl-O—C$_{0-8}$ alkyl-hetaryl, —C$_{0-8}$alkyl-S—C$_{0-8}$alkyl, —C$_{0-8}$alkyl-S—C$_{0-8}$ alkylC$_{3-8}$cycloalkyl, —C$_{0-8}$alkyl-S—C$_{0-8}$alkylheterocycloalkyl, —C$_{0-8}$alkyl-S—C$_{0-8}$alkylaryl, —C$_{0-8}$alkyl-S—C$_{0-8}$alkylhetaryl, —C$_{0-8}$alkyl-N(C$_{0-8}$alkyl)-C$_{0-8}$alkyl, —C$_{0-8}$alkyl-N(C$_{0-8}$alkyl)-C$_{0-8}$alkylC$_{3-8}$cycloalkyl, —C$_{0-8}$alkyl-N(C$_{0-8}$alkyl)-C$_{0-8}$alkylheterocycloalkyl, —C$_{0-8}$alkyl-N(C$_{0-8}$alkyl)-C$_{0-8}$alkylaryl, —C$_{0-8}$alkyl-N(C$_{0-8}$alkyl)-C$_{0-8}$alkylhetaryl, —C$_{0-8}$alkyl-N(C$_{0-8}$alkyl)(C$_{0-8}$alkyl), C$_{2-8}$alkenyl, C$_{2-8}$alkynyl, NO$_2$, CN, CF$_3$, OCF$_3$, or OCHF$_2$substituents; wherein said ring in each instance independently optionally includes one or more heteroatoms other than the nitrogen;

m is 0, 1, 2,or 3;

aa is 0 or 1; and provided that the compound is not 3-cyclobutyl-1-[(4-phenoxyphenyl)ethynyl]imidazo[1,5-a]pyrazin-8-amine, 3-cyclobutyl-1-[(1-methyl-1H-imidazol-5-yl)ethynyl]imidazo[1,5-a]pyrazin-8-amine, N-{3-[(8-amino-3-cyclobutylimidazo[1,5-a]pyrazin-1-yl)ethynyl]phenyl}-4-chlorobenzamide or 3-cyclobutyl-1-(pyridin-4-ylethynyl)imidazo[1,5-a]pyrazin-8-amine.

According to an aspect of the present invention, the compounds are represented by Formula I, or a pharmaceutically acceptable salt thereof, wherein X$_1$ and X$_2$ are CH; X$_3$ and X$_5$ are N; and X$_4$, X$_6$ and X$_7$ are C; and the other variables are as described above for Formula I.

In an embodiment of this aspect of the present invention, the compounds are represented by Formula I, or a pharmaceutically acceptable salt thereof, wherein X$_1$ and X$_2$ are CH; X$_3$ and X$_5$ are N; and X$_4$, X$_6$ and X$_7$ are C; Q$^1$ is -A(K)$_m$; and the other variables are as described above for Formula I.

According to a second aspect of the present invention, the compounds are represented by Formula I, or a pharmaceutically acceptable salt thereof, wherein X$_1$ is CH; X$_2$, X$_3$ and X$_5$ are N; and X$_4$, X$_6$ and X$_7$ are C; and the other variables are as described above for Formula I.

In an embodiment of the second aspect of the present invention, the compounds are represented by Formula I, or a pharmaceutically acceptable salt thereof, wherein X$_1$ is CH; X$_2$, X$_3$ and X$_5$ are N; and X$_4$, X$_6$ and X$_7$ are C; Q$^1$ is -A(K)$_m$; and the other variables are as described above for Formula I.

The compounds of the present invention include:

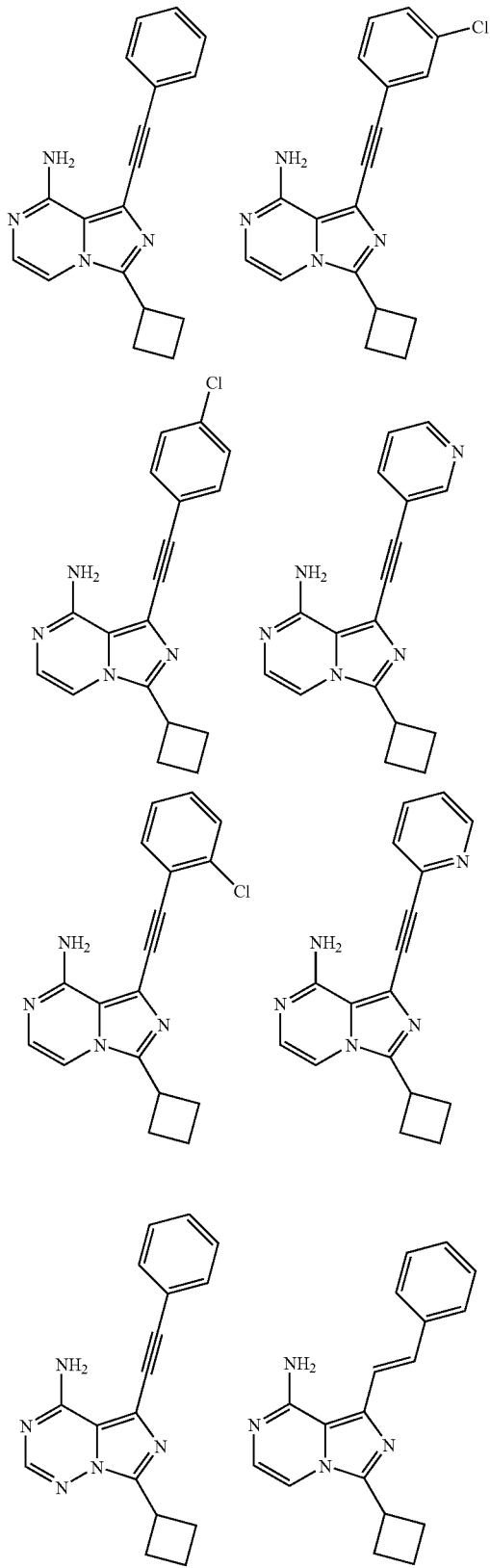

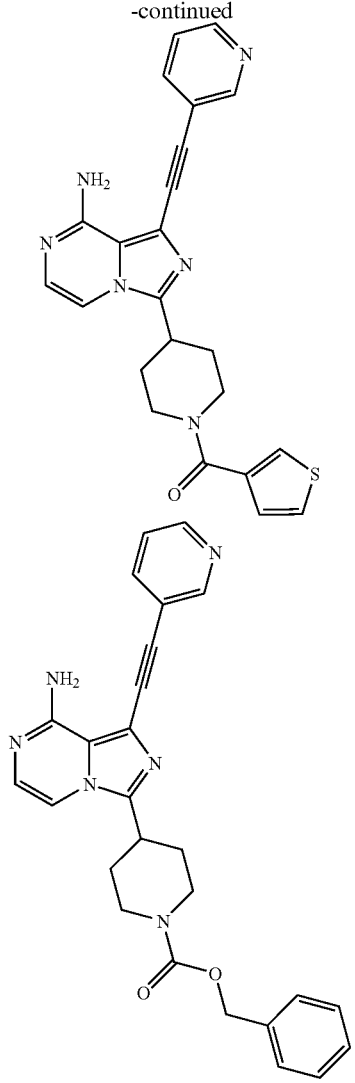

or a pharmaceutically acceptable salt thereof.

The present invention includes a composition comprising a compound according to Formula I, or a pharmaceutically acceptable salt thereof, and a pharmaceutically acceptable carrier.

The present invention includes a composition comprising a compound according to Formula I, or a pharmaceutically acceptable salt thereof; and an anti-neoplastic, anti-tumor, anti-angiogenic, or chemotherapeutic agent.

The present invention includes a method of treatment of hyperproliferative disorder comprising a step of administering an effective amount of a compound according to Formula I, or a pharmaceutically acceptable salt thereof.

The present invention includes a method of treatment of hyperproliferative disorder comprising a step of administering an effective amount of a compound according to Formula I, or a pharmaceutically acceptable salt thereof, wherein the hyperproliferative disorder is breast cancer, lung cancer, non-small cell lung cancer, kidney cancer, renal cell carcinoma, prostate cancer, cancer of the blood, liver cancer, ovarian cancer, thyroid cancer, endometrial cancer, cancer of the GI tract, lymphoma, renal cell carcinoma, mantle cell lymphoma, or endometrial cancer.

The present invention includes a method of treatment of rheumatoid arthritis, hamartoma syndromes, transplant rejection, IBD, multiple sclerosis or immunosuppression diseases comprising a step of administering an effective amount of the compound according to Formula I, or a pharmaceutically acceptable salt thereof.

In all of the above circumstances forbidden or unstable valences, N—S, N-halogen bonds are excluded.

As used herein, the terms $C\text{-}(E^1)_{aa}$, and $N\text{-}(E^1)_{aa}$ are understood to represent ring carbon or nitrogen atoms respectively that are substituted by aa number of $E^1$ substituents.

As used herein, unless stated otherwise, "alkyl" as well as other groups having the prefix "alk" such as, for example, alkoxy, alkanyl, alkenyl, alkynyl, and the like, means carbon chains which may be linear or branched or combinations thereof. Examples of alkyl groups include methyl, ethyl, propyl, isopropyl, butyl, sec- and tert-butyl, pentyl, hexyl, heptyl and the like. "Alkenyl", "alkynyl" and other like terms include carbon chains having at least one unsaturated carbon-carbon bond.

As used herein, "$C_{0-4}$alkyl" for example is used to mean an alkyl having 0-4 carbons—that is, 0, 1, 2, 3, or 4 carbons in a straight or branched configuration. An alkyl having no carbon is hydrogen when the alkyl is a terminal group. An alkyl having no carbon is a direct bond when the alkyl is a bridging (connecting) group.

The terms "cycloalkyl", "carbocyclic ring", "cyclic", or "cyclyl" mean 3-10 membered mono or polycyclic aromatic, partially aromatic or non-aromatic ring carbocycles containing no heteroatoms, and include mono-, bi-, and tricyclic saturated carbocycles, as well as fused and bridged systems. Such fused ring systems can include one ring that is partially or fully unsaturated, such as a benzene ring, to form fused ring systems, such as benzofused carbocycles. Cycloalkyl includes such fused ring systems as spirofused ring systems. Examples of cycloalkyl and carbocyclic rings include $C_{3-8}$cycloalkyl such as cyclopropyl, cyclobutyl, cyclopentyl, cyclohexyl, and decahydronaphthalene, adamantane, indanyl, 1,2,3,4-tetrahydronaphthalene and the like.

The term "halogen" includes fluorine, chlorine, bromine, and iodine atoms.

The term "carbamoyl" unless specifically described otherwise means —C(O)—NH— or —NH—C(O)—.

The term "aryl" is well known to chemists. The preferred aryl groups are phenyl and naphthyl.

The term "hetaryl" is well known to chemists. The term includes 5- or 6-membered heteroaryl rings containing 1-4 heteroatoms chosen from oxygen, sulfur, and nitrogen in which oxygen and sulfur are not next to each other. Examples of such heteroaryl rings are furyl, thienyl, pyrrolyl, pyrazolyl, imidazolyl, oxazolyl, isoxazolyl, thiazolyl, isothiazolyl, triazolyl, oxadiazolyl, thiadiazolyl, tetrazolyl, pyridyl, pyridazinyl, pyrimidinyl, pyrazinyl, and triazinyl. The term "hetaryl" includes hetaryl rings with fused carbocyclic ring systems that are partially or fully unsaturated, such as a benzene ring, to form a benzofused hetaryl. For example, benzimidazole, benzoxazole, benzothiazole, benzofuran, quinoline, isoquinoline, quinoxaline, and the like.

Unless otherwise stated, the terms "heterocyclic ring", "heterocycle", "heterocyclic", and "heterocyclyl" are equivalent, and is defined as for cyclic but also contains one or more atoms chosen independently from N, O, and S (and the N and S oxides), provided such derivatives exhibit appropriate and stable valencies. The terms include 4-8-membered saturated rings containing one or two heteroatoms chosen from oxygen, sulfur, and nitrogen. Examples of heterocyclic rings include azetidine, oxetane, tetrahydrofuran, tetrahydropyran, oxepane, oxocane, thietane, thiazolidine, oxazolidine, oxazetidine, pyrazolidine, isoxazolidine, isothiazolidine, tetrahydrothiophene, tetrahydrothiopyran, thiepane, thiocane, azetidine, pyrrolidine, piperidine, azepane, azocane, [1,3]dioxane, oxazolidine, piperazine, homopiperazine, morpholine, thiomorpholine, and the like. Other examples of heterocyclic rings include the oxidized forms of the sulfur-containing rings. Thus, tetrahydrothiophene-1-oxide, tetrahydrothiophene-1,1-dioxide, thiomorpholine-1-oxide, thiomorpholine-1,1-dioxide, tetrahydrothiopyran-1-oxide, tetrahydrothiopyran-1,1-dioxide, thiazolidine-1-oxide, and thiazolidine-1,1-dioxide are also considered to be heterocyclic rings. The term "heterocyclic" also includes fused ring systems, including het-het fused systems, and can include a carbocyclic ring that is partially or fully unsaturated, such as a benzene ring, to form benzofused heterocycles. For example, 3,4,-dihydro-1,4-benzodioxine, tetrahydroquinoline, tetrahydroisoquinoline, isoiindoline and the like.

Compounds described herein may contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof. The above Formula I is shown without a definitive stereochemistry at certain positions. The present invention includes all stereoisomers of Formula I and pharmaceutically acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be a mixture of stereoisomers.

The invention also encompasses a pharmaceutical composition that is comprised of a compound of Formula I in combination with a pharmaceutically acceptable carrier.

Preferably the composition is comprised of a pharmaceutically acceptable carrier and a therapeutically effective amount of a compound of Formula I as described above (or a pharmaceutically acceptable salt thereof).

Moreover, within this preferred embodiment, the invention encompasses a pharmaceutical composition for the treatment of disease by inhibition of mTor, comprising a pharmaceutically acceptable carrier and a non-toxic therapeutically effective amount of compound of formula I as described above (or a pharmaceutically acceptable salt thereof).

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Particularly preferred are the ammonium, calcium, magnesium, potassium and sodium slats. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N',N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylameine, trimethylamine, tripropylamine, tromethamine and the like.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric and tartaric acids.

The pharmaceutical compositions of the present invention comprise a compound represented by formula I (or a pharmaceutically acceptable salt thereof) as an active ingredient, a pharmaceutically acceptable carrier and optionally other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

In practice, the compounds represented by Formula I, or pharmaceutically acceptable salts thereof, of this invention can be combined as the active ingredient in intimate admixture with a pharmaceutical carrier according to conventional pharmaceutical compounding techniques. The carrier may take a wide variety of forms depending on the form of preparation desired for administration. e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion, or as a water-in-oil liquid emulsion. In addition to the common dosage forms set out above, the compound represented by Formula I, or a pharmaceutically acceptable salt thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and a compound or a pharmaceutically acceptable salt of Formula I. The compounds of Formula I, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents, and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.05 mg to about 5 g of the active ingredient and each cachet or capsule preferably containing from about 0.05 mg to about 5 g of the active ingredient.

For example, a formulation intended for the oral administration to humans may contain from about 0.5 mg to about 5 g of active agent, compounded with an appropriate and convenient amount of carrier material, which may vary from about 5 to about 95 percent of the total composition. Unit dosage forms will generally contain between from about 1 mg to about 2 g of the active ingredient, typically 25 mg, 50 mg, 100 mg, 200 mg, 300 mg, 400 mg, 500 mg, 600 mg, 800 mg, or 1000 mg.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical sue such as, for example, an aerosol, cream, ointment, lotion, dusting powder, or the like. Further, the compositions can be in a form suitable for use in transdermal devices. These formulations may be prepared, utilizing a compound represented by Formula I of this invention, or a pharmaceutically acceptable salt thereof, via conventional processing methods. As an example, a cream or ointment is prepared by admixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. He suppositories may be conveniently formed by first admixing the composition with the softened or melted carrier(s) followed by chilling and shaping in molds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound described by Formula I, or pharmaceutically acceptable salts thereof, may also be prepared in powder or liquid concentrate form.

The compounds and compositions of the present invention are useful in the treatment of cancers of the breast, lung, kidney, prostate, blood, liver, ovarian, thyroid, GI tract and lymphoma. The compounds and compositions are useful against cancers including non-small cell lung cancer (NSCLC), renal cell carcinoma, mantle cell lymphoma, and endometrial cancers. Further, the compounds and compositions are useful in treating other indications such as rheumatoid arthritis, hamartoma syndromes, transplant rejection, irritable bowel disease (IBD), multiple sclerosis and immunosuppression.

Generally, dosage levels on the order of from about 0.01 mg/kg to about 150 mg/kg of body weight per day are useful in the treatment of the above-indicated conditions, or alternatively about 0.5 mg to about 7 g per patient per day. For example, cancers of the breast, lung, kidney, prostate, blood, liver, ovarian, thyroid, GI tract and lymphoma may be effectively treated by the administration of from about 0.01 to 50 mg of the compound per kilogram of body weight per day, or alternatively about 0.5 mg to about 3.5 g per patient per day.

Dosage levels on the order of from about 0.01 mg/kg to about 150 mg/kg of body weight per day are useful in the treatment of non-small cell lung cancer (NSCLC), renal cell carcinoma, mantle cell lymphoma, and endometrial cancers, or alternatively about 0.5 mg to about 7 g per patient per day. They may be treated by the administration of from about 0.01 to 50 mg of the compound per kilogram of body weight per day, or alternatively about 0.5 mg to about 3.5 g per patient per day.

Dosage levels on the order of from about 0.01 mg/kg to about 150 mg/kg of body weight per day are useful in the treatment of rheumatoid arthritis, hamartoma syndromes, transplant rejection, irritable bowel disease (IBD), multiple sclerosis and immunosuppression, or alternatively about 0.5 mg to about 7 g per patient per day. They may be treated by the administration of from about 0.01 to 50 mg of the compound per kilogram of body weight per day, or alternatively about 0.5 mg to about 3.5 g per patient per day.

It is understood, however, that the specific dose level for any particular patient will depend upon a variety of factors including the age, body weight, general health, sex, diet, time of administration, route of administration, rate of excretion, drug combination and the severity of the particular disease undergoing therapy.

Biochemical Assay for Inhibiton of mTOR Activity:

The ability of compounds to inhibit the mTOR kinase activity was determined in an in vitro immunoprecipitation (IP) kinase assay using recombinant 4E-BP1 as a substrate. The assay determines the ability of compounds to inhibit phosphorylation of 4E-BP1 a well-known physiological substrate of mTOR. The immunocapture mTOR complex from HeLa cells is incubated with various concentrations of compounds and His-tag 4E-BP1 in kinase assay buffer prior to addition of ATP to start the reaction at RT. The reaction is stopped after 30 mins and the phosphorylated His-tag 4E-BP1 is captured on a Nickel-chelate plate overnight at 4° C. The phosphothreonine content of 4E-BP1 is then measured using phospho-4E-BP1 (T37/46) primary antibody and corresponding anti rabbit IgG HRP conjugated, secondary antibody. The secondary antibody has a reporter enzyme (eg. horseradish peroxidase, HRP) covalently attached, such that binding of primary antibody to phosphorylated 4E-BP1 can be determined quantitatively which is equal to the amount secondary antibody bound to it. The amount of secondary antibody can be determined by incubation with an appropriate HRP substrate.

The Stock Reagents used are as Follows:

Cell Lysis Buffer:

40 mM HEPES, pH 7.5 containing 120 mM NaCl, 1mM EDTA, 10 mM sodium pyrophosphate, 10 mM β-glycerophosphate, 50 mM sodium fluoride, 1.5 mM sodium vanadate and 0.3% CHAPS.

Complete mini EDTA-free protease inhibitors (Roche, catalog #11 836 170 001)

HeLa cell pellets (Paragon Bioservices)

Protein G coated plates for immunoprecipitation (Pierce, catalog #15131)

mTOR (aka FRAP) N-19 antibody (Santa Cruz Biotechnology, catalog #sc-1549)

IP Wash Buffer:

50 mM HEPES, pH 7.5 containing 150 mM NaCl

Kinase Buffer:

20 mM HEPES, pH 7.5 containing 10 mM MgCl2, 4 mM MnCl2, 10 mM b-mercaptoethanol and 200 uM sodium vanadate. Make fresh for assay.

Recombinant 4E-BP1 (aka PHAS I) (Calbiochem, catalog #516675)

Dilute 4E-BP1 stock (1 mg/mL) 120 times in kinase assay buffer to obtain a concentration of 0.25 ug/well in 30 uL ATP Solution Prepare 330 uM ATP stock in kinase buffer Ni-chelate Plate (Pierce, catalog #15242)

Antibody Dilution Buffer:

TBST containing 5% skim milk

Phospho-4E-BP1 (T37/46) Antibody:

1:1000 dilution of phospho-4E-BP1 (T37/46) antibody (Cell Signaling Technology, catalog #9459) in antibody dilution buffer Donkey Anti Rabbit IgG, HRP Conjugated 1:10,000 dilution of anti rabbit IgG HRP conjugated (GE Healthcare, Catalog #NA934) in antibody dilution buffer HRP Substrate;

Chemiluminescent reagents (Pierce, catalog #37074)

Assay Protocol:

HeLa cell lysate was prepared in bulk by homogenizing 25 g of cell pellet in 60 mL of cell lysis buffer and then, centrifuged at 12,000 rpm for 30 min. The clear supernatant was transferred to fresh tube, aliquoted, quickly frozen and stored at −80° C. until use.

Protein G coated 96-well plate is washed once with lysis buffer and 50 µL of diluted mTOR antibody is added to each well, and incubated at RT for 30-60 min. Then, 50 µg of HeLa cell lysate was added to each well in 50 µL of lysis buffer and incubated at 4° C. in a cold room on a shaker for 2-3 h. Lysate was removed and the plate was washed with 100 µL of complete lysis buffer for 3 times. The plate was further washed 2 times with 100 µL of high salt wash buffer. Diluted 4E-BP1 (substrate) is added to each well in 30 µL. The compounds were added in various concentrations in 5 µL to each well. The drug concentrations varied from 30 µM to 0.1 µM. The final DMSO concentration was 1%. Only DMSO was added to positive control wells. For negative control wells, no ATP solution was added but instead 15 µL of kinase buffer was added, the reaction was started by addition of ATP in 15 µL to a final concentration of 100 µM to rest of the wells except negative control wells. The reaction was carried out for 30 min at RT. Then, 45 µL of the reaction mixture was transferred to Ni-chelate plate and incubated overnight at 4° C. The plate was washed once with antibody dilution buffer and 50 µL of diluted phospho-4E-BP1 antibody was added to each well, and incubated at RT for 1 h. Then, the plate was washed 4 times with TBST and 50 µL of diluted anti-rabbit secondary antibody was added to each plate, and incubated at RT for 1 h. The plate was washed 4 times with 100 µL of TBST. To each well, 50 µL of Pierce Femto chemiluminescent reagent was added and the chemiluminescence was measured using victor machine.

Comparison of the assay signals obtained in the presence of compound with those of positive and negative controls, allows the degree of inhibiton of phospho-4E-BP1 phosphorylation to be determined over a range of compound concentrations. These inhibiton values were fitted to a sigmoidal dose-response inhibition curve to determine the $IC_{50}$ values (i.e. the concentration of the compound that inhibits phosphorylation of 4E-BP1 by 50%).

The EXAMPLES of this invention inhibited phosphorylation of 4E-BP1 by immunocaptured human mTOR as determined in the above assay with $IC_{50}$ values less than 10.00 µM.

Experimental

The following schemes, intermediates and examples serve to demonstrate how to synthesize compounds of this invention, but in no way limit the invention. Additionally, the following abbreviations are used: Me for methyl, Et for ethyl, iPr or iPr for isopropyl, n-Bu for n-butyl, t-Bu for tert-butyl, Ac for acetyl, Ph for phenyl, 4Cl-Ph or (4Cl)Ph for 4-chlorophenyl, 4Me-Ph or (4Me)Ph for 4-methylphenyl, (p-CH3O)Ph for p-methoxyphenyl, (p-NO2)Ph for p-nitrophenyl, 4Br-Ph or (4Br)Ph for 4-bromophenyl, 2-CF3-Ph or (2CF3)Ph for 2-trifluoromethylphenyl, DMAP for 4-(dimethylamino)pyridine, DCC for 1,3-dicyclohexylcarbodiimide, EDC for 1-(3-dimethylaminopropyl)-3-ethylcarbodiimide hydrochloride, HOBt for 1-hydroxybenzotriazole, HOAt for 1-hydroxy-7-azabenzotriazole, TMP for tetramethylpiperidine, n-BuLi for n-butyllithium, CDI for 1,1'-carbonyldiimidazole, DEAD for diethyl azodicarboxylate, PS-PPh3 for polystyrene triphenylphosphine, DIEA for diisopropylethylamine, DIAD for diisopropyl azodicarboxylate, DBAD for di-tert-butyl azodicarboxylate, HPFC for high performance flash chromatography, rt or RT for room temperature, min for minute, h for hour, Bn for benzyl, and LAH for lithium aluminum hydride.

Accordingly, the following are compounds that are useful as intermediates in the formation of mTOR inhibiting EXAMPLES.

The compounds of Formula I of this invention and the intermediates used in the synthesis of the compounds of this invention were prepared according to the following methods. Method A was used when preparing compounds of Formula I-AA

I-AA as shown below in Scheme 1:

Method A:

Scheme 1

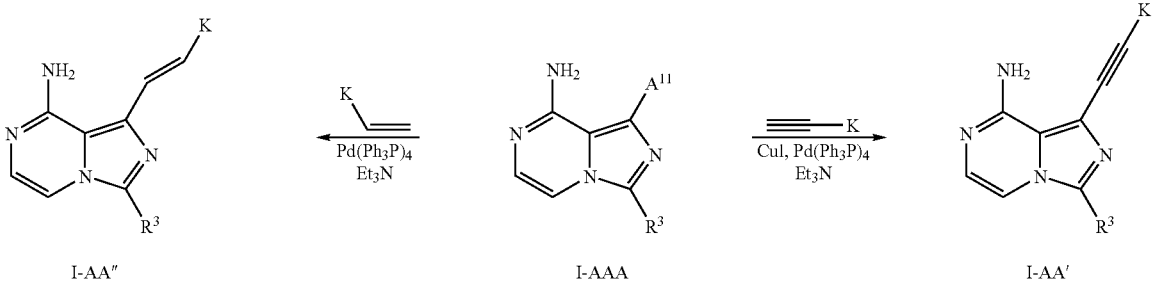

I-AA″          I-AAA          I-AA′ where $Q^1$, K and $R^3$ are as defined previously for compound of Formula I, $A^{11}$=halogen such as Cl, Br, or I.

In a typical preparation of compounds of Formula I-AA', a compound of Formula I-AAA was reacted with a suitable substituted acetylene derivative in a suitable solvent via typical Sonogashirai coupling procedures. Suitable solvents for use in the above process included, but were not limited to, ethers such as tetrahydrofuran (THF), glyme, dioxane, dimethoxyethane, and the like; dimethylformamide (DMF); dimethyl sulfoxide (DMSO); acetonitrile; and chlorinated solvents such as methylene chloride ($CH_2Cl_2$) or chloroform ($CHCl_3$). If desired, mixtures of these solvents were used, however, the preferred solvent was DMF. The above process was carried out at temperatures between about −78° C. and about 120° C. Preferably, the reaction was carried out between 0° C. and about 50° C. The above process to produce compounds of the present invention was preferably carried out at about atmospheric pressure although higher or lower pressures were used if desired. Substantially equimolar amounts of reactants were preferably used although higher or lower amounts were used if desired. Alternatively, compounds of Formula I-AA" were prepared from a compound of Formula I-AAA by reaction with a suitable substituted vinyl derivative in a suitable solvent via typical Heck coupling procedures. Suitable solvents for use in the above process included, but were not limited to, ethers such as tetrahydrofuran (THF), glyme, dioxane, dimethoxyethane, and the like; dimethylformamide (DMF); dimethyl sulfoxide (DMSO); acetonitrile; and chlorinated solvents such as methylene chloride ($CH_2Cl_2$) or chloroform ($CHCl_3$). If desired, mixtures of these solvents may be used, however, the preferred solvent was DMF. The above process can be carried out at temperatures between about −78° C. and about 120° C. Preferably, the reaction was carried out between 20° C. and about 100° C.

The compounds of Formula I-AAA of Scheme 1 were prepared as shown below in Scheme 2.

Scheme 2

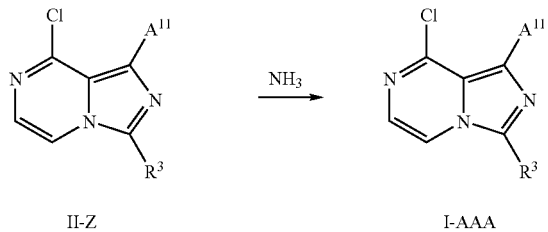

II-Z            I-AAA where $R^3$ is as defined previously for compound of Formula I and $A^{11}$=halogen such as Cl, Br, or I.

In a typical preparation of compounds of Formula I-AAA, compound of Formula II-Z was reacted with ammonia in a suitable solvent. Suitable solvents for use in the above process included, but were not limited to, ethers such as tetrahydrofuran (THF), glyme, and the like; dimethylformamide (DMF); dimethyl sulfoxide (DMSO); acetonitrile; alcohols such as methanol, ethanol, isopropanol, trifluoroethanol, and the like; and chlorinated solvents such as methylene chloride ($CH_2Cl_2$) or chloroform ($CHCl_3$). If desired, mixtures of these solvents were used, however, the preferred solvents were isopropanol and a mixture of THF and isopropanol. The above process was carried out at temperatures between about −78° C. and about 120° C. Preferably, the reaction was carried out between 80° C. and about 120° C. The above process to produce compounds of the present invention was preferably carried in a sealed reaction vessel such as but not limited to a thick walled glass reaction vessel or a stainless steel Parr bomb. An excess amount of the reactant, ammonia, was preferably used.

The compounds of Formula II-Z of Scheme 2 were prepared as shown below in Scheme 3.

Scheme 3

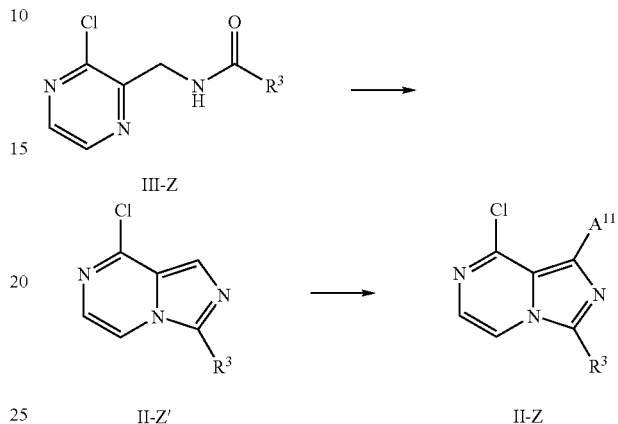

II-Z'            II-Z where $R^3$ is as defined previously for compound of Formula I and $A^{11}$=halogen such as Cl, Br, or I.

In a typical preparation of a compound of Formula II-Z, intermediate III-Z was converted to compound of Formula II-Z'. Intermediate of Formula III-Z was treated with $POCl_3$ in a suitable solvent at a suitable reaction temperature. Suitable solvents for use in the above process included, but were not limited to, ethers such as tetrahydrofuran (THF), glyme, and the like; acetonitrile; and chlorinated solvents such as methylene chloride ($CH_2Cl_2$) or chloroform ($CHCl_3$). If desired, mixtures of these solvents were used. The preferred solvents included methylene chloride and acetonitrile. The above process was carried out at temperatures between about −78° C. and about 120° C. Preferably, the reaction was carried out between 20° C. and about 95° C. The above process to produce compounds of the present invention was preferably carried out at about atmospheric pressure although higher or lower pressures were used if desired. Substantially equimolar amounts of reactants were preferably used although higher or lower amounts were used if desired. In the conversion of compound of Formula III-Z to II-Z', suitable halogenating agent were used, but were not limited to, $Br_2$, $I_2$, $Cl_2$, N-chlorosuccinimide, N-bromosuccinimide, or N-iodosuccinimide. The preferred halogenating agent was N-iodosuccinimide. Suitable solvents for use in the above process included, but were not limited to, ethers such as tetrahydrofuran (THF), glyme, and the like; dimethylformamide (DMF); dimethyl sulfoxide (DMSO); acetonitrile; alcohols such as methanol, ethanol, isopropanol, trifluoroethanol, and the like; and chlorinated solvents such as methylene chloride ($CH_2Cl_2$) or chloroform ($CHCl_3$). If desired, mixtures of these solvents were used, however, the preferred solvent was DMF. The above process was carried out at temperatures between about −78° C. and about 120° C. Preferably, the reaction was carried out between 40° C. and about 75° C. The above process to produce compounds of the present invention was preferably carried out at about atmospheric pressure although higher or lower pressures were used if desired. Substantially equimolar amounts of reactants were preferably used although higher or lower amounts were used if desired.

The compounds of Formula III-Z of Scheme 3 were prepared as shown below in Scheme 4:

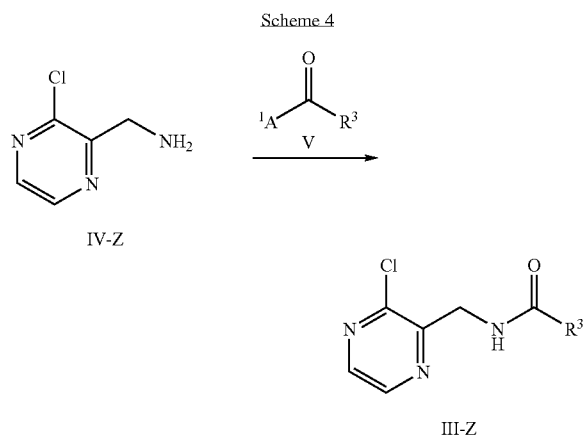

where $R^3$ is as defined previously for compound of Formula I and $A^1$=OH, alkoxy, or a leaving group such as chloro or imidazole.

In a typical preparation, of a compound of Formula III-Z, a compound of Formula IV-Z and compound of Formula V were reacted under suitable amide coupling conditions. Suitable conditions include but are not limited to treating compounds of Formula IV-Z and V (when $A^1$=OH) with coupling reagents such as DCC or EDC in conjunction with DMAP, HOBt, HOAt and the like. Suitable solvents for use in the above process included, but were not limited to, ethers such as tetrahydrofuran (THF), glyme, and the like; dimethylformamide (DMF); dimethyl sulfoxide (DMSO); acetonitrile; halogenated solvents such as chloroform or methylene chloride. If desired, mixtures of these solvents were used, however the preferred solvent was methylene chloride. The above process was carried out at temperatures between about 0° C. and about 80° C. Preferably, the reaction was carried out at about 22° C. The above process to produce compounds of the present invention was preferably carried out at about atmospheric pressure although higher or lower pressures were used if desired. Substantially equimolar amounts of reactants were preferably used although higher or lower amounts were used if desired. Additionally, if compound of Formula IV-Z was a salt or bis-salt, a suitable base was required and included, but was not limited to, diisopropylethylamine or triethylamine. Alternatively, compounds of Formula IV-Z and V (where $A^1$=F, Cl, Br, I) were reacted with bases such as triethylamine or diisopropylethylamine and the like in conjunction with DMAP and the like. Suitable solvents for use in this process included, but were not limited to, ethers such as tetrahydrofuran (THF), glyme, and the like; dimethylformamide (DMF); dimethyl sulfoxide (DMSO); acetonitrile; halogenated solvents such as chloroform or methylene chloride. If desired, mixtures of these solvents were used, however the preferred solvent was methylene chloride. The above process was carried out at temperatures between about −20° C. and about 40° C. Preferably, the reaction was carried out between 0° C. and 25° C. The above process to produce compounds of the present invention was preferably carried out at about atmospheric pressure although higher or lower pressures were used if desired. Substantially equimolar amounts of compounds of Formula IV-Z and V (where $A^1$=F, Cl, Br, I) and base and substochiometric amounts of DMAP were preferably used although higher or lower amounts were used if desired. Additionally, other suitable reaction conditions for the conversion of an amine (compound of Formula IV-Z) to an amide (compound of Formula III-Z) can be found in Larock, R. C. Comprehensive Organic Transformations, 2nd ed.; Wiley and Sons: New York, 1999, pp 1941-1949.

The compounds of Formula IV-Z of Scheme 4 were prepared as shown below in Scheme 5:

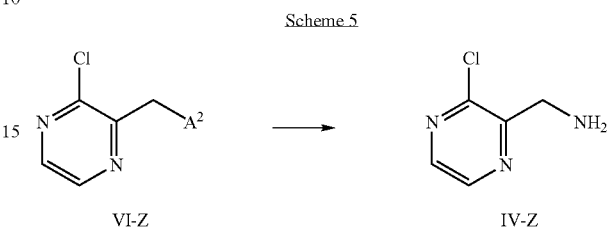

where $A^2$ is phthalimido or $N_3$.

In a typical preparation, of a compound of Formula IV-Z, a compound of Formula VI-Z is reacted under suitable reaction conditions in a suitable solvent. When $A^2$=phthalimido, suitable conditions include treatment of compound of Formula VI-Z with hydrazine in a suitable solvent. Suitable solvents for use in the above process included, but were not limited to, ethers such as tetrahydrofuran (THF), glyme, and the like; dimethylformamide (DMF); dimethyl sulfoxide (DMSO); acetonitrile; halogenated solvents such as chloroform or methylene chloride; alcoholic solvents such as methanol and ethanol. If desired, mixtures of these solvents may be used, however the preferred solvent was ethanol. The above process was carried out at temperatures between about 0° C. and about 80° C. Preferably, the reaction was carried out at about 22° C. The above process to produce compounds of the present invention was preferably carried out at about atmospheric pressure although higher or lower pressures were used if desired. Substantially equimolar amounts of reactants were preferably used although higher or lower amounts were used if desired.

The compounds of Formula VI-Z of Scheme 5 were prepared as shown below in Scheme 6:

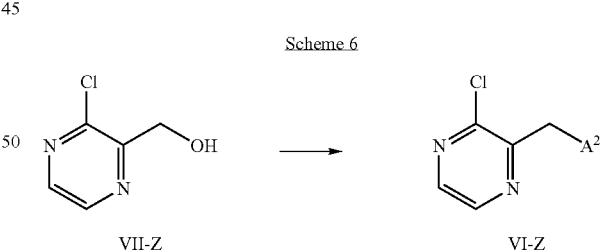

where $A^2$=phthalimido or $N_3$.

In a typical preparation of a compound of Formula VI-Z (when $A^2$=phthalimido), a compound of Formula VII-Z was reacted with a phthalimide under typical Mitsunobu conditions in a suitable solvent in the presence of suitable reactants. Suitable solvents for use in the above process included, but were not limited to, ethers such as tetrahydrofuran (THF), glyme, and the like; dimethylformamide (DMF); dimethyl sulfoxide (DMSO); acetonitrile ($CH_3CN$); chlorinated solvents such as methylene chloride ($CH_2Cl_2$) or chloroform ($CHCl_3$). If desired, mixtures of these solvents were used, however, the preferred solvent was THF. Suitable reactants for use in the above process included, but were not limited to, triphenylphosphine and the like, and an azodicarboxylate (DIAD, DEAD, DBAD). The preferred reactants were triphenylphosphine or resin-bound triphenylphosphine (PS-PPh$_3$) and DIAD. The above process may be carried out at temperatures between about −78° C. and about 100° C. Preferably, the reaction was carried out at about 22° C. The above process to produce compounds of the present invention was preferably carried out at about atmospheric pressure although higher or lower pressures were used if desired. Substantially equimolar amounts of reactants were preferably used although higher or lower amounts were used if desired. Generally, 1.0 or 1.1 equivalents of triphenylphosphine, DIAD and phthalimide was used per equivalent of compound of Formula VII-Z. Additionally, compound of Formula VII-Z can be reacted with Ts$_2$O, Ms$_2$O, Tf$_2$O, TsCl, MsCl, or SOCl$_2$ in which the hydroxy group is converted to a leaving group such as its respective tosylate, mesylate, triflate, or halogen such as chloro and subsequently reacted with an amine equivalent such as NH(Boc)$_2$, phthalimide, potassium phthalimide or sodium azide.

The compounds of Formula VII-Z of Scheme 6 were prepared from 2-chloropyrazine VIII as shown below in Scheme 7:

Scheme 7

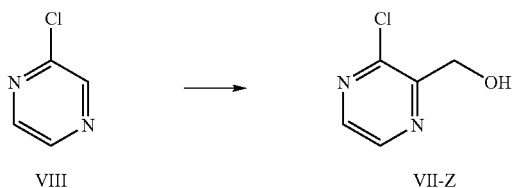

VIII            VII-Z

In a typical preparation, of a compound of Formula VII-Z, a compound of Formula VIII was reacted under suitable reaction conditions in a suitable solvent. Suitable reaction conditions included, but were not limited to, treating compounds of Formula VIII with a base such as lithium tetramethylpiperidide (Li-TMP) followed by treatment with a reagent containing a carbonyl equivalent followed by treatment with a suitable reducing agent. Lithium tetramethylpiperidide may be prepared by reacting tetramethylpiperidine with n-butyllithium at −78° C. and warming up to 0° C. Suitable solvents for use in the above process included, but were not limited to, ethers such as tetrahydrofuran (THF), glyme, and the like. Polar solvents such as hexamethylphosphoramide (HMPA), 1,3-dimethyl-3,4,5,6-tetrahydro-2(1H)-pyrimidinone (DMPU), and the like may be added if necessary. If desired, mixtures of these solvents were used, however, the preferred solvent was THF. Suitable carbonyl equivalent reagents include, but are not limited to, formamides such as DMF or suitable chloroformate such as methyl or ethyl chloroformate. After addition of the suitable carbonyl equivalent reagent, the reaction if charged with a polar protic solvent such as, but not limited to, methanol or ethanol followed by treatment with a suitable reducing agent such as sodium borohydride. The above process may be carried out at temperatures between about −80° C. and about 20° C. Preferably, the reaction was carried out at −78° C. to 0° C. The above process to produce compounds of the present invention was preferably carried out at about atmospheric pressure although higher or lower pressures were used if desired. Substantially equimolar amounts of reactants were preferably used although higher or lower amounts were used if desired.

Both R$^3$ and Q$^1$ in the compounds described herein in some instances contain functional groups that can be further manipulated. It would be appreciated by those skilled in the art that such manipulation of functional groups can be accomplished with key intermediates or with late stage compounds. Such functional group transformations are exemplified in the following Schemes 8-26 as well as in the experimental section but are in no way meant to limit the scope of such transformations. Additionally, the chemistry shown in Schemes 8-26 can also be applied to compounds of I-AAA, II-Z, and II-Z'.

The compounds of Formula I-A (compounds of Formula I-AA where R$^3$=Z–CONR$^{312}$R$^{322}$) were prepared as shown below in Scheme 8:

Scheme 8

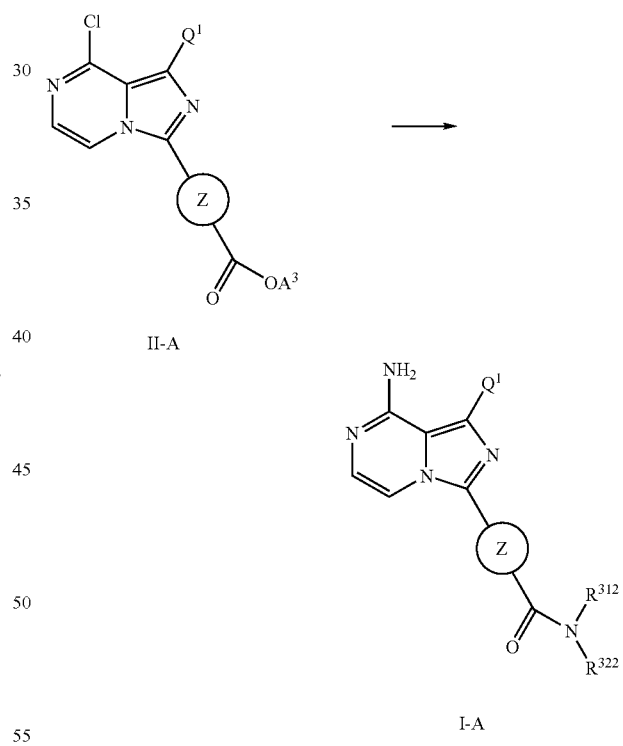

where Q$^1$, R$^{312}$ and R$^{322}$ are as defined previously for compound of Formula I and A$^3$=hydrogen or alkyl such as methyl or ethyl.

In a typical preparation of compound of Formula I-A, when A$^3$=alkyl and R$^{312}$ and R$^{322}$ were both equal to H, reaction of compound of Formula II-A (compounds of Formula II where R$^3$=Z—CO$_2$A$^3$) with ammonia in a suitable solvent, afforded compound of Formula I-A. Suitable solvents for use in the above process included, but were not limited to, ethers such as tetrahydrofuran (THF), glyme, and the like; dimethylformamide (DMF); dimethyl sulfoxide (DMSO); acetonitrile; alcohols such as methanol, ethanol, isopropanol, trifluoroethanol, and the like; and chlorinated solvents such as methylene chloride ($CH_2Cl_2$) or chloroform ($CHCl_3$). If desired, mixtures of these solvents were used, however, the preferred solvents were isopropanol and a mixture of isopropanol/THF. The above process was carried out at temperatures between about −78° C. and about 120° C. Preferably, the reaction was carried out between 80° C. and about 120° C. The above process to produce compounds of the present invention was preferably carried out at about atmospheric pressure although higher or lower pressures were used if desired. Substantially equimolar amounts of reactants were preferably used although higher or lower amounts were used if desired. Additionally, in a typical preparation of compound of Formula I-A, compound of Formula II-A (when $A^3$=H) was reacted with $HNR^{312}R^{322}$ followed by ammonia in a suitable solvent. When $A^3$=H, typical coupling procedures include conversion of $CO_2H$ to COCl via treatment with $SOCl_2$ or oxalyl chloride followed by reaction with $HR^{312}R^{322}$ or treatment of $CO_2H$ and $HR^{312}R^{322}$ with EDC or DCC in conjunction with DMAP, HOBT, or HOAt and the like When $A^3$=alkyl such as methyl or ethyl, treatment of the ester with a pre-reacted mixture of $AlMe_3$ and $HNR^{312}R^{322}$ afforded conversion of $CO_2A^3$ to $CO(NR^{312}R^{322})$. Subsequent treatment with ammonia afforded compounds of Formula I-A.

The compounds of Formula I-A' (compounds of Formula I-AA where $R^3$=Z—$CO_2A^3$) and I-A" (compounds of Formula I-AA where $R^3$=Z—$CO_2H$) were prepared as shown below in Scheme 9:

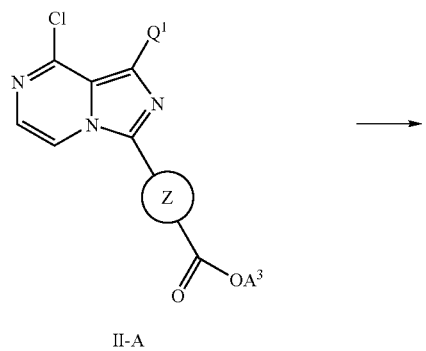

Scheme 9

II-A

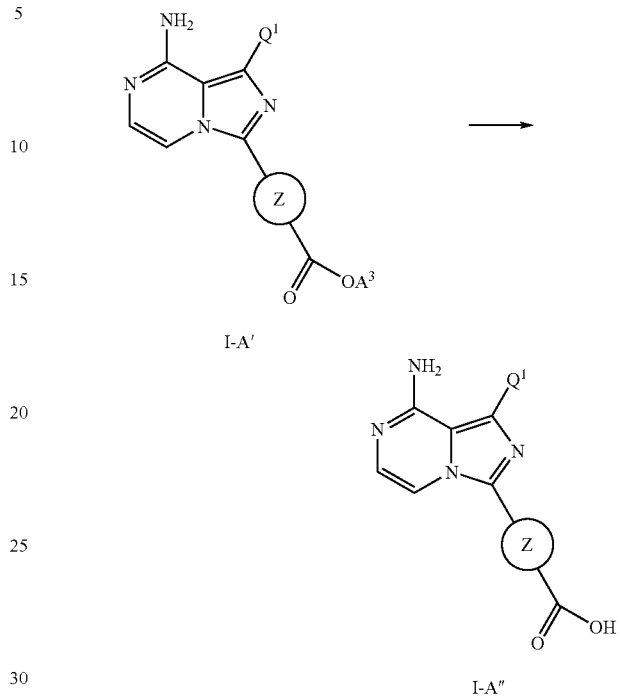

I-A'

I-A"

where $Q^1$ is as defined previously for compounds of Formula I and $A^3$=alkyl such as methyl or ethyl.

In a typical preparation of compound of Formula I-A', compound of Formula II-A was reacted with ammonia in a suitable solvent. Suitable solvents for use in the above process included, but were not limited to, ethers such as tetrahydrofuran (THF), glyme, and the like; dimethylformamide (DMF); dimethyl sulfoxide (DMSO); acetonitrile; alcohols such as methanol, ethanol, isopropanol, trifluoroethanol, and the like; and chlorinated solvents such as methylene chloride ($CH_2Cl_2$) or chloroform ($CHCl_3$). If desired, mixtures of these solvents were used, however, the preferred solvent was isopropanol. The above process was carried out at temperatures between about −78° C. and about 120° C. Preferably, the reaction was carried out between 100° C. and about 120° C. The above process to produce compounds of the present invention was preferably carried out at about atmospheric pressure although higher or lower pressures were used if desired. In most cases, the reactions were run in a sealed tube. Substantially equimolar amounts of reactants were preferably used although higher or lower amounts were used if desired. Typically, an excess of ammonia was used and the reaction was monitored in order to ensure that additional of ammonia to the ester moiety did not occur to an appreciable extent. Additionally, in a typical preparation of compound of Formula I-A", compound of Formula I-A' was reacted under typical saponification conditions such as NaOH in THF/H$_2$O/MeOH. Suitable solvents for use in the above process included, but were not limited to, ethers such as tetrahydrofuran (THF), glyme, and the like; dimethylformamide (DMF); dimethyl sulfoxide (DMSO); acetonitrile; alcohols such as methanol, ethanol, isopropanol, trifluoroethanol, and the like; and chlorinated solvents such as methylene chloride (CH$_2$Cl$_2$) or chloroform (CHCl$_3$). If desired, mixtures of these solvents were used, however, the preferred solvent was a mixture of THF/H$_2$O/MeOH. The above process was carried out at temperatures between about −78° C. and about 120° C. Preferably, the reaction was carried out between rt and about 60° C. The above process to produce compounds of the present invention was preferably carried out at about atmospheric pressure although higher or lower pressures were used if desired. Substantially equimolar amounts of reactants were preferably used although higher or lower amounts were used if desired.

The compounds of Formula II-B (compounds of Formula II where R$^3$=Z—CH$_2$OH) and I-B (compounds of Formula I-AA where R$^3$=Z—CH$_2$OH) were prepared as shown below in Scheme 10:

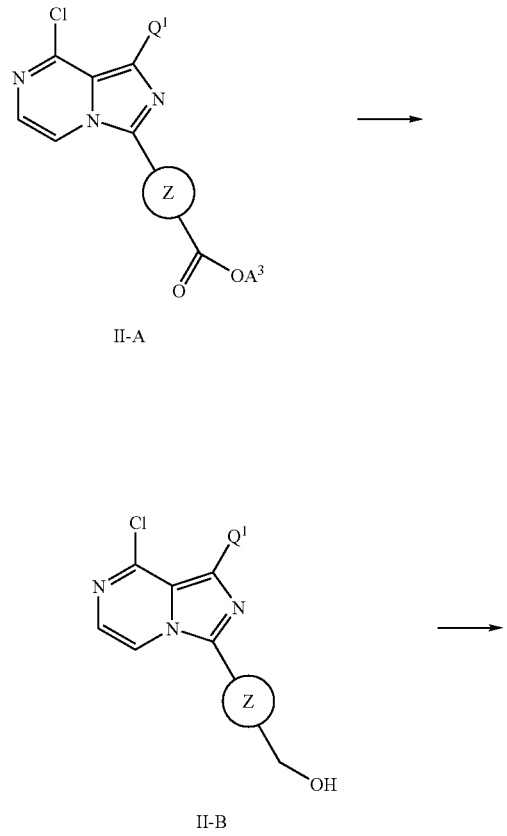

-continued

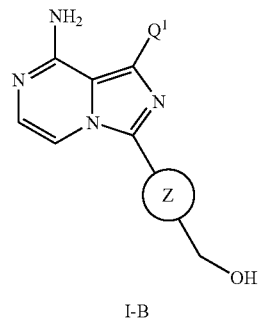

I-B where Q$^1$ is as defined previously for compound of Formula I and A$^3$=hydrogen or alkyl such as methyl or ethyl.

In a typical preparation of compound of Formula I-B, compound of Formula II-A is treated with a suitable reducing agent such as lithium aluminum hydride or diisobutylaluminium hydride in a suitable solvent, such as THF to afford compound of Formula II-B. Suitable solvents for use in the above process included, but were not limited to, ethers such as tetrahydrofuran (THF), glyme, and the like; dimethylformamide (DMF); dimethyl sulfoxide (DMSO); acetonitrile; alcohols such as methanol, ethanol, isopropanol, trifluoroethanol, and the like; and chlorinated solvents such as methylene chloride (CH$_2$Cl$_2$) or chloroform (CHCl$_3$). If desired, mixtures of these solvents were used. The preferred solvent was THF. The above process was carried out at temperatures between about −78° C. and about 120° C. Preferably, the reaction was carried out at approximately −60° C. The above process to produce compounds of the present invention was preferably carried out at about atmospheric pressure although higher or lower pressures were used if desired. Substantially equimolar amounts of reactants were preferably used although higher or lower amounts were used if desired. Subsequent treatment of compound of Formula II-B under previously described ammonolysis conditions (ammonia in isopropanol in a sealed tube at 120° C.), afforded compound of Formula I-B.

The compounds of Formula II-C (compounds of Formula II where R$^3$=Z—CH$_2$A$^4$), II-D (compounds of Formula II where R$^3$=Z—CH$_2$A$^5$(R$^{313}$)(R$^{323}$)$_{aa}$), I-B (compounds of Formula I-AA where R$^3$=Z—CH$_2$OH) and I-C (compounds of Formula I-AA where R$^3$=Z—CH$_2$A$^5$(R$^{313}$)(R$^{323}$)$_{aa}$) were prepared as shown below in Scheme 11:

Scheme 11

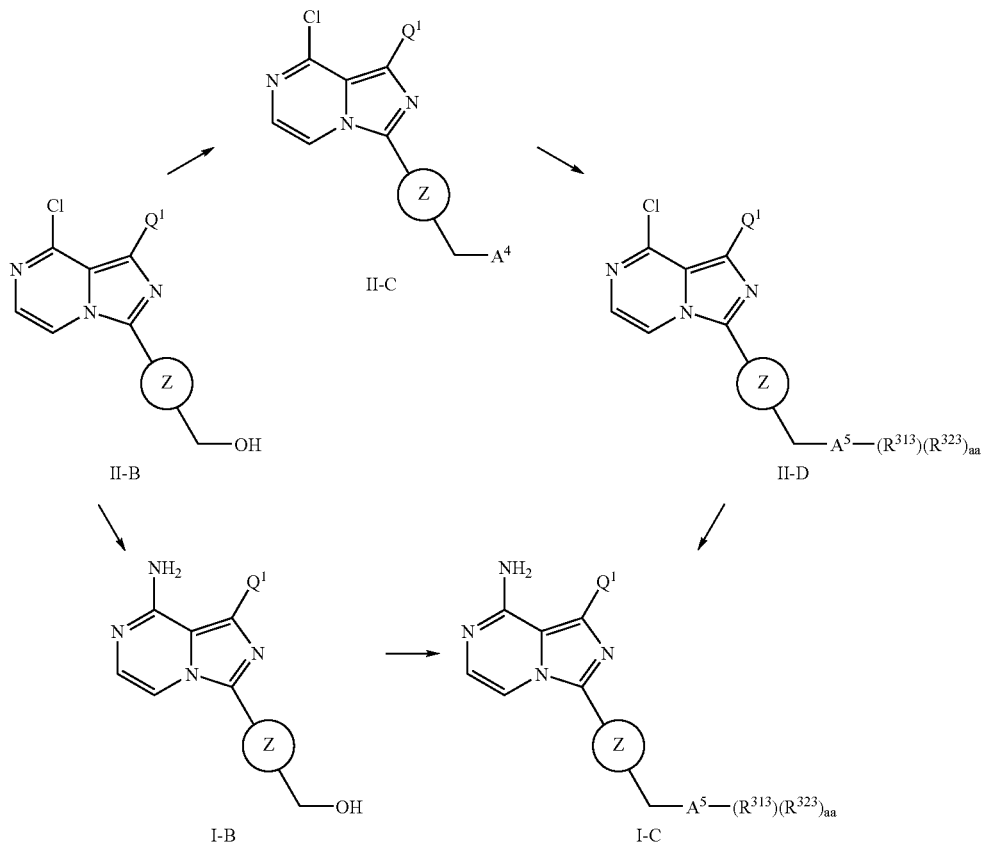

where $Q^1$, $R^{313}$, and $R^{323}$ are as defined previously for compound of Formula I; $A^4$=suitable leaving group such as OTs, OMs, OTf, or halo such as chloro, bromo, or iodo and $A^5$=N, O or S.

In a typical preparation of compound of Formula I-C, the hydroxy group of compound of Formula II-B was converted to a suitable leaving group, $A^4$, such as Cl or OTs, OMs, or OTf, by reaction with $SOCl_2$ or $Ts_2O$, $Ms_2O$, or $Tf_2O$ to afford compound of Formula II-C. Reaction of compound of Formula II-C with $HA^5(R^{313})(R^{323})_{aa}$ afforded compound of Formula II-D. Subsequent reaction of compound of Formula II-D under previously described ammonolysis conditions afforded compound of Formula I-C. Additionally, compound of Formula II-B was converted to compound of Formula I-B as described previously in Scheme 10. Further conversion of compound of Formula I-B to compound of Formula I-C was accomplished by following the previously described conditions for the conversion of compound of Formula II-B to compound of Formula II-C and the further conversion of compound of Formula II-C to compound of Formula II-D (in the net conversion of OH to $A^5(R^{313})(R^{323})_{aa}$). Furthermore, compound of Formula II-B can be directly converted to compound of Formula II-D by treating compound of Formula II-B with various alkylating agent or with phenols via the Mitsunobu reaction to afford compounds Formula II-D (compounds of Formula II where $R^3=CH_2-Z-A^5(R^{313})(R^{323})_{aa}$) in which $A^5$=O, aa=0, and $R^{313}$=alkyl or aryl).

The compounds of Formula I-C' (compounds of Formula I-AA where $R^3=Z-CH_2-A^2$), I-C'' (compounds of Formula I-AA where $R^3=Z-CH_2-NH_2$), and I-C''' (compounds of Formula I-AA where $R^3=Z-CH_2-N(R^{313})(R^{323})$) were prepared as shown below in Scheme 12:

Scheme 12

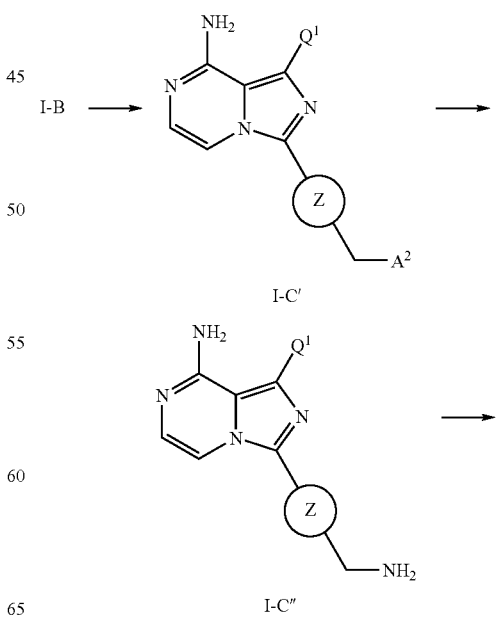

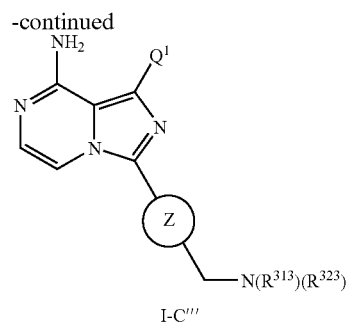

I-C''' where $Q^1$, $R^{313}$, and $R^{323}$ are as defined previously for compound of Formula I and $A^2$=phthalimido or $N_3$.

In a typical preparation of compounds of Formula I-C', I-C", and I-C''', the hydroxy group of compound of Formula I-B was converted to $A^2$, following the procedures as described in Scheme 11 for the conversion of compound of Formula II-B to compound of Formula II-C. Reaction of compound of Formula I-C' under conditions also described in Scheme 11 afforded compound of Formula I-C". Reaction of compound of Formula I-C" with, but not limited to various alkylating agents, various aldehydes/ketones under reductive animation conditions, various acylating agents such as acetic anhydride, benzoyl chlorides, or with carboxylic acids in the presence of EDC or DCC with HOBT or HOAT, or with sulphonylating agents such as $Ts_2O$ or $MeSO_2Cl$ afforded compounds of Formula I-C'''. For example, in a typical preparation of compounds of Formula I-C''', a compound of Formula I-C" is treated with a suitable acylating agent in the presence of a suitable base in a suitable solvent. Suitable solvents for use in the above process included, but were not limited to, ethers such as tetrahydrofuran (THF), glyme, and the like; and chlorinated solvents such as methylene chloride ($CH_2Cl_2$) or chloroform ($CHCl_3$). If desired, mixtures of these solvents were used, however, the preferred solvent was chloroform. Suitable bases for use in the above process included, but were not limited to, trialkylamines such as diisopropylethylamine, triethylamine, or resin bound trialkylamines such as PS-DIEA. The preferred base was PS-DIEA. In the case where the suitable acylating agent was acetic anhydride, the conversion of compound of Formula I-C" to compound of Formula I-C''' where $R^{313}$=H and $R^{323}$=$COCH_3$ was accomplished. The above process was carried out at temperatures between about −78° C. and about 120° C. Preferably, the reaction was carried out between 0° C. and about 20° C. The above process to produce compounds of the present invention was preferably carried out at about atmospheric pressure although higher or lower pressures were used if desired. Substantially equimolar amounts of reactants were preferably used although higher or lower amounts were used if desired.

The compounds of Formula I-D (compounds of Formula I-AA where $R^3$=$(CH_2)_n$—$Z^2$—H and $Z^2$ is a heterocyclyl ring containing a nitrogen atom connected to H) and I-E (compounds of Formula I-AA where $R^3$=$(CH_2)_n$—$Z^2$—$R^{31}$ and $Z^2$ is a heterocyclyl ring containing a nitrogen atom connected to $R^{31}$) were prepared as shown below in Scheme 13:

Scheme 13

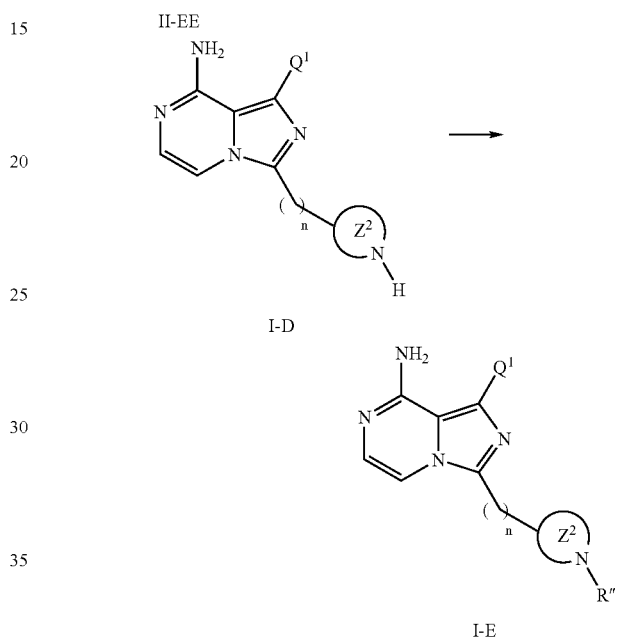

where $Q^1$ and $R^{31}$ are as defined previously for compound of Formula I, $G^{99a}$ is C(=O)$A^6$ or $CO_2A^6$, n 32 0-5, and $A^6$=alkyl, aryl, or aralkyl.

In a typical preparation of compound of Formula I-E, compound of Formula II-E is treated with suitable reagents capable of converting N-$G^{99a}$ to N—H and therefore afford compound of Formula I-D. For example, treatment of compound of Formula II-E (when $G^{99a}$ is equal to $CO_2Bn$) under previously described ammonolysis conditions followed by treatment with concentrated HCl and a suitable basic workup, affords compound of Formula I-D. Compound of Formula I-D can be subjected to various conditions including but not limited to reductive animations, alkylations and ar(hetar)ylations, and acylations to afford amides, ureas, guanidines, carbamates, thiocarbamates, sulphonamides, and variously substituted nitrogen adducts to afford the net conversion of NH to $NR^2$.

The compounds of Formula II-G (compounds of Formula II where $R^3$=$Z^3$—OH), II-H (compounds of Formula II where $R^3$=Z-$A^5(R^{313})(R323)_{aa}$) , I-F (compounds of Formula I-AA where $R^3$=Z—OH), and I-G (compounds of Formula I-AA where $R^3$=Z-$A^5(R^{313})(^{323})_{aa}$) were prepared as shown below in Scheme 14:

Scheme 14

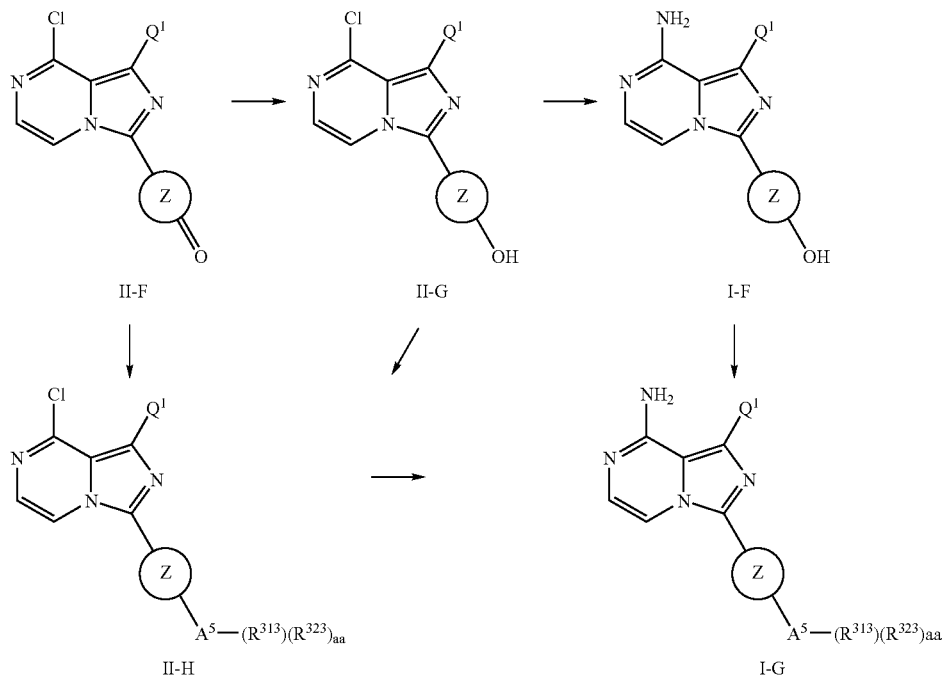

where $Q^1$, $R^{313}$, and $R^{323}$ are as defined previously for compound of Formula I; aa=0 or 1; and $A^5$=N, O or S.

In a typical preparation of compound of Formula I-F and I-G, the following transformations occurred: Compound of Formula II-F was reduced with a suitable reducing agent that would selectively reduce the carbonyl system over the unsaturated $Q^1$ group, in a suitable solvent, such as sodium borohydride in methanol to afford compound of Formula II-G. Compound of Formula II-G was subjected to previously described ammonolysis conditions to afford compound of Formula I-F. Additionally, compounds of Formula II-F can be reacted with various amines under reductive animation conditions (NaBH$_3$CN or NaBH(OAc)$_3$ with HA$^5$(R$^{313}$)(R$^{323}$)$_{aa}$ where d=0, A$^5$=N, and R$^{313}$ and R$^{323}$ are as previously described for compound of Formula I) to afford compounds of Formula II-H where d=0, A$^5$=N, and R$^{313}$ and R$^{323}$ are as previously described for compound of Formula I. Subsequent reaction of compounds of Formula II-H (compounds of Formula II where R$^3$=Z-A$^5$(R$^{313}$)(R$^{323}$)$_{aa}$ where d=0, A$^5$=N, and R$^{313}$ and R$^{323}$ are as previously described for compound of Formula I) with previously described ammonolysis conditions afforded compounds of Formula I-G. Furthermore, compounds of Formula II-H from II-G and I-G from I-F can be synthesized according to the conditions described in Scheme 11 for the transformations of II-B to II-D and I-B to I-C, respectively.

The compounds of Formula I-L (compounds of Formula I-AA where R$^3$=Z—NR$^{313}$R$^{323}$) were prepared as shown below in Scheme 15:

Scheme 15

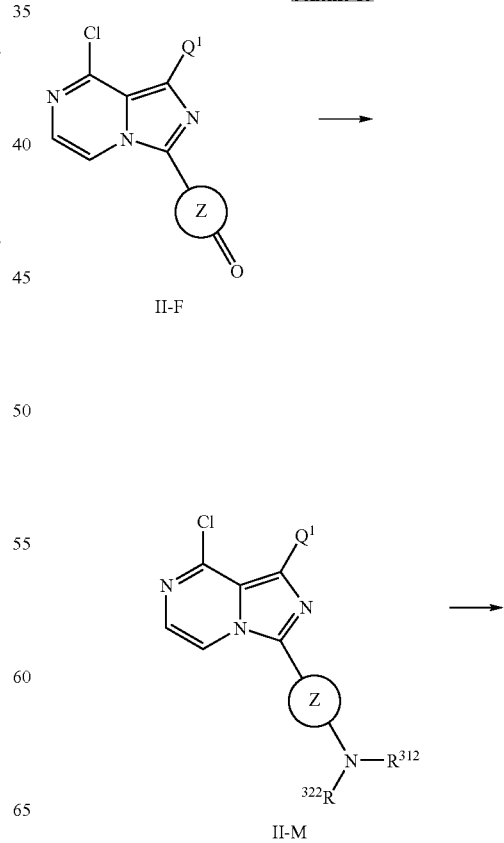

-continued

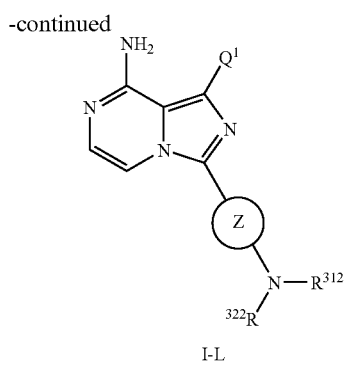

I-L where $Q^1$, $R^{312}$ and $R^{322}$ are as defined previously for compound of Formula I.

Compounds of Formula II-F (compounds of Formula II where $R^3$=Z=O) were treated under typical reductive amination conditions, involving a suitable amine, $HNR^{312}R^{322}$ and a suitable reducing agent, such as but not limited to, $NaBH(OAc)_3$ or $NaBH(CN)_3$, affording compound of Formula II-M (compounds of Formula II where $R^3$=Z—$NR^{312}R^{322}$). Compound of Formula II-M (compounds of Formula II where $R^3$=Z—$NR^{312}R^{322}$) was treated under ammonolysis conditions, ammonia in isopropanol in a stainless steel bomb at 110° C., to afford compound of Formula I-L (compounds of Formula I-AA where $R^3$=Z—$NR^{312}R^{322}$).

The compounds of Formula I-O (compounds of Formula I where $R^3$=$Z^3$—OH($G^{11}$)) were prepared as shown below in Scheme 16:

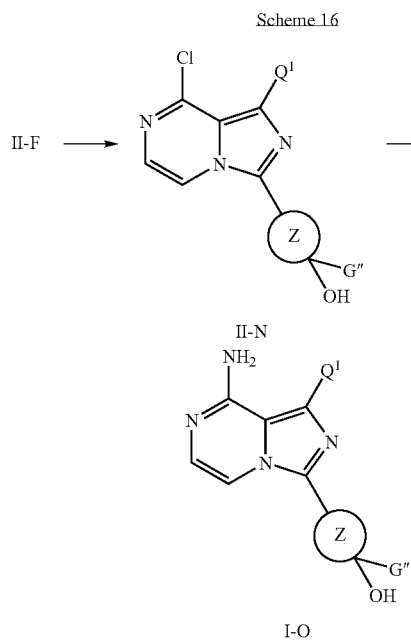

where $Q^1$ and $G^{11}$ are as defined previously for compound of Formula I.

In a typical preparation of compounds of Formula I-O (compounds of Formula I where $R^3$=Z—OH($G^{11}$)), the ketone moiety of compound of Formula II-F (compounds of Formula II where $R^3$=Z=O) was reacted with a suitable nucleophilic reagent such as MeMgBr or MeLi in a suitable solvent such as THF to afford compound of Formula II-N (compounds of Formula II where $R^3$=Z—OH($G^{11}$)). Compound of Formula II-N (compounds of Formula II where $R^3$=Z—OH($G^{11}$)) was reacted under ammonolysis conditions, ammonia in isopropanol in a stainless steel bomb at 110° C., to afford compound of Formula I-O (compounds of Formula I where $R^3$=Z—OH($G^{11}$)).

The compounds of Formula I-R (compounds of Formula I-AA where $R^3$=aryl or heteroaryl) were prepared as shown below in Scheme 17:

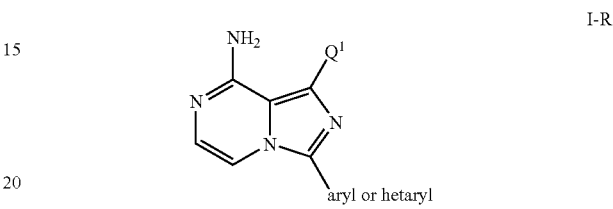

Scheme 17

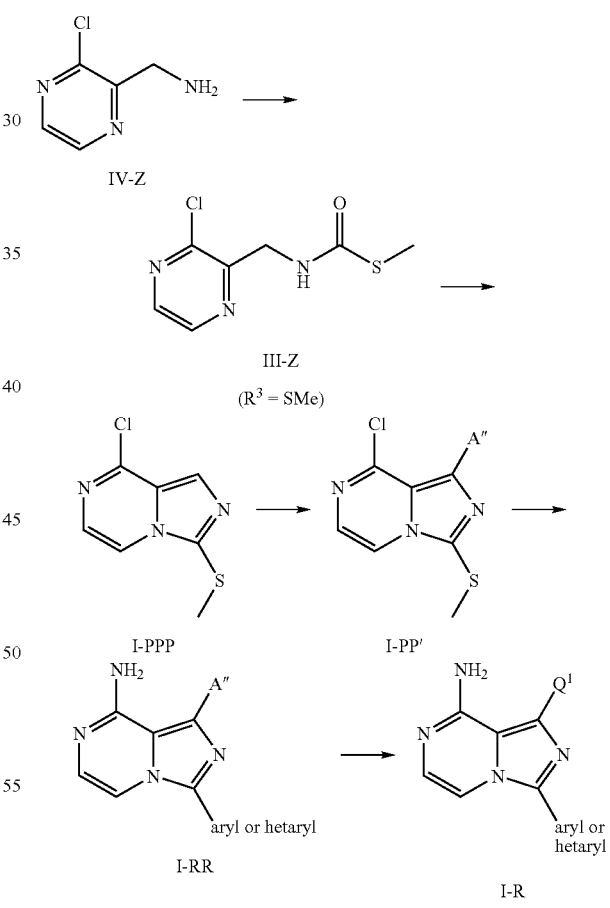

A compound of Formula IV-Z can be reacted with methyl chlorothiolformate in the presence of a base in a suitable solvent to afford a compound of formula III-Z ($R^3$=SMe). Suitable solvents for this process included, but were not limited to ethers such as tetrahydrofuran (THF), glyme, dioxane, dimethoxyethane, and the like; dimethylformamide (DMF)

and chlorinated solvents such as methylene chloride ($CH_2Cl_2$) or chloroform ($CHCl_3$). If desired, mixtures of these solvents were used, however, the preferred solvent was methylene chloride. The above process was carried out at temperatures between about −78° C. and about 120° C. Preferably, the reaction was carried out between 0° C. and 50° C. The above process to produce compounds of the present invention was preferably carried out at about atmospheric pressure although higher or lower pressures were used if desired. Substantially equimolar amounts of reactants were preferably used although higher or lower amounts were used if desired. The conversion of compounds of Formula III-Z ($R^3$=SMe) into compounds of Formula I-PP' was conducted using procedures described for the related conversions in Scheme 3.

The conversion of compounds of Formula I-PP' to compounds of Formula I-RR may be accomplished by reaction with a boronic acid ester using so-called "Liebeskind-Srogl" conditions such as those described in *Organic Letters,* (2002), 4(6), 979 or *Synlett,* (2002), (3), 447. Such reactions can be performed selectively at the thiomethyl group even in the presence of halogen substituents such as iodo or bromo.

A compound of Formula I-AB is equal to compound of Formula I wherein $X_1$=CH, $X_2$, $X_4$ and $X_5$=N, and $X_3$, $X_6$ and $X_7$=C; $Q^1$ is as defined for a compound of Formula I; $R^3$ is $C_{0-10}$alkyl, cyclo$C_{3-10}$alkyl, aminomethylcyclo$C_{3-10}$alkyl, bicyclo$C_{5-10}$alkyl, aryl, heteroaryl, aralkyl, heteroaralkyl, heterocyclyl, heterobicyclo$C_{5-10}$alkyl, spiroalkyl, or heterospiroalkyl, any of which is optionally substituted by one or more independent $G^{11}$ substituents; and $G^{11}$ is as defined for a compound of Formula I:

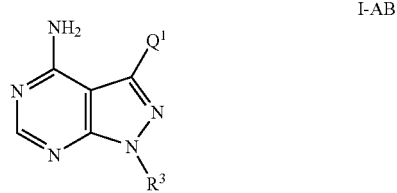

I-AB

Method AB was used when preparing compounds of Formula I-AB as shown below in Scheme 18:

Method AB:

Scheme 18

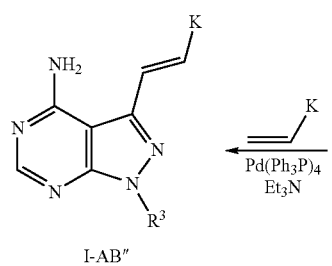

I-AB''

-continued

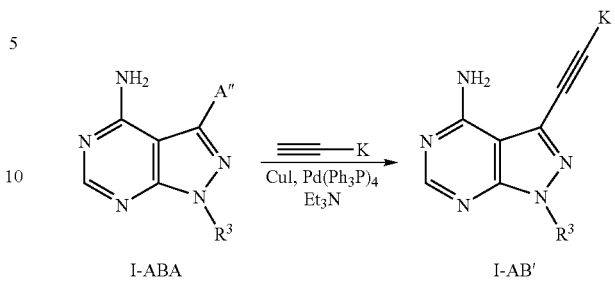

where $Q^1$, K and $R^3$ are as defined previously for compound of Formula I, $A^{11}$=halogen such as Cl, Br, or I.

In a typical preparation of compounds of Formula I-AB', a compound of Formula I-ABA may be reacted with a suitable substituted acetylene derivative in a suitable solvent via typical Sonogashirai coupling procedures. Suitable solvents for use in the above process include, but are not limited to, ethers such as tetrahydrofuran (THF), glyme, dioxane, dimethoxyethane, and the like; dimethylformamide (DMF); dimethyl sulfoxide (DMSO); acetonitrile; and chlorinated solvents such as methylene chloride ($CH_2Cl_2$) or chloroform ($CHCl_3$). If desired, mixtures of these solvents may be used, however, the preferred solvent is DMF. The above process may be carried out at temperatures between about −78° C. and about 120° C. Preferably, the reaction is carried out between 0° C. and about 50° C. The above process to produce compounds of the present invention may be preferably carried out at about atmospheric pressure although higher or lower pressures can be used if desired. Substantially equimolar amounts of reactants are preferably used although higher or lower amounts can be used if desired. Alternatively, compounds of Formula I-AB" may be prepared from a compound of Formula I-ABA by reaction with suitable substituted vinyl derivatives in a suitable solvent via typical Heck coupling procedures. Suitable solvents for use in the above process include, but are not limited to, ethers such as tetrahydrofuran (THF), glyme, dioxane, dimethoxyethane, and the like; dimethylformamide (DMF); dimethyl sulfoxide (DMSO); acetonitrile; and chlorinated solvents such as methylene chloride ($CH_2Cl_2$) or chloroform ($CHCl_3$). If desired, mixtures of these solvents may be used, however, the preferred solvent is DMF. The above process can be carried out at temperatures between about −78° C. and about 120° C. Preferably, the reaction is carried out between 20° C. and about 100° C.

The compounds of Formula I-ABA wherein $R^3$ is $C_{1-10}$alkyl, cyclo$C_{3-10}$alkyl, bicyclo$C_{5-10}$alkyl, aralkyl, heteroaralkyl, heterocyclyl, heterobicyclo$C_{5-10}$alkyl, spiroalkyl, or heterospiroalkyl, any of which is optionally substituted by one or more independent $G^{11}$ substituents, of Scheme 18 were prepared as shown below in Scheme 19:

Scheme 19

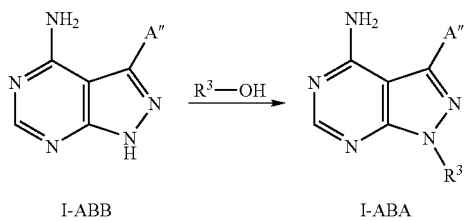

I-ABB  I-ABA where $R^3$ is $C_{1-10}$alkyl, cyclo$C_{3-10}$alkyl, bicyclo$C_{5-10}$alkyl, aralkyl, heteroaralkyl, heterocyclyl, heterobicyclo$C_{5-10}$alkyl, spiroalkyl, or heterospiroalkyl, any of which is optionally substituted by one or more independent $G^{11}$ substituents; $G^{11}$ is as defined previously for compound of Formula I, and $A^{11}$=halogen such as Cl, Br, or I.

In a typical preparation of a compound of Formula I-ABA, a compound of Formula I-ABB was reacted with an alcohol $R^3$—OH under typical Mitsunobu conditions in a suitable solvent in the presence of suitable reactants. Suitable solvents for use in the above process included, but were not limited to, ethers such as tetrahydrofuran (THF), glyme, and the like; dimethylformamide (DMF); dimethyl sulfoxide (DMSO); acetonitrile ($CH_3CN$); chlorinated solvents such as methylene chloride ($CH_2Cl_2$) or chloroform ($CHCl_3$). If desired, mixtures of these solvents were used, however, the preferred solvent was THF. Suitable reactants for use in the above process included, but were not limited to, triphenylphosphine and the like, and an azodicarboxylate (DIAD, DEAD, DBAD). The preferred reactants were triphenylphosphine or resin-bound triphenylphosphine and DIAD. The above process may be carried out at temperatures between about –78° C. and about 100° C. Preferably, the reaction was carried out between about 0° C. and 25° C. The above process to produce compounds of the present invention was preferably carried out at about atmospheric pressure although higher or lower pressures were used if desired. Substantially equimolar amounts of reactants were preferably used although higher or lower amounts were used if desired. Generally, one equivalent of triphenylphosphine, DIAD, and $R^3$—OH was used per equivalent of compound of Formula I-ABB.

Alternatively, the compounds of Formula I-ABA may be prepared by alkylating compounds of Formula I-ABB with an alkylating agent $R^3$-LG, wherein LG is a leaving group including, but not limited to, chloride, bromide, iodide, tosylate, mesylate, trifluoromethanesulfonate, under typical alkylation conditions known to someone skilled in the art.

Preferably, in compounds of Formula I-ABB, $A^{11}$=Br and I. These compounds are known ($A^{11}$=I: H. B. Cottam et al., *J. Med. Chem.* 1993, 36(22), 3424-3430; $A^{11}$=Br: T. S. Leonova et al., *Khim. Geterotsikl. Soedin.* 1982, (7), 982-984).

Compound of Formula I-AC is equal to compound of Formula I wherein $X_1$ and $X_5$=CH, $X_2$ and $X_4$=N, and $X_3$, $X_6$ and $X_7$=C; $Q^1$ is as defined for a compound of Formula I; $R^3$ is $C_{0-10}$alkyl, cyclo$C_{3-10}$alkyl, bicyclo$C_{5-10}$alkyl, aryl, heteroaryl, aralkyl, heteroaralkyl, heterocyclyl, heterobicyclo$C_{5-10}$alkyl, spiroalkyl, or heterospiroalkyl, any of which is optionally substituted by one or more independent $G^{11}$ substituents; and $G^{11}$ is as defined for a compound of Formula I:

I-AC

Method AC was used when preparing compounds of Formula I-AC as shown below in Scheme 20:

Method AC:

Scheme 20

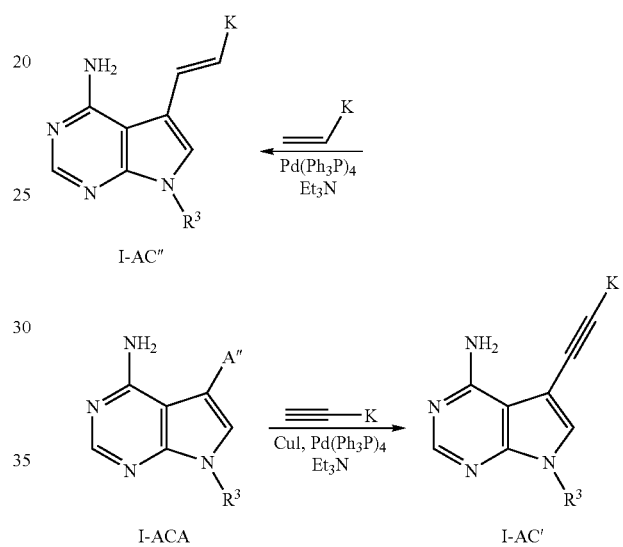

where $Q^1$, K and $R^3$ are as defined previously for compound of Formula I, $A^{11}$=halogen such as Cl, Br, or I.

In a typical preparation of compounds of Formula I-AC', a compound of Formula I-ACA may be reacted with a suitable substituted acetylene derivative in a suitable solvent via typical Sonogashirai coupling procedures. Suitable solvents for use in the above process include, but are not limited to, ethers such as tetrahydrofuran (THF), glyme, dioxane, dimethoxyethane, and the like; dimethylformamide (DMF); dimethyl sulfoxide (DMSO); acetonitrile; and chlorinated solvents such as methylene chloride ($CH_2Cl_2$) or chloroform ($CHCl_3$). If desired, mixtures of these solvents may be used, however, the preferred solvent is DMF. The above process may be carried out at temperatures between about –78° C. and about 120° C. Preferably, the reaction is carried out between 0° C. and about 50° C. The above process to produce compounds of the present invention may be preferably carried out at about atmospheric pressure although higher or lower pressures can be used if desired. Substantially equimolar amounts of reactants are preferably used although higher or lower amounts can be used if desired. Alternatively, compounds of Formula I-AC'' may be prepared from a compound of Formula I-ACA by reaction with suitable substituted vinyl derivatives in a suitable solvent via typical Heck coupling procedures. Suitable solvents for use in the above process include, but are not limited to, ethers such as tetrahydrofuran (THF), glyme, dioxane, dimethoxyethane, and the like; dimethylformamide (DMF); dimethyl sulfoxide (DMSO); acetonitrile; and chlorinated solvents such as methylene chloride ($CH_2Cl_2$) or chloroform ($CHCl_3$). If desired, mixtures of these solvents may be used, however, the preferred solvent is DMF. The above process can be carried out at temperatures between about −78° C. and about 120° C. Preferably, the reaction is carried out between 20° C. and about 100° C.

The compounds of Formula I-ACA of Scheme 20 were prepared as shown below in Scheme 21:

Scheme 21

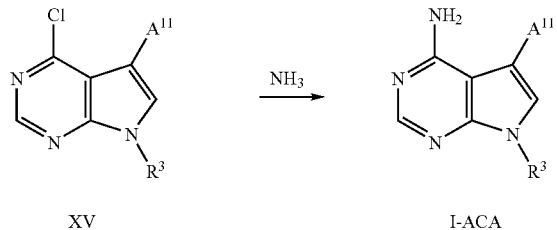

XV    I-ACA where $R^3$ is as defined previously for compound of Formula I-AC, and $A^{11}$=halogen such as Cl, Br, or I.

In a typical preparation of compounds of Formula I-ACA, compound of Formula XV was reacted with ammonia in a suitable solvent. Suitable solvents for use in the above process included, but were not limited to, ethers such as tetrahydrofuran (THF), glyme, and the like; dimethylformamide (DMF); dimethyl sulfoxide (DMSO); acetonitrile; alcohols such as methanol, ethanol, isopropanol, trifluoroethanol, and the like; and chlorinated solvents such as methylene chloride ($CH_2Cl_2$) or chloroform ($CHCl_3$). If desired, mixtures of these solvents were used, however, the preferred solvent was isopropanol. The above process was carried out at temperatures between about −78° C. and about 120° C. Preferably, the reaction was carried out between 80° C. and about 100° C. The above process to produce compounds of the present invention was preferably carried out in a glass pressure tube or a stainless steel reactor. Preferably, an excess of ammonia was used.

The compounds of Formula XVA (=compounds of Formula XV of Scheme 21 wherein $R^3$ is $C_{1-10}$alkyl, $cycloC_{3-10}$alkyl, $bicycloC_{5-10}$alkyl, aralkyl, heteroaralkyl, heterocyclyl, $heterobicycloCs_{5-10}$alkyl, spiroalkyl, or heterospiroalkyl, any of which is optionally substituted by one or more independent $G^{11}$ substituents) were prepared as shown below in Scheme 22:

Scheme 22

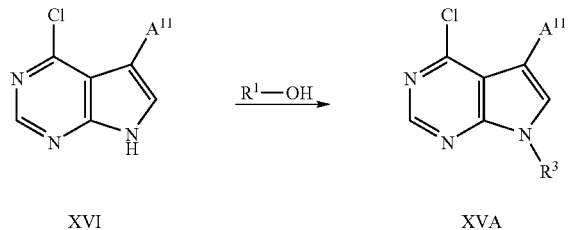

XVI    XVA where $R^3$ is $C_{1-10}$alkyl, $cycloC_{3-10}$alkyl, $bicycloC_{5-10}$alkyl, aralkyl, heteroaralkyl, heterocyclyl, $heterobicycloC_{5-10}$alkyl, spiroalkyl, or heterospiroalkyl, any of which is optionally substituted by one or more independent $G^{11}$ substituents; $G^{11}$ is as defined previously for compound of Formula I; and $A^{11}$=halogen such as Cl, Br, or I.

In a typical preparation of a compound of Formula XVA, a compound of Formula XVI was reacted with an alcohol $R^3$—OH under typical Mitsunobu conditions in a suitable solvent in the presence of suitable reactants. Suitable solvents for use in the above process included, but were not limited to, ethers such as tetrahydrofuran (THF), glyme, and the like; dimethylformamide (DMF); dimethyl sulfoxide (DMSO); acetonitrile ($CH_3CN$); chlorinated solvents such as methylene chloride ($CH_2Cl_2$) or chloroform ($CHCl_3$). If desired, mixtures of these solvents were used, however, the preferred solvent was THF. Suitable reactants for use in the above process included, but were not limited to, triphenylphosphine and the like, and an azodicarboxylate (DIAD, DEAD, DBAD). The preferred reactants were triphenylphosphine or resin-bound triphenylphosphine and DIAD. The above process may be carried out at temperatures between about −78° C. and about 100° C. Preferably, the reaction was carried out between about 0° C. and 25° C. The above process to produce compounds of the present invention was preferably carried out at about atmospheric pressure although higher or lower pressures were used if desired. Substantially equimolar amounts of reactants were preferably used although higher or lower amounts were used if desired. Generally, one equivalent of triphenylphosphine, DLAD, and $R^3$—OH was used per equivalent of compound of Formula XVI.

Alternatively, the compounds of Formula XVA may be prepared by alkylating compounds of Formula XVI with an alkylating agent $R^3$-LG, wherein LG is a leaving group including, but not limited to, chloride, bromide, iodide, tosylate, mesylate, trifluoromethanesulfonate, under typical alkylation conditions known to someone skilled in the art.

The compounds of Formula XVB (=compounds of Formula XV of Scheme 21 wherein $R^3$ is aryl or heteroaryl, optionally substituted by one or more independent $G^{11}$ substituents) were prepared as shown below in Scheme 23:

Scheme 23

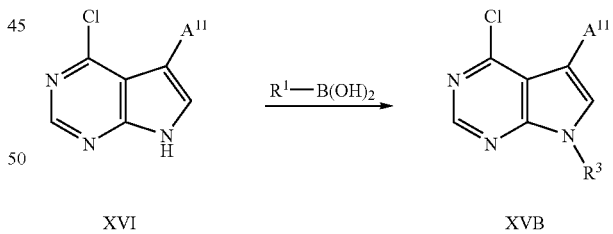

XVI    XVB where $R^3$ is aryl or heteroaryl, optionally substituted by one or more independent $G^{11}$ substituents, $G^{11}$ is as defined previously for compound of Formula I; and $A^{11}$=halogen such as Cl, Br, or I.

In a typical preparation of compounds of Formula XVB, compound of Formula XVI was reacted with a suitable boronic acid of Formula $R^3$—$B(OH)_2$ in a suitable solvent via typical copper(II)-mediated coupling procedures. Suitable solvents for use in the above process included, but were not limited to, ethers such as tetrahydrofuran (THF), glyme, 1,4- dioxane, and the like; dimethylformamide (DMF); N-methylpyrrolidinone (NMP); chlorinated solvents such as methylene chloride ($CH_2Cl_2$). If desired, mixtures of these solvents were used, however, the preferred solvent was methylene chloride ($CH_2Cl_2$). Suitable reactants for use in the above process included, but were not limited to, copper(II) acetate ($Cu(OAc)_2$), copper(II) triflate ($Cu(OTf)_2$), and the like, and a base (pyridine, and the like). The preferred reactants were $Cu(OAc)_2$ and pyridine. The above process to produce compounds of the present invention was preferably carried out at about atmospheric pressure under air, although higher or lower pressures could be used if desired. Preferably, the reaction was carried out at about 22° C. Generally, 1.5eq. of copper(II) acetate, 2eq. of pyridine, and 2eq. of boronic acid of Formula $R^3$—$B(OH)_2$ were used per equivalent of compound of Formula XVI.

All compounds of Formula XVI are known in the literature ($A^{11}$=I: L. B. Townsend et al., *J. Med. Chem.* 1990, 33, 1984-92; $A^{11}$=Br, Cl: L. B. Townsend et al., *J. Med. Chem.* 1988, 31, 2086-2092). Preferably, $A^{11}$=Br and I.

Both $R^3$ and $Q^1$ in the compounds described herein in some instances contain functional groups that can be further manipulated. It would be appreciated by those skilled in the art that such manipulation of functional groups could be accomplished with key intermediates or with late stage compounds. Such functional group transformations are exemplified in the following Schemes 24-25 as well as in the experimental section but are in no way meant to limit the scope of such transformations.

The compounds of Formula I-ACA' (=compounds of Formula I-ACA where $R^3$=Z—$CONR^{312}R^{322}$) were prepared from compounds of Formula XV' (=compounds of Formula XV where $R^3$=Z—$CO_2A^3$) as shown below in Scheme 24:

Scheme 24

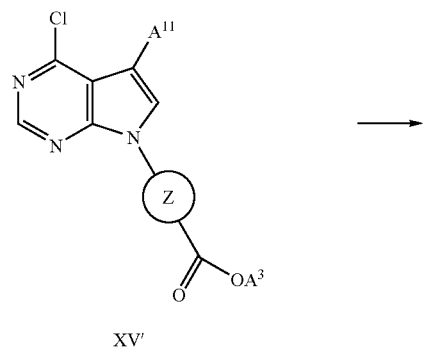

XV' where $R^{312}$ and $R^{322}$ are as defined previously for compound of Formula I; $A^{11}$=halogen such as Cl, Br, or I; and $A^3$=hydrogen or alkyl such as methyl or ethyl.

In a typical preparation of compound of Formula I-ACA', when $A^3$=alkyl and $R^{312}$ and $R^{322}$ were both equal to H, reaction of compound of Formula XV' with ammonia in a suitable solvent, afforded compound of Formula I-ACA'. Suitable solvents for use in the above process included, but were not limited to, ethers such as tetrahydrofuran (THF), glyme, and the like; dimethylformamide (DMF); dimethyl sulfoxide (DMSO); acetonitrile; alcohols such as methanol, ethanol, isopropanol, trifluoroethanol, and the like; and chlorinated solvents such as methylene chloride ($CH_2Cl_2$) or chloroform ($CHCl_3$). If desired, mixtures of these solvents were used, however, the preferred solvent was isopropanol. The above process was carried out at temperatures between about −78° C. and about 120° C. Preferably, the reaction was carried out between 80° C. and about 100° C. The above process to produce compounds of the present invention was preferably carried out in a glass pressure tube or a stainless steel reactor. Preferably, an excess of ammonia was used. Additionally, in a typical preparation of compound of Formula I-ACA' (compounds of Formula I-ACA where $R^3$=Z—$CONR^{312}R^{322}$), compound of Formula XV' (compounds of Formula XV' where $R^3$=Z—$CO_2A^3$) was reacted with $HNR^{312}R^{322}$ followed by ammonia in a suitable solvent. When $A^3$=H, typical coupling procedures (such as conversion of —$CO_2H$ to —COCl via treatment with $SOCl_2$ or oxalyl chloride followed by reaction with $HNR^{312}R^{322}$ or treatment of —$CO_2H$ and $HNR^{312}R^{322}$ with EDC or DCC in conjunction with DMAP, HOBT, or HOAt and the like) were employed to afford the transformation of a carboxylic acid to an amide. When $A^3$=alkyl such as methyl or ethyl, treatment of the ester with $Al(NR^{312}R^{322})$ afforded conversion of —$CO_2A^3$ to —$CO(NR^{312}H^{322})$. Subsequent treatment with ammonia afforded compounds of Formula I-ACA'.

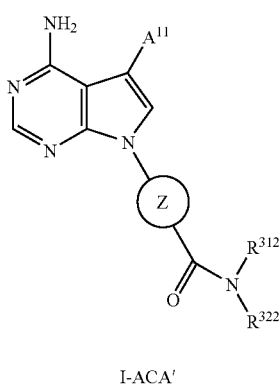

I-ACA'

The chemistry shown in Scheme 24 can also be applied to compounds with $Q^1$ in place of $A^{11}$.

The compounds of Formula XVIII (compounds of Formula XV, I-ACA, or I-AC where $R^3$=Z—$CH_2OH$), XIX (compounds of Formula XV, I-ACA, or I-AC where $R^3$=Z—$CH_2LG$), and XX (compounds of Formula XV, I-ACA, or I-AC where $R^3$=Z—$CH_2A^5(R^{313})(R^{323})_{aa}$) were prepared as shown below in Scheme 25:

Scheme 25

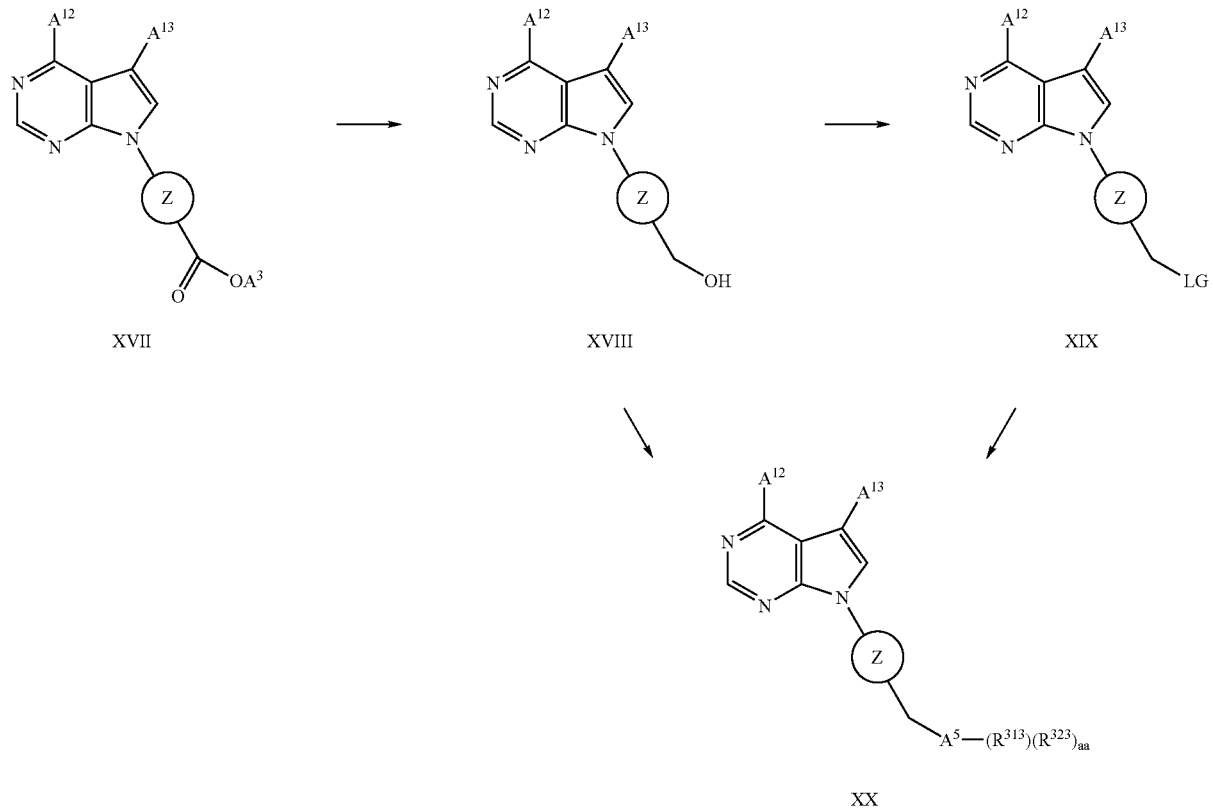

where $Q^1$, $R^{313}$, and $R^{323}$ are as defined previously for compound of Formula I; LG=suitable leaving group such as tosylate, mesylate, trifluoromethanesulfonate, or halo such as chloro, bromo, or iodo; aa=0 or 1; $A^3$=hydrogen or alkyl such as methyl or ethyl; $A^{11}$=halogen such as Cl, Br, or I; $A^{12}$=Cl or $NH_2$; $A^{13}$=$A^{11}$ or $Q^1$; and $A^5$=N, O or S.

The following table indicates the relations between the compounds of Formulas XVII-XX, $A^{12}$, $A^{13}$, compounds of Formulas I-AC, I-ACA, and XV, and $R^3$.

| Compound of Formula... | wherein $A^{12}$ = | and $A^{13}$ = | ...is equal to Formula... | wherein $R^3$ = |
|---|---|---|---|---|
| XVII | Cl | $A^{11}$ | XV | $Z-CO_2A^3$ |
| XVII | $NH_2$ | $A^{11}$ | I-ACA | $Z-CO_2A^3$ |
| XVII | $NH_2$ | $Q^1$ | I-AC | $Z-CO_2A^3$ |
| XVIII | Cl | $A^{11}$ | XV | $Z-CH_2OH$ |
| XVIII | $NH_2$ | $A^{11}$ | I-ACA | $Z-CH_2OH$ |
| XVIII | $NH_2$ | $Q^1$ | I-AC | $Z-CH_2OH$ |
| XIX | Cl | $A^{11}$ | XV | $Z-CH_2LG$ |
| XIX | $NH_2$ | $A^{11}$ | I-ACA | $Z-CH_2LG$ |
| XIX | $NH_2$ | $Q^1$ | I-AC | $Z-CH_2LG$ |
| XX | Cl | $A^{11}$ | XV | $Z-CH_2A^5R^2(R^4)_d$ |
| XX | $NH_2$ | $A^{11}$ | I-ACA | $Z-CH_2A^5R^2(R^4)_d$ |
| XX | $NH_2$ | $Q^1$ | I-AC | $Z-CH_2A^5R^2(R^4)_d$ |

In a typical preparation of compound of Formula XVIII (compounds of Formula XV, I-ACA, or I-AC, where $R^3$=Z—$CH_2OH$), compound of Formula XVII (compounds of Formula XV, I-ACA, or I-AC, where $R^3$=Z—$CO_2A^3$) is treated with a suitable reducing agent, such as lithium aluminum hydride or diisobutylaluminum hydride, in a suitable solvent, such as THF or methylene chloride, to afford compound of Formula XVIII. In a typical preparation of compound of Formula XX (compounds of Formula XV, I-ACA, or I-AC, where $R^3$=Z—$CH_2A^5(R^{313})(R^{323})_{aa}$), the hydroxy group of compound of Formula XVIII was converted to a suitable leaving group, LG, such as Cl or tosylate, mesylate, or triflate, by reaction with $SOCl_2$ or $Ts_2O$, $Ms_2O$, or $Tf_2O$ to afford compound of Formula XIX (compounds of Formula XV, I-ACA, or I-AC, where $R^3$=Z—$CH_2LG$). Reaction of compound of Formula XIX with $HA^5(R^{313})(R^{323})_{aa}$ afforded compound of Formula XX. Furthermore, compound of Formula XVIII can be directly converted to compound of Formula XX by treating compound of Formula XVIII with various alkylating agents or under typical Mitsunobu reaction conditions to afford compounds of Formula XX (compounds of Formula XV, I-ACA, or I-AC, where $R^3$=Z—$CH_2A^5(R^{313})(R^{323})_{aa}$) in which $A^5$=O, aa=0, and $R^{313}$=alkyl or aryl). Someone skilled in the art will choose the most appropriate stage during the sequence shown in Scheme 25 to convert $A^{12}$=Cl to $A^{12}$=$NH_2$ as described in Scheme 21, and to convert $A^{13}$=$A^{11}$ to $A^{13}$=$Q^1$ as described in Scheme 20, if applicable.

An alternative preparation of compounds of Formula I-AC is shown in Scheme 26.

Scheme 26

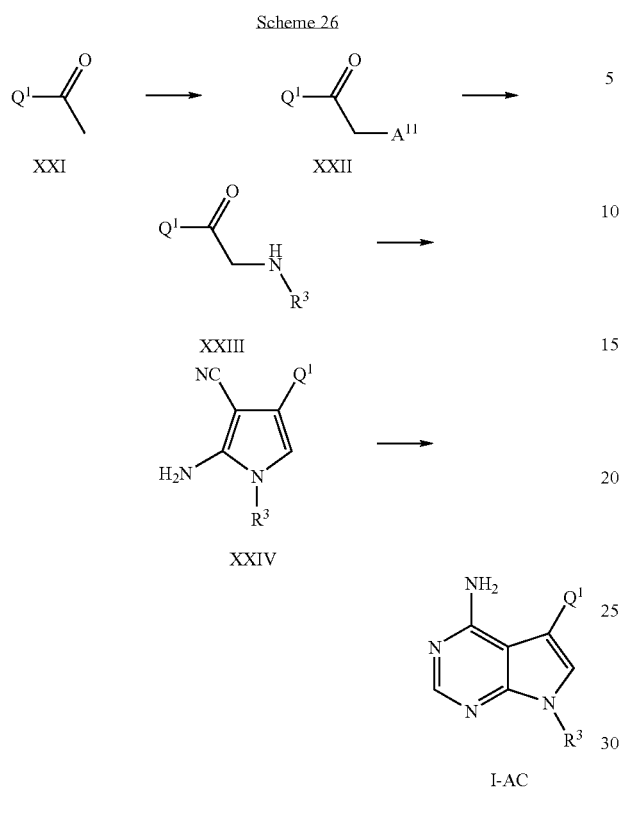

where $Q^1$ and $R^3$ are as defined previously for compound of Formula I; and $A^{11}$=halogen such as Cl, Br, or I.

The compounds of Formula XXI may be prepared from aldehydes $Q^1$-CHO (see Scheme 14 for their preparation) by addition of methyllithium or a methyl Grignard reagent, followed by oxidation of the resulting alcohol to the ketone of Formula XXI. Other compounds are commercially available or can be prepared by methods well known to someone skilled in the art, see: Larock, R. C. *Comprehensive Organic Transformations*, $2^{nd}$ ed.; Wiley and Sons: New York, 1999, 1197ff. Reaction of compounds of Formula XXI under typical halogenation conditions with typical halogenating agents including, but not limited to, $Br_2$, NBS, pyridinium perbromide, or $CuBr_2$ (for $A^{11}$=Br), or NCS or $SO_2Cl_2$ (for $A^{11}$=Cl) gives the compounds of Formula XXII. Their reaction with amines of Formula $H_2N$—$R^3$ gives the aminoketones of Formula XXIII that are converted to aminocyanopyrroles of Formula XXIV by reaction with malononitrile under basic conditions. Finally, reaction of compounds of Formula XXIV under typical cyclization conditions gives the compounds of Formula I-AC. Conditions for this cyclization include, but are not limited to, heating with formamide; heating with formamide and ammonia; sequential treatment with a trialkyl orthoformate, ammonia, and a base; sequential treatment with formamidine and ammonia.

It would be appreciated by those skilled in the art that in some situations, a substituent that is identical or has the same reactivity to a functional group which has been modified in one of the above processes, will have to undergo protection followed by deprotection to afford the desired product and avoid undesired side reactions. Alternatively, another of the processes described within this invention may be employed in order to avoid competing functional groups. Examples of suitable protecting groups and methods for their addition and removal may be found in the following reference: "Protective Groups in Organic Syntheses", T. W. Greene and P. G. M. Wuts, John Wiley and Sons, 1989.

Compound of Formula I-AQ is equal to compound of Formula I wherein $X_1$=CH; $X_2$, $X_3$ and $X_5$=N; $X_4$, $X_6$, and $X_7$=C and J=H or $NH_2$

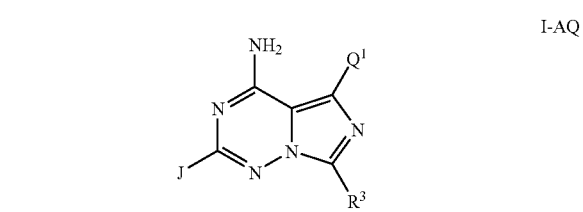

Method AQ was used when preparing compounds of Formula I-AQ as shown below in Scheme 27:

Method AQ:

Scheme 27

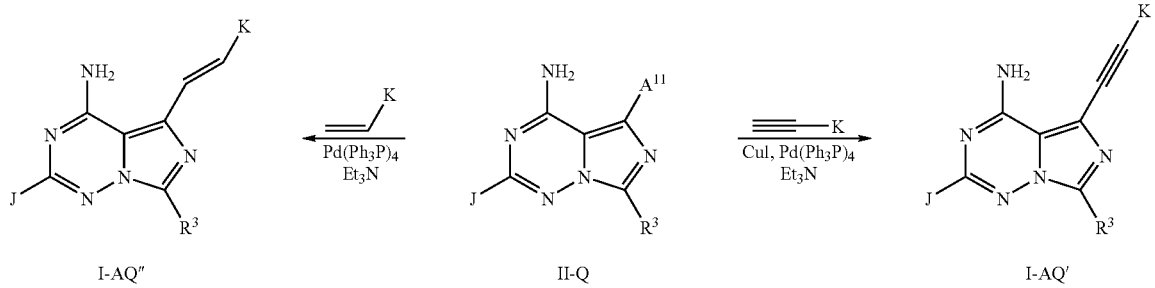

where $Q^1$, K and $R^3$ are as defined previously for compound of Formula I, $A^{11}$=halogen such as Cl, Br, or I and J=H or $NH_2$.

In a typical preparation of compounds of Formula I-AQ', a compound of Formula II-Q may be reacted with a suitable substituted acetylene derivative in a suitable solvent via typical Sonogashirai coupling procedures. Suitable solvents for use in the above process include, but are not limited to, ethers such as tetrahydrofuran (THF), glyme, dioxane, dimethoxyethane, and the like; dimethylformamide (DMF); dimethyl sulfoxide (DMSO); acetonitrile; and chlorinated solvents such as methylene chloride ($CH_2Cl_2$) or chloroform ($CHCl_3$). If desired, mixtures of these solvents may be used, however, the preferred solvent is DMF. The above process may be carried out at temperatures between about −78° C. and about 120° C. Preferably, the reaction is carried out between 0° C. and about 50° C. The above process to produce compounds of the present invention may be preferably carried out at about atmospheric pressure although higher or lower pressures can be used if desired. Substantially equimolar amounts of reactants are preferably used although higher or lower amounts can be used if desired. Alternatively, compounds of Formula I-AQ" may be prepared from a compound of Formula II-Q by reaction with suitable substituted vinyl derivatives in a suitable solvent via typical Heck coupling procedures. Suitable solvents for use in the above process include, but are not limited to, ethers such as tetrahydrofuran (THF), glyme, dioxane, dimethoxyethane, and the like; dimethylformamide (DMF); dimethyl sulfoxide (DMSO); acetonitrile; and chlorinated solvents such as methylene chloride ($CH_2Cl_2$) or chloroform ($CHCl_3$). If desired, mixtures of these solvents may be used, however, the preferred solvent is DMF. The above process can be carried out at temperatures between about −78° C. and about 120° C. Preferably, the reaction is carried out between 20° C. and about 100° C.

The compounds of Formula II-Q of Scheme 27 were prepared as shown below in Scheme 28.

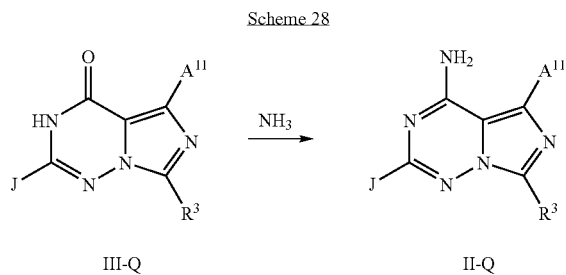

where $R^3$ is as defined previously for compound of Formula I and $A^{11}$=halogen such as Cl, Br, or I; and J=H or $NH_2$.

In a typical preparation of compounds of Formula II-Q, compound of Formula III-Q was reacted with phosphorus oxychloride ($POCl_3$) and triazole, and pyridine followed by ammonia ($NH_3$) in a suitable solvent. Suitable solvents for use in the above process included, but were not limited to, ethers such as tetrahydrofuran (THF), glyme, and the like; dimethylformamide (DMF); dimethyl sulfoxide (DMSO); acetonitrile; alcohols such as methanol, ethanol, isopropanol, trifluoroethanol, and the like; and chlorinated solvents such as methylene chloride ($CH_2Cl_2$) or chloroform ($CHCl_3$). If desired, mixtures of these solvents were used, however, the preferred solvent was isopropanol. The above process was carried out at temperatures between about −20° C. and about 50° C. Preferably, the reaction was carried out between 0° C. and about 25° C. The above process to produce compounds of the present invention was preferably carried out at about atmospheric pressure although higher or lower pressures were used if desired. Substantially equimolar amounts of reactants were preferably used although higher or lower amounts were used if desired.

The compounds of Formula III-Q of Scheme 28 were prepared as shown below in Scheme 29.

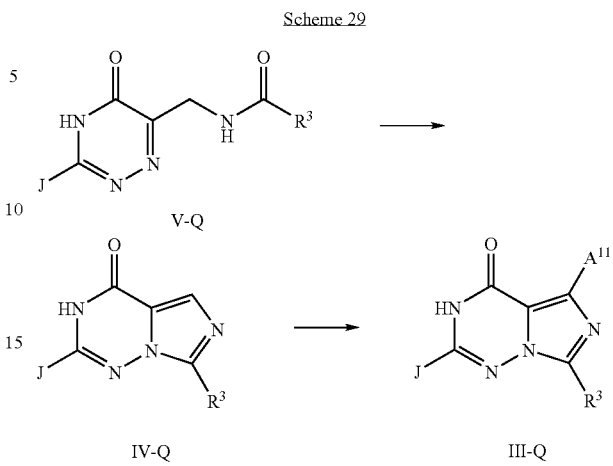

where $R^3$ is as defined previously for compound of Formula I; $A^{11}$=halogen such as Cl, Br, or I; and J=H or $NH_2$.

In a typical preparation of a compound of Formula III-Q, intermediate V-Q was converted to compound of Formula IV-Q. Intermediate of Formula V-Q was treated with phosphorus oxychloride ($POCl_3$) in a suitable solvent at a suitable reaction temperature. Suitable solvents for use in the above process included, but were not limited to, ethers such as tetrahydrofuran (THF), glyme, and the like, chlorinated solvents such as methylene chloride ($CH_2Cl_2$) or chloroform ($CHCl_3$), and acetonitrile. If desired, mixtures of these solvents were used. The preferred solvent was acetonitrile. The above process was carried out at temperatures between about −78° C. and about 120° C. Preferably, the reaction was carried out between 40° C. and about 95° C. The above process to produce compounds of the present invention was preferably carried out at about atmospheric pressure although higher or lower pressures were used if desired. Intermediate for Formula III-Q was prepared by reacting intermediate of Formula IV-Q with a suitable halogenating agent. Suitable halogenating agents included, but were not limited to, $Br_2$, $I_2$, $Cl_2$, N-chlorosuccinimide, N-bromosuccinimide, or N-iodosuccinimide. The preferred halogenating agent was N-iodosuccinimide. Suitable solvents for use in the above process included, but were not limited to, ethers such as tetrahydrofuran (THF), glyme, and the like; dimethylformamide (DMF); dimethyl sulfoxide (DMSO); acetonitrile; alcohols such as methanol, ethanol, isopropanol, trifluoroethanol, and the like; and chlorinated solvents such as methylene chloride ($CH_2Cl_2$) or chloroform ($CHCl_3$). If desired, mixtures of these solvents were used, however, the preferred solvent was DMF. The above process was carried out at temperatures between about −78° C. and about 120° C. Preferably, the reaction was carried out between 40° C. and about 75° C. The above process to produce compounds of the present invention was preferably carried out at about atmospheric pressure although higher or lower pressures were used if desired. Substantially equimolar amounts of reactants were preferably used although higher or lower amounts were used if desired.

Compounds of Formulae IV-Q and III-Q where J=$NH_2$ can be respectively converted into the compounds of Formulae IV-Q and III-Q where J=H, by diazotisation procedures known to those skilled in the art. A typical procedure includes the treatment of a compound of Formula IV-Q or III-Q where J=$NH_2$ with tert-butylnitrite in a suitable solvent such a THF or DMF.

The compounds of Formula V-Q of Scheme 29 were prepared as shown below in Scheme 30:

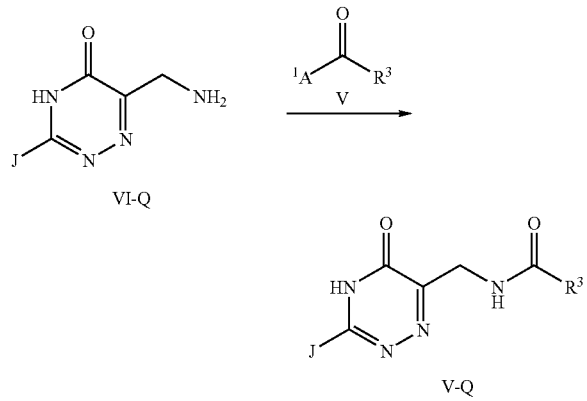

where $R^1$ is as defined previously for compound of Formula I; $A^1$=OH, alkoxy, or a leaving group such as chloro, imidazole or O-succinimide; and J=H or $NH_2$.

In a typical preparation, of a compound of Formula V-Q, a compound of Formula VI-Q and compound of Formula V were reacted under suitable amide coupling conditions. Suitable conditions include but are not limited to treating compounds of Formula VI-Q and V (when $A^1$=OH) with coupling reagents such as DCC or EDC in conjunction with DMAP, HOBt, HOAt and the like, or reagents like EEDQ. Suitable solvents for use in the above process included, but were not limited to, ethers such as tetrahydrofuran (THF), glyme, and the like; dimethylformamide (DMF); dimethyl sulfoxide (DMSO); acetonitrile; halogenated solvents such as chloroform or methylene chloride. If desired, mixtures of these solvents were used, however the preferred solvent was methylene chloride. The above process was carried out at temperatures between about 0° C. and about 80° C. Preferably, the reaction was carried out at about 22° C. The above process to produce compounds of the present invention was preferably carried out at about atmospheric pressure although higher or lower pressures were used if desired. Substantially equimolar amounts of reactants were preferably used although higher or lower amounts were used if desired. Alternatively, compounds of Formula VI-Q and V (where $A^1$=F, Cl, Br, I) were reacted with bases such as triethylamine or diisopropylethylamine and the like in conjunction with DMAP and the like. Suitable solvents for use in this process included, but were not limited to, ethers such as tetrahydrofuran (THF), glyme, and the like; dimethylformamide (DMF); dimethyl sulfoxide (DMSO); acetonitrile; pyridine; halogenated solvents such as chloroform or methylene chloride. If desired, mixtures of these solvents were used, however the preferred solvent was DMF. The above process was carried out at temperatures between about −20° C. and about 40° C. Preferably, the reaction was carried out between 0° C. and 25° C. The above process to produce compounds of the present invention was preferably carried out at about atmospheric pressure although higher or lower pressures were used if desired. Substantially equimolar amounts of compounds of Formula VI-Q and V (where $A^1$=F, Cl, Br, I) and base and substochiometric amounts of DMAP were preferably used although higher or lower amounts were used if desired. Additionally, other suitable reaction conditions for the conversion of an amine (compound of Formula VI-Q) to an amide (compound of Formula V-Q) can be found in Larock, R. C. *Comprehensive Organic Transformations*, 2$^{nd}$ ed.; Wiley and Sons: New York, 1999, pp 1941-1949.

The compounds of Formula VI-Q of Scheme 30 where J=H were prepared as shown below in Scheme 31:

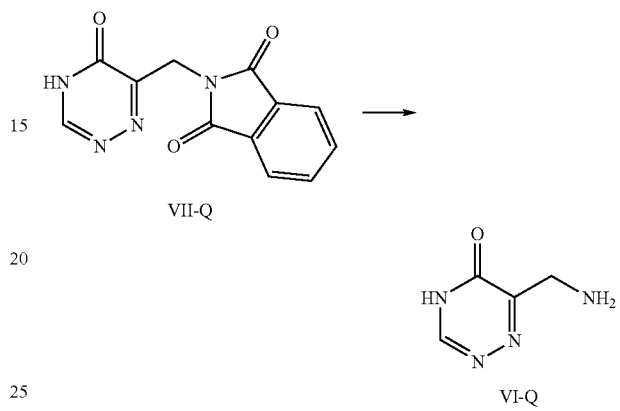

In a typical preparation, of a compound of Formula VI-Q, a compound of Formula VII-Q is reacted under suitable reaction conditions in a suitable solvent. Suitable conditions include treatment of compound of Formula VII-Q with hydrazine or methyl hydrazine in a suitable solvent. Suitable solvents for use in the above process included, but were not limited to, ethers such as tetrahydrofuran (THF), glyme, and the like; dimethylformamide (DMF); dimethyl sulfoxide (DMSO); acetonitrile; halogenated solvents such as chloroform or methylene chloride; alcoholic solvents such as methanol and ethanol. If desired, mixtures of these solvents may be used, however the preferred solvents were ethanol and methylene chloride. The above process was carried out at temperatures between about 0° C. and about 80° C. Preferably, the reaction was carried out at about 22° C. The above process to produce compounds of the present invention was preferably carried out at about atmospheric pressure although higher or lower pressures were used if desired. Substantially equimolar amounts of reactants were preferably used although higher or lower amounts were used if desired.

Compounds of Formula VI-Q where J=$NH_2$ may be prepared according to the procedures described in *J. Het. Chem.*, (1984), 21, 697.

The compounds of Formula VII-Q of Scheme 31 were prepared as shown below in Scheme 32:

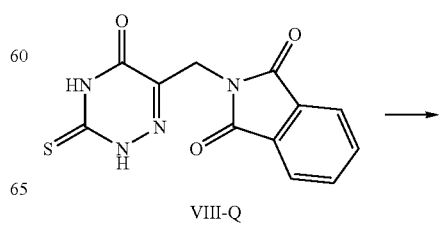

-continued

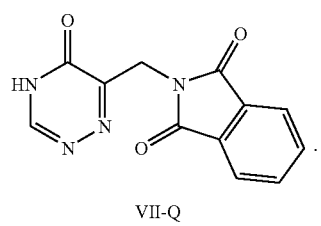

VII-Q

In a typical preparation of a compound of Formula VII-Q, a compound of Formula VIII-Q was reacted with Raney Nickel in a suitable solvent. Suitable solvents for use in the above process included, but were not limited to, ethers such as tetrahydrofuran (THF), glyme, and the like; dimethylformamide (DMF); dimethyl sulfoxide (DMSO); acetonitrile ($CH_3CN$); alcohols such as methanol, ethanol, isopropanol, trifluoroethanol, and the like; chlorinated solvents such as methylene chloride ($CH_2Cl_2$) or chloroform ($CHCl_3$). If desired, mixtures of these solvents were used, however, the preferred solvent was ethanol. The above process may be carried out at temperatures between about rt and about 100° C. Preferably, the reaction was carried out at about 80° C. The above process to produce compounds of the present invention was preferably carried out at about atmospheric pressure although higher or lower pressures were used if desired. Substantially equimolar amounts of reactants were preferably used although higher or lower amounts were used if desired. Additionally a compound of Formula VII-Q can be prepared by reacting a compound of Formula VIII-Q with a suitable oxidizing agent in a suitable solvent. A suitable oxidizing agent includes, but is not limited to hydrogen peroxide ($H_2O_2$), 3-chloro peroxybenzoic acid (mCPBA) and the like. Suitable solvents for use in the above process included, but were not limited to, ethers such as THF, glyme, and the like; DMF; DMSO; $CH_3CN$; and dimethylacetamide (DMA); chlorinated solvents such as $CH_2Cl_2$ or $CHCl_3$ If desired, mixtures of these solvents were used, however, the preferred solvent was DMA. The above process may be carried out at temperatures between about 0° C. and 100° C. Preferably, the reaction was carried out at about rt to 70° C. The above process to produce compounds of the present invention was preferably carried out at about atmospheric pressure although higher or lower pressures were used if desired. Substantially equimolar amounts of reactants were preferably used although higher or lower amounts were used if desired.

The compounds of Formula VIII-Q of Scheme 32 were prepared as shown below in Scheme 33:

Scheme 33

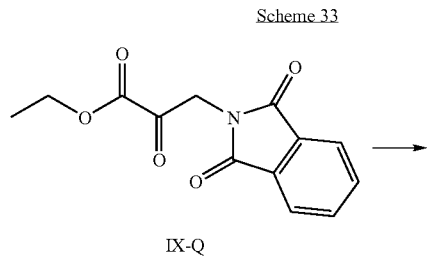

IX-Q

-continued

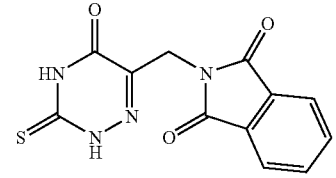

VIII-Q

In a typical preparation of a compound of Formula VIII-Q, a compound of Formula IX-Q was reacted with thiosemicarbazide and a suitable base in a suitable solvent. Suitable bases include, but were not limited to triethylamine, diisopropylethylamine and the like. Suitable solvents for use in the above process included, but were not limited to, ethers such as tetrahydrofuran (THF), glyme, and the like; dimethylformamide (DMF); dimethylacetamide (DMA); dimethyl sulfoxide (DMSO); acetonitrile ($CH_3CN$); alcohols such as methanol, ethanol, isopropanol, trifluoroethanol, and the like; chlorinated solvents such as methylene chloride ($CH_2Cl_2$) or chloroform ($CHCl_3$). If desired, mixtures of these solvents were used, however, the preferred solvent was ethanol. The above process may be carried out at temperatures between about rt and about 100° C. Preferably, the reaction was carried out between about 40° C. and 80° C. The above process to produce compounds of the present invention was preferably carried out at about atmospheric pressure although higher or lower pressures were used if desired. Substantially equimolar amounts of reactants were preferably used although higher or lower amounts were used if desired. Compound of Formula IX-Q can be prepared according to literature procedures Knutsen, Lars J. S. et. al., *J. Chem. Soc. Perkin Trans* 1: *Organic and Bio-Organic Chemistry* (1972-1999), 1984, 229-238.

It would be appreciated by those skilled in the art that in some situations, a substituent that is identical or has the same reactivity to a functional group which has been modified in one of the above processes, will have to undergo protection followed by deprotection to afford the desired product and avoid undesired side reactions. Alternatively, another of the processes described within this invention may be employed in order to avoid competing functional groups. Examples of suitable protecting groups and methods for their addition and removal may be found in the following reference: "Protective Groups in Organic Syntheses", T. W. Greene and P. G. M. Wuts, John Wiley and Sons, 1989.

Method AW was also used when preparing compounds of Formula II-Q as shown below in Scheme 34:

Method AW:

Scheme 34

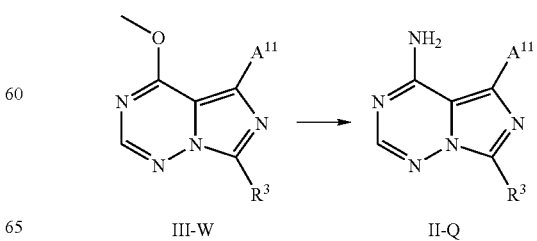

III-W     II-Q where $Q^1$ and $R^3$ are as defined previously for compound of Formula I, and $A^{11}$=halogen such as Cl, Br, or I.

In a typical preparation of compounds of Formula II-Q, compound of Formula III-W was reacted with ammonia in a suitable solvent. Suitable solvents for use in the above process included, but were not limited to, ethers such as tetrahydrofuran (THF), glyme, and the like; alcohols such as methanol, ethanol, isopropanol, trifluoroethanol, and the like; and chlorinated solvents such as methylene chloride ($CH_2Cl_2$) or chloroform ($CHCl_3$). If desired, mixtures of these solvents were used, however, the preferred solvent was isopropanol. The above process was carried out at temperatures between about 0° C. and about 50° C. Preferably, the reaction was carried out at between 0° C. and about 22° C. The above process to produce compounds of the present invention was preferably carried out at about atmospheric pressure although higher or lower pressures were used if desired. Substantially equimolar amounts of reactants were preferably used although higher or lower amounts were used if desired.

The compounds of Formula III-W of Scheme 34 were prepared as shown below in Scheme 35.

Scheme 35

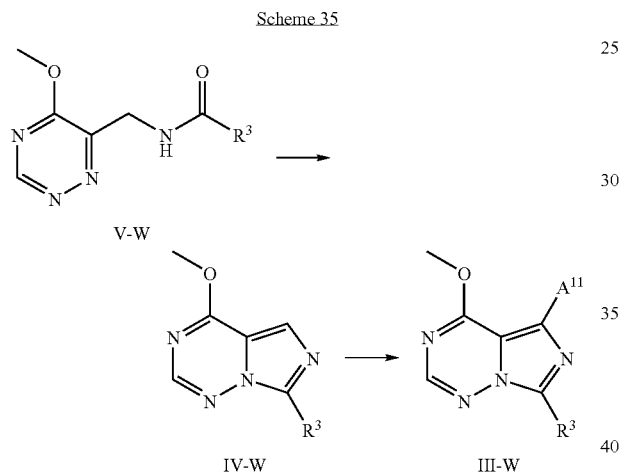

where $R^3$ is as defined previously for compound of Formula I and $A^{11}$=halogen such as Cl, Br, or I.

In a typical preparation of a compound of Formula III-W, compound V—W was converted to compound of Formula IV-W. Compound of Formula V-W was treated with phosphorus oxychloride ($POCl_3$) or the isolated "Vilsmeir salt" [CAS #33842-02-3] in a suitable solvent at a suitable reaction temperature. Suitable solvents for use in the above process included, but were not limited to, ethers such as tetrahydrofuran (THF), glyme, and the like, chlorinated solvents such as methylene chloride ($CH_2Cl_2$) or chloroform ($CHCl_3$), and acetonitrile ($CH_3CN$). If desired, mixtures of these solvents were used. The preferred solvent was acetonitrile. The above process was carried out at temperatures between about −78° C. and about 120° C. Preferably, the reaction was carried out between 40° C. and about 95° C. The above process to produce compounds of the present invention was preferably carried out at about atmospheric pressure although higher or lower pressures were used if desired. Compounds of Formula III-W were prepared by reacting compound of Formula IV-W with a suitable halogenating agent. Suitable halogenating agents included, but were not limited to, $Br_2$, $I_2$, $Cl_{12}$, N-chlorosuccinimide, N-bromosuccinimide, or N-iodosuccinimide. The preferred halogenating agent was N-iodosuccinimide.

Suitable solvents for use in the above process included, but were not limited to, ethers such as tetrahydrofuran (THF), glyme, and the like; dimethylformamide (DMF); dimethyl sulfoxide (DMSO); acetonitrile; alcohols such as methanol, ethanol, isopropanol, trifluoroethanol, and the like; and chlorinated solvents such as methylene chloride ($CH_2Cl_2$) or chloroform ($CHCl_3$). If desired, mixtures of these solvents were used, however, the preferred solvent was DMF. The above process was carried out at temperatures between about −78° C. and about 120° C. Preferably, the reaction was carried out between 40° C. and about 75° C. The above process to produce compounds of the present invention was preferably carried out at about atmospheric pressure although higher or lower pressures were used if desired. Substantially equimolar amounts of reactants were preferably used although higher or lower amounts were used if desired.

The compounds of Formula V-W of Scheme 35 were prepared as shown below in Scheme 36.

Scheme 36

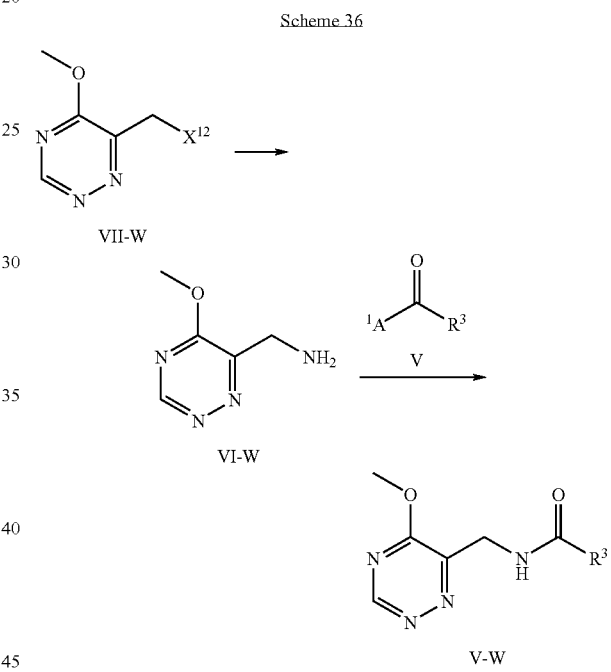

where $R^3$ is as defined previously for compound of Formula I, $X^{12}$=azido, or mono- or di-protected amino and $A^1$=OH, alkoxy or a leaving group such as chloro or imidazole.

In a typical preparation of a compound of Formula V-W, compound VI-W was reacted with compound V under suitable amide coupling conditions. Suitable conditions include but are not limited to those described for the conversion of compound XIII to compound XII as shown in Scheme 10. Compounds of Formula VI-W were prepared from compounds of Formula VII-W. A typical procedure for the conversion of compounds of Formula VII-W to compounds of Formula VI-W involves subjecting a compound of Formula VII-W, where $X^{12}$=azido, to reducing conditions such as, but not limited to, catalytic hydrogenation in a suitable solvent at a suitable reaction temperature. Suitable solvents for use in the above process included, but were not limited to, ethers such as tetrahydrofuran (THF), glyme, and the like, alcoholic solvents such as methanol, ethanol and the like, esters such as ethyl acetate, methyl acetate and the like. If desired, mixtures of these solvents were used. The preferred solvents were ethyl acetate and methanol. The above process was carried out at temperatures between about −78° C. and about 120° C. Preferably, the reaction was carried out between 40° C. and about 95° C. The above process to produce compounds of the present invention was preferably carried out at about atmospheric pressure although higher or lower pressures were used if desired. Alternatively, when $X^{12}$=azido, the reduction to compounds of Formula VI-W could be achieved by treatment of a compound of Formula VII-W with triaryl- or trialkylphosphines in the presence of water in a suitable solvent at a suitable reaction temperature. Suitable solvents for use in the above process included, but were not limited to, ethers such as tetrahydrofuran (THF), dioxane and the like, alcoholic solvents such as methanol, ethanol and the like, esters such as ethyl acetate, methyl acetate and the like, DMF, acetonitrile, and pyridine. If desired, mixtures of these solvents were used. The preferred solvents were THF and acetonitrile. The above process was carried out at temperatures between about −78° C. and about 120° C. Preferably, the reaction was carried out between 40° C. and about 95° C. The above process to produce compounds of the present invention was preferably carried out at about atmospheric pressure although higher or lower pressures were used if desired.

Where $X^{12}$=mono- or di-protected amino, the deprotection could be effected by the procedures known to those skilled in the art and as disclosed in: "Protective Groups in Organic Syntheses", T. W. Greene and P. G. M. Wuts, John Wiley and Sons, 1989.

The compounds of Formula VII-W of Scheme 36 were prepared as shown below in Scheme 37:

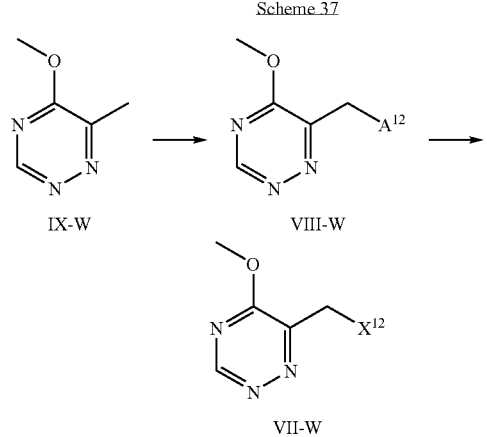

where $R_3$ is as defined previously for compound of Formula I, $X^{12}$ is as defined for a compound of Formula VII-W and $A^{12}$=iodo, bromo, chloro, tosylate, mesylate or other leaving group.

In a typical preparation of a compound of Formula VII-W where $X^{12}$=azide, compound VIII-W was reacted with an azide salt, such as lithium or sodium azide in suitable solvent at a suitable reaction temperature. Suitable solvents for use in the above process included, but were not limited to, alcoholic solvents such as ethanol, butanol and the like, esters such as ethyl acetate, methyl acetate and the like, DMF, acetonitrile, acetone DMSO. If desired, mixtures of these solvents were used. The preferred solvents were acetone and DMF. The above process was carried out at temperatures between about −78° C. and about 120° C. Preferably, the reaction was carried out between 40° C. and about 95° C. The above process to produce compounds of the present invention was preferably carried out at about atmospheric pressure although higher or lower pressures were used if desired. Alternatively, where $X^{12}$=mono- or di-protected amino, compounds of Formula VIII-W were reacted with suitably protected amines where the protecting group is chosen such that the nucleophilic nature of the nitrogen is either retained or where it can be enhanced by the action of a reagent such as a base. Those skilled in the art will recognize that such protecting groups include, but are not limited to, benzyl, trityl, allyl, and alkyloxycarbonyl derivatives such as BOC, CBZ and FMOC.

Compounds of Formula VIII-W where $A^{12}$=halogen, are prepared from compounds of Formula XI-W. In a typical procedure, compounds of Formula XI-W are treated with halogenating reagents such as but not limited to N-iodosuccinimide, N-bromosuccinimide, N-chlorosuccinimide, cyanuric chloride, N,N'-1,3-dibromo-5,5-dimethylhydantoin, bromine and iodine, preferably in the presence of one or more radical sources such as dibenzoyl peroxide, azobisisobutyronitrile or light in suitable solvent at a suitable reaction temperature. Suitable solvents for use in the above process included, but were not limited to, chlorinated solvents such as carbon tetrachloride, dichloromethane, α,α,α-trifluorotoluene and the like, esters such as methyl formate, methyl acetate and the like, DMF, acetonitrile. If desired, mixtures of these solvents were used. The preferred solvents were carbon tetrachloride and α,α,α-trifluorotoluene. The above process was carried out at temperatures between about −78° C. and about 120° C. Preferably, the reaction was carried out between 40° C. and about 95° C. The above process to produce compounds of the present invention was preferably carried out at about atmospheric pressure although higher or lower pressures were used if desired.

Those skilled in the art will appreciate that compounds of Formula IX-W can be made by routes disclosed in the literature, for example as in *Bulletin de la Societe Chimique de France*, (1973), (6)(Pt. 2), 2126.

Compounds of Formula I-AQ and/or their precursors may be subjected to various functional group interconversions as a means to access some functionalities that may not be introduced directly as a result of incompatible chemistries. Examples of such functional group manipulations applicable to compounds of Formula I-AQ and their precursors are similar, but not limited to, those described in the previous schemes that relate to compounds of Formula I-AA, I-R, I-AB, I-AC and I-AQ.

Experimental Procedures

8-Chloro-3-cyclobutyl-imidazo[1,5-a]pyrazine

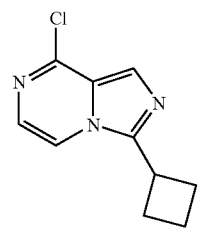

This compound was prepared using procedures analogous to that described for trans-methyl 4-(8-chloroimidazo[1,5-a]pyrazin-3-yl)cyclohexanecarboxylate and its precursor trans-methyl 4-({[(3-chloropyrazin-2-yl)methyl]amino}carbonyl)

cyclohexanecarboxylate, using cyclobutanecarboxylic acid in place of 4-(methoxycarbonyl)cyclohexanecarboxylic acid.

8-Chloro-3-cyclobutyl-1-iodoimidazo[1,5-a]pyrazine

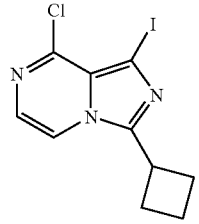

8-Chloro-3-cyclobutylimidazo[1,5-a]pyrazine (1058 mg, 5.1 mmol) and NIS (1146 mg, 5.1 mmol) in anh DMF (10 mL) were stirred at 60° C. under Ar for 6 h. The reaction was diluted with DCM (~400 mL), washed (H$_2$O, brine), dried (Na$_2$SO$_4$) and concentrated under reduced pressure. Purification of the crude material by flash chromatography on silica gel (50 g cartridge, 10:1-8:1-7:1-6:1 hexanes:EtOAc) afforded the title compound as a pale yellow solid; $^1$H NMR (400 MHz, CDCl$_3$) δ 7.51 (d, J=4.8 Hz, 1H), 7.26 (d, J=4.8 Hz, 1H), 3.75 (quintetd, J=1.2 Hz, 8.4 Hz, 1H), 2.62-2.42 (m, 4H), 2.32-1.98 (m, 2H); MS (ES+): m/z 334.0 (100) [MH$^+$]; HPLC: t$_R$=3.38 min (OpenLynx, polar_5 min).

3-Cyclobutyl-1-iodoimidazo[1,5-a]pyrazin-8-amine

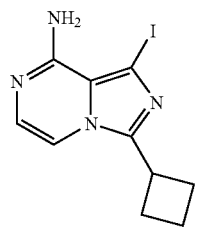

A Parr bomb containing 8-chloro-3-cyclobutyl-1-iodoimidazo[1,5-a]pyrazine (759 mg, 2.3 mmol) in IPA (100 mL) was saturated with NH$_3$(g) for 5 min at 0° C. then sealed and heated at 115° C. for 38 h. The reaction mixture was then concentrated under reduced pressure, partitioned between DCM (200 mL) and H$_2$O (50 mL) and extracted with DCM (50 mL). Combined organic fractions were washed with brine, dried (Na$_2$SO$_4$) and concentrated under reduced pressure to provide the title compound as a white solid; $^1$H NMR (400 MHz, CDCl$_3$) δ 7.13 (d, J=4.8 Hz, 1H), 7.01 (d, J=5.2 Hz, 1H), 5.63 (br, 2H), 3.73 (quintetd, J=0.8 Hz, 8.4 Hz, 1H), 2.60-2.38 (m, 4H), 2.20-1.90 (m, 2H); MS (ES+): m/z 315.9 (100) [MH$^+$]; HPLC: t$_R$=1.75 min (OpenLynx, polar_5 min).

trans-Methyl 4-(8-chloroimidazo[1,5-a]pyrazin-3-yl)cyclohexanecarboxylate

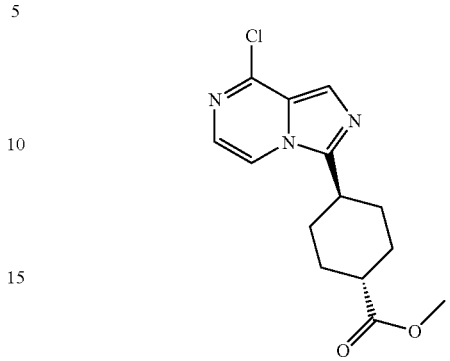

trans-Methyl 4-({[(3-chloropyrazin-2-yl)methyl]amino}carbonyl)-cyclohexanecarboxylate (29.00 g, 93.02 mmol) was dissolved in anhydrous acetonitrile (930 mL) and anhydrous DMF (9 mL) and heated at 55° C. under nitrogen for 3 h. The reaction mixture was concentrated in vacuo, then, the solid residue was taken up in DCM, then, basified to pH 10 with 2M ammonia in isopropanol. The mixture was concentrated in vacuo, re-dissolved in DCM, and then loaded onto TEA-basified silica gel. The crude product was purified by a silica gel column chromatography (eluted with 2:3 EtOAc/DCM) to obtain the title compound as a yellow powder; $^1$H NMR (CDCl$_3$, 400 MHz) δ 1.63 (ddd, J=13.2, 13.2, 13.2, 3.2 Hz, 2H), 1.85 (ddd, J=13.2, 13.2, 13.2, 2.8 Hz, 2H), 2.10 (dd, J=14.4, 3.2 Hz, 2H), 2.19 (dd, J=14.0, 3.2 Hz, 2H), 2.46 (tt, J=12.4, 3.6 Hz, 1H), 2.96 (tt, J=11.6, 3.2 Hz, 1H), 3.70 (s, 3H), 7.33 (dd, J=5.2, 1.2 Hz, 1H), 7.61 (d, J=4.8 Hz, 1H), 7.79 (s, 1H). MS (ES+): m/z 294.17/296.14 (100/86) [MH$^+$]. HPLC: t$_R$=2.85 min (OpenLynx, polar_5 min).

trans-Methyl 4-({[(3-chloropyrazin-2-yl)methyl]amino}carbonyl)cyclohexanecarboxylate

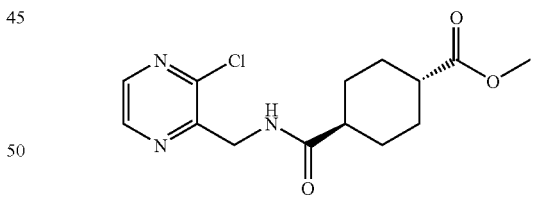

A THF (370 mL) solution of 4-(methoxycarbonyl)cyclohexanecarboxylic acid (15.14 g, 81.30 mmol) and CDI (13.18 g, 81.30 mmol) was placed under a nitrogen atmosphere and stirred at 60° C. for 4 h. The reaction mixture was cooled to rt, then, (3-chloropyrazin-2-yl)methylamine bis-hydrochloride salt (16.00 g, 73.91 mmol) and DIPEA (31.52 g, 244.00 mmol, 42.5 mL) was added. After stirring at 60° C. for 20 h, the reaction was concentrated in vacuo. The crude reaction mixture was purified by a silica gel glass column chromatography (eluted with 3:2 DCM/EtOAc) to obtain the pure desired product as a slightly yellowish creamy white powder; $^1$H NMR (CDCl$_3$, 400 MHz) δ 1.43-1.65 (m, 4H), 2.01-2.14 (m, 4H), 2.25 (tt, J=12.0, 3.6 Hz, 1H), 2.34 (tt, J=11.6, 3.2 Hz, 1H), 3.68 (s, 3H), 4.70 (d, J=4.4 Hz, 2H), 6.81 (s, br, —NH), 8.32-8.36 (m, 1H), 8.46 (d, J=2.4 Hz, 1H); MS (ES+): m/z 312.17/314.12 (84/32) [MH⁺]; HPLC: $t_R$=2.44 min (OpenLynx, polar_5 min).

C-(3-Chloropyrazin-2-yl)methylamine bis-hydrochloride

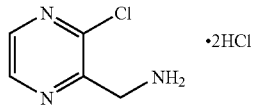

A solution of 2-(3-chloropyrazin-2-ylmethyl)-isoindole-1,3-dione (10.0 g, 36.5 mmol) in anhydrous CH₂Cl₂ (200 mL) was charged with hydrazine (2.87 mL, 2.93 g, 91.3 mmol, 2.5 eq.) at rt, under N₂ atmosphere. After 2.5 h, MeOH (300 mL) was added and the reaction was heated until the solution was homogenous. The reaction mixture was allowed to stir for 19 h. The white ppt that had formed (2,3-dihydrophthalazine-1,4-dione byproduct), was filtered off and washed several times with ether. The clear filtrate was concentrated in vacuo and the concentrate was dissolved in EtOAc and filtered again to remove white ppt. All solvent was removed, giving a yellow oil, which was dissolved into EtOAc and ether and charged with HCl (g). The title compound, a pale yellow solid, instantly precipitated. The title compound was dried in a 40° C. oven for 72 h, affording the title compound, as a dark yellow solid; ¹H NMR (400 MHz, CD₃OD) δ 4.55 (2 H, s), 8.27 (1 H, d, J=2.52 Hz), 8.54 (1 H, d, J=2.56 Hz); MS (ES+): m/z 143.96/145.96 (100/60) [MH⁺]; HPLC: $t_R$=0.41 min (OpenLynx, polar_7 min).

7-Cyclobutyl-5-iodoimidazo [5,1-f][1,2,4]triazin-4-ylanmine

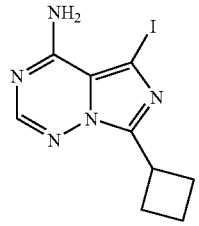

To a solution of 1,2,4-triazole (1.28 g, 18.59 mmol) in anhydrous pyridine (10 mL) was added phosphorus oxychloride (POCl₃) (0.578 mL, 6.20 mmol) and stirred at rt for 15 min. This mixture was dropwise charged (3.5 min) with a solution of 7-cyclobutyl-5-iodo-3H imidazo[5,1f][1,2,4]triazin-4-one (0.653 mg, 2.07 mmol) in anhydrous pyridine (14 mL) and stirred for 1.5 h. The reaction mixture was cooled to 0° C. quenched with 2M NH₃ in isopropanol (IPA) until basic then allowed to reach rt and stirred for an additional 2 h. The reaction mixture was filtered through a fritted Buchner funnel and washed with DCM. The filtrate was concentrated in vacuo and purified by chromatography on silica gel [eluting with 30% EtOAc in DCM] resulting in the title compound as an off-white solid; ¹H NMR (CDCl₃, 400 MHz) δ 1.93-2.04 (m, 1H), 2.05-2.18 (m, 1H), 2.35-2.45 (m, 2H), 2.49-2.62 (m, 2H), 4.00-4.12 (m, 1H), 7.82 (s, 1H); MS (ES+): m/z 316.08 (100) [MH⁺], HPLC: $t_R$=2.59 min (MicromassZQ, polar_5 min).

7-Cyclobutyl-5-iodo-3H-imidazo[5,1-f[]1,2,4]triazin-4-one

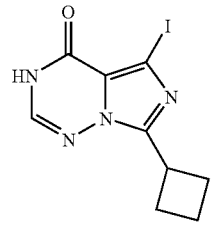

A solution of 7-cyclobutyl-3H-imidazo[5,1-f][1,2,4]triazin-4-one (789 mg, 4.15 mmol) and N-iodosuccinimide (NIS, 933 mg, 4.15 mmol) in anhydrous DMF (40 mL) was stirred overnight at rt. An additional 4 eq. of NIS was added and reaction was heated to 55° C. for 6 h. The reaction mixture was concentrated in vacuo and partitioned between DCM and H₂O and separated. The aqueous layer was washed with DCM (3×) and the combined organic fractions were washed with 1M sodium thiosulfate (Na₂S₂O₃) (1×), brine (1×), dried over sodium sulfate (Na₂SO₄), filtered, and concentrated in vacuo. The solid was triturated with 20% EtOAc in DCM and filtered through a fritted Buchner funnel resulting in the title compound as an off-white solid; ¹H NMR (DMSO-d₆, 400 MHz) δ 1.84-1.96 (m, 1H), 1.98-2.13 (m, 1H), 2.25-2.43 (m, 4H), 3.84-3.96 (m, 1H), 7.87 (s, 1H); MS (ES+): m/z 317.02 (100) [MH⁺], HPLC: $t_R$=2.62 min (MicromassZQ, polar_5 min).

7-Cyclobutyl-3H-imidazo[5,1-f][1,2,4]triazin-4-one

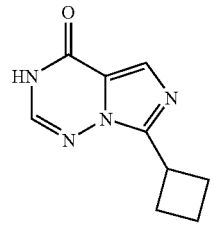

A crude solution of cyclobutanecarboxylic acid (5-oxo-4,5-dihydro-[1,2,4]triazin-6-ylmethyl)amide (1.33 g, 6.39 mmol) in phosphorus oxychloride (POCl₃) (10 mL) was heated to 55° C. The reaction was heated for 2 h then concentrated in vacuo and the crude oil was cooled to 0° C. in an ice-bath and quenched with 2M NH₃ in ispropanol (IPA) until slightly basic. This crude reaction mixture was concentrated in vacuo and was partitioned between DCM and H₂O and separated. The aqueous layer was extracted with DCM (3×) and the combined organic fractions were dried over sodium sulfate (Na₂SO₄), filtered and concentrated in vacuo. The crude material was purified by chromatography on silica gel [eluting with 5% MeOH in DCM], resulting in the title compound as an off-white solid; ¹H NMR (DMSO-d₆, 400 MHz) δ 1.86-1.96 (m, 1H), 2.00-2.13 (m, 1H); 2.26-2.46 (m, 4H); 3.87-4.00 (m, 1H); 7.71 (s, 1H); 7.87 (d, J=3.6 Hz, 1H); 11.7

(brs, 1H); MS (ES+): m/z 191.27 (100) [MH+], HPLC: $t_R$=2.06 min (MicromassZQ, polar_5 min).

Cyclobutanecarboxylic acid (5-oxo-4,5-dihydro-[1,2,4]triazin-6-ylmethyl)amide

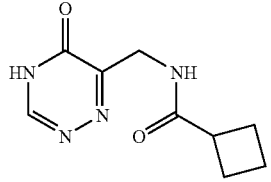

To a solution of 6-aminomethyl-4H-[1,2,4]triazin-5-one (500 mg, 3.96 mmol) and N,N-diisopropylethylamine (DIEA) (0.829 mL, 4.76 mmol) in anhydrous N,N-dimethylforamide (DMF) (20 mL) and anhydrous pyridine (2 mL) was dropwise charged with cyclobutanecarbonyl chloride (0.451 mL, 3.96 mmol) at 0° C. then warmed to rt and stirred for an additional 1.5 h. The reaction mixture was quenched with H$_2$O (2 mL) and concentrated in vacuo and was purified by chromatography on silica gel [eluting with 5% MeOH in DCM (200 mL)→10% MeOH in DCM (800 mL)], affording the title compound; $^1$H NMR (DMSO-d$_6$, 400 MHz) δ 1.7-1.82 (m, 1H), 1.70-1.92 (m, 1H); 1.97-2.07 (m, 2H); 2.07-2.19 (m, 2H); 3.55-3.67 (m, 1H); 4.19 (d, 2H); 7.97 (brt, J=5.6 Hz, 1H); 8.67 (s, 1H); MS (ES+): m/z 209.25 (100) [MH+], HPLC: $t_R$=1.56 min (MicromassZQ, polar_5 min).

6-Aminomethyl-4H-[1,2,4]triazin-5-one

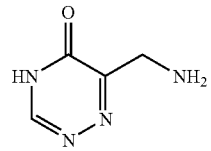

A slurry of 2-(5-oxo-4,5-dihydro-[1,2,4]triazin-6-ylmethyl)isoindole-1,3-dione (4 g, 15.6 mmol) in DCM/EtOH (1:1) (150 mL) was charged with anhydrous hydrazine (1.23 mL, 39.0 mmol) and stirred at rt for 18 h. The reaction mixture was concentrated in vacuo and the off-white solid was triturated with warm CHCl$_3$ and filtered through a fritted funnel. The solid was then triturated with hot boiling methanol (MeOH) and filtered through a fritted funnel resulting in an off-white solid. The material was triturated a second time as before and dried overnight resulting in the title compound as a white solid, which was taken on to the next step without further purification; $^1$H NMR (DMSO-d$_6$, 400 MHz) δ 3.88 (s, 2H), 8.31 (2, 1H); MS (ES+): m/z 127.07 (100) [MH+], HPLC: $t_R$=0.34 min (MicromassZQ, polar_5 min).

2-(5-Oxo-4,5-dihydro-[1,2,4]triazin-6-ylmethyl) isoindole-1,3-dione

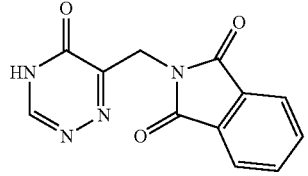

A slurry of 2-(5-oxo-3-thioxo-2,3,4,5-tetrahydro-[1,2,4]triazin-6-ylmethyl)isoindole-1,3-dione (1.0 g, 3.47 mmol) in EtOH (40 mL) was charged with excess Raney Ni (3 spatula) and heated to reflux for 2 h. The reaction mixture was filtered hot through a small pad of celite and washed with a hot mixture of EtOH/THF (1:1) (100 mL) and the filtrate was concentrated in vacuo resulting in the title compound as an off-white solid; $^1$H NMR (DMSO-d$_6$, 400 MHz) δ 4.75 (s, 2H), 7.84-7.98 (m, 4H), 8.66 (s, 1H); MS (ES+): m/z 257.22 (100) [MH+], HPLC: $t_R$=2.08 min (MicromassZQ, polar_5 min).

2-(5-Oxo-3-thioxo-2,3,4,5-tetrahydro-[1,2,4]triazin-6-ylmethyl)indan-1,3-dione

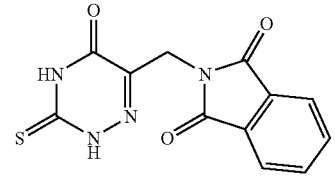

A slurry of 3-(1,3-dioxo-1,3-dihydroisoindol-2-yl)-2-oxopropionic acid ethyl ester (20 g, 76.6 mmol) in anhydrous EtOH (300 mL) was charged with thiosemicarbazide (6.98 g, 76.6 mmol) in one portion and heated to 80° C. for 2 h. The reaction mixture was charged with N,N-diisopropylethylamine (DIEA) (26.7 mL, 76.56 mmol) and heated to 40° C. for 6 h then stirred at rt for an additional 10 h. The reaction mixture was concentrated in vacuo and solid was triturated with hot EtOH/EtOAc filtered and washed with EtOAc. The solid was dried overnight in a vacuum oven (40° C.) resulting in the title compound as an off-white solid; $^1$H NMR (DMSO-d$_6$, 400 MHz) δ 4.68 (s, 2H), 7.85-7.95 (m, 4H); MS (ES+): m/z 289.2 (100) [MH+], HPLC: $t_R$=2.50 min (MicromassZQ, polar_5 min).

Benzyl 4-{[(3-chloropyrazin-2-yl)methyl] carbamoyl}piperidine-1-carboxylate

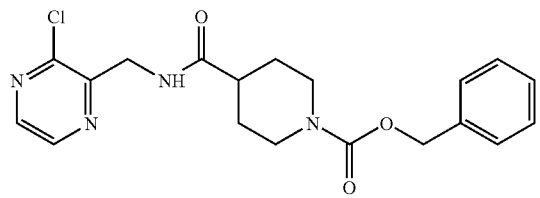

A solution of C-(3-Chloropyrazin-2-yl)methylamine bishydrochloride (2.00 g, 0.0107 mol) and N,N-diisopropylethylamine (2.2 g, 0.017 mol) in DCM (27.0 mL) was treated with and N-(3-dimethylaminopropyl)-N'-ethylcarbodiimide hydrochloride (3.2 g, 0.017 mol), 1-hydroxybenzotriazole (1.5 g, 0.011 mol) and 1-[(benzyloxy)carbonyl]-4-piperidine carboxylic acid (3.8 g, 0.014 mol). The mixture was stirred at rt overnight then diluted with DCM (30 mL), washed with sat. NaHCO$_3$ (20 mL) and brine (20 mL), then dried over Na$_2$SO$_4$ and concentrated in vacuo. The crude material thus obtained was chromatographed over silica gel eluting with EtOAc:hexane 1:1 yielding 3.38 g of the title compound. $^1$H NMR (400 MHz, CDCl$_3$): δ 1.68-1.78 (m, 2H), 1.91-1.94 (m, 2H), 2.44 (m, 1H), 2.89-2.92 (m, 2H), 4.24-4.26 (m, 2H), 4.70 (d, J=4.8 Hz, 2H). 5.14 (s, 2H), 6.85 (br, 1H), 7.30-7.37 (m, 5H), 8.34 (d, J=2.8 Hz, 1H), 8.45 (d, J=2.8 Hz, 1H). MS (ES+): m/z 389.17 [MH+].

Benzyl 4-(8-chloroimidazo[1,5-a]pyrazin-3-yl)piperidine-1-carboxylate

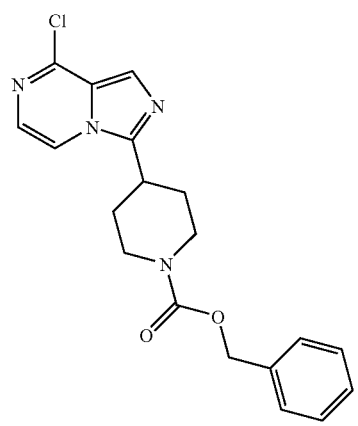

To a suspension of benzyl 4-{[(3-chloropyrazin-2-yl)methyl]carbamoyl}piperidine-1-carboxylate (0.100 g, 0.220 mmol) in EtOAc (0.9 mL) and DMF (0.068 mL) at 0° C. was slowly added POCl$_3$ (0.082 mL, 0.88 mmol). After stirring at rt for an hour the mixture was cooled to 0° C. then treated with solid NaHCO$_3$. The mixture was stirred for 20 min at rt, diluted with water and extracted with EtOAc (3×20 mL). The combined extracts were washed with water (2×30 mL) and brine (30 mL), then dried over Na$_2$SO$_4$, and concentrated in vacuo to yield 2.07 g of desired product.

$^1$H NMR (400 MHz, CDCl$_3$): δ 1.98-2.04 (m, 4H), 3.03-3.20 (m, 3H), 4.30-4.33 (m, 2H), 5.16 (s, 2H), 7.33 (d, J=5.2 Hz, 1H), 7.35-7.38 (m, 5H), 7.26 (d, J=4.4 Hz, 1H), 7.79 (s, 1H). MS (ES+): m/z 371.22 [MH+].

Benzyl 4-(8-chloro-1-iodoimidazo[1,5-a]pyrazin-3-yl)piperidine-1-carboxylate

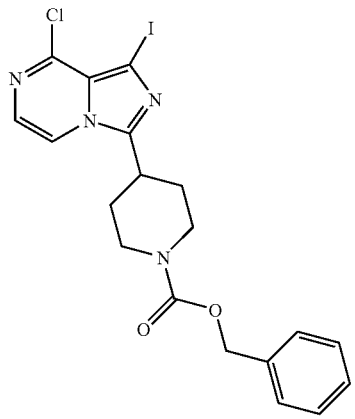

To a solution of benzyl 4-(8-chloroimidazo[1,5-a]pyrazin-3-yl)piperidine-1-carboxylate (1.31 g, 0.00354 mol) in DMF (0.6 mL) was added NIS (1.6 g, 0.0071 mol). The reaction mixture was left to stir at 55° C. for 20 h. then the mixture was diluted with EtOAc (20 mL), washed with water (2×40 mL) and brine, then dried over Na$_2$SO$_4$ and concentrated in vacuo. The crude reaction mixture was chromatographed over silica gel eluting with hexane→hexane:EtOAc 1:1 yielding 1.63 g of desired product. $^1$H NMR (400 MHz, CDCl$_3$): δ 1.95-2.04 (m, 4H), 3.02-3.15 (m, 3H), 4.29-4.32 (m, 2H), 5.15 (s, 2H), 7.32 (d, J=5.2 Hz, 1H), 7.34-7.37 (m, 5H), 7.66 (d, J=5.2 Hz, 1H), MS (ES+): m/z 497.03 [MH+].

Benzyl 4-(8-amino-1-iodoimidazo[1,5-a]pyrazin-3-yl)piperidine-1-carboxylate

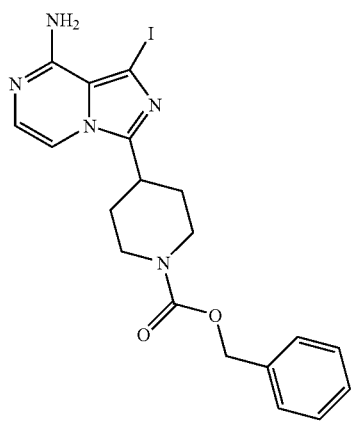

A mixture of benzyl 4-(8-chloro-1-iodoimidazo[1,5-a]pyrazin-3-yl)piperidine-1-carboxylate (0.500 g, 0.00101 mol) in IPA (20 mL) was cooled to at −78° C. and treated with a stream of ammonia gas over 3 minutes. The resulting solution was heated at 110° C. in a Parr vessel prior to concentration in vacuo, suspension in DCM and filtration through a bed of Celite. The filtrate was concentrated in vacuo to afford 0.504 g of desired product. $^1$H NMR (400 MHz, CDCl$_3$): δ 1.88-2.02 (m, 2H), 2.99-3.10 (m, 3H), 4.24-4.41 (m, 2H), 5.15 s, 2H), 6.03 (br, 2H), 7.03 (d, J=4.8 Hz, 1H), 7.24 (d, J=5.2 Hz, 1H), 7.31-7.40 (m, 5H). MS (ES+): m/z 479.33 [MH+].

EXAMPLE 1

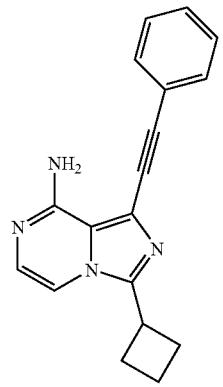

3-Cyclobutyl-1-(phenylethynyl)imidazo[1,5-a]pyrazin-8-amine

A solution of 3-cyclobutyl-1-iodoimidazo[1,5-a]pyrazin-8-amine (50 mg, 0.159 mmol) in N,N-dimethylformamide (6 mL) and evacuated and charged with $N_2$ three times, then treated with triethylamine (0.044 mL, 0.318 mmol), phenylacetylene (0.175 mL, 1.59 mmol), and copper (I) iodide (3.0 mg, 0.0159 mmol). The mixture re-evacuated and charged with $N_2$ twice more, then charged with tetrakis(triphenylphoshine)palladium (0) (20.2 mg, 0.0175 mmol) and evacuated and charged with $N_2$ a final two times. The reaction mixture was stirred at rt for 16 h, then concentrated in vacuo, dissolved in MeOH/CH$_3$CN (1:1)(4 mL) and was filtered through a 0.45 fritted μM autovial prior to purification via mass directed preparative HPLC that afforded 13 mg of the title compound. $^1$H NMR (DMSO-d$_6$, 400 MHz) δ 1.87-1.99 (m, 1H), 2.01-2.15 (m, 1H), 2.32-2.47 (m, 4H), 3.87-3.99 (m, 1H), 6.66 (brs, 2H), 7.08 (brs, 1H), 7.40-7.51 (m, 4H), 7.59-7.67 (m, 2H); MS (ES+): m/z 289.13 [MH$^+$].

EXAMPLE 2

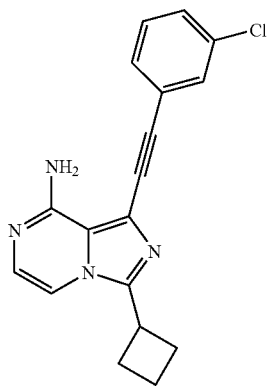

1-[(3-Chlorophenyl)ethynyl]-3-cyclobutylimidazo[1,5-a]pyrazin-8-amine

Prepared according to the procedure described for Example 1 using the appropriate acetylene derivative in place of phenylacetylene. MS (ES+): m/z 323.06 & 325.02 [MH$^+$].

EXAMPLE 3

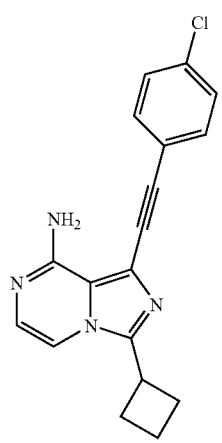

1-[(4-Chlorophenyl)ethynyl]-3-cyclobutylimidazo[1,5-a]pyrazin-8-amine

Prepared according to the procedure described for Example 1 using the appropriate acetylene derivative in place of phenylacetylene. MS (ES+): m/z 322.99 & 324.95 [MH$^+$].

EXAMPLE 4

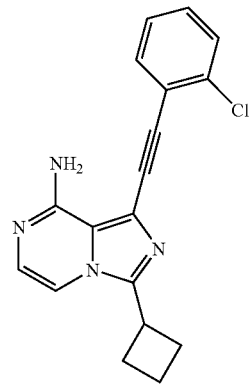

1-[(2-Chlorophenyl)ethynyl]-3-cyclobutylimidazo[1,5-a]pyrazin-8-amine

Prepared according to the procedure described for Example 1 using the appropriate acetylene derivative in place of phenylacetylene. MS (ES+): m/z 323.06 & 325.02 [MH$^+$].

EXAMPLE 5

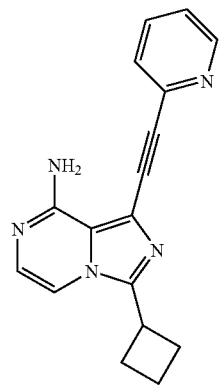

3-Cyclobutyl-1-(pyridin-2-ylethynyl)imidazo[1,5-a]pyrazin-8-amine

Prepared according to the procedure described for Example 1 using the appropriate acetylene derivative in place of phenylacetylene. MS (ES+): m/z 290.10 [MH$^+$].

EXAMPLE 6

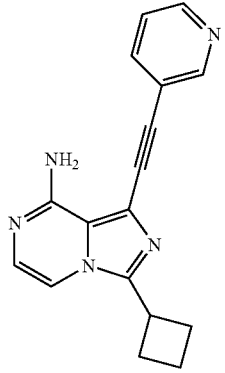

3-Cyclobutyl-1-(pyridin-3-ylethynyl)imidazo[1,5-a]pyrazin-8-amine

Prepared according to the procedure described for Example 1 using the appropriate acetylene derivative in place of phenylacetylene. MS (ES+): m/z 290.11 [MH$^+$].

EXAMPLE 7

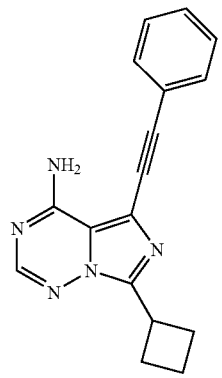

7-Cyclobutyl-5-(phenylethynyl)imidazo[5,1-f][1,2,4]triazin-4-amine

Prepared according to the procedure described for Example 1 using 7-cyclobutyl-5-iodoimidazo[5,1-f][1,2,4]triazin-4-ylamine in place of 3-cyclobutyl-1-iodoimidazo[1,5-a]pyrazine-8-amine. $^1$H NMR (DMSO-d$_6$, 400 MHz) δ 1.88-1.99 (m, 1H), 2.01-2.10 (m, 1H), 2.29-2.48 (m, 4H), 3.93-4.05 (m, 1H), 6.94 (brs, 1H), 7.43-7.48 (m, 3H), 7.66-7.73 (m, 2H), 7.92 (s, 1H), 8.55 (brs, 1H); MS (ES+): m/z 290.10 [MH$^+$].

EXAMPLE 8

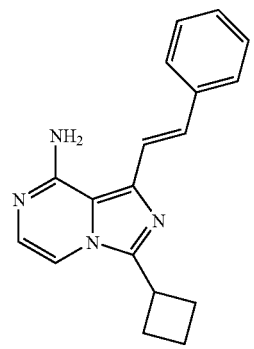

3-Cyclobutyl-1-[(E)-2-phenylvinyl]imidazo[1,5-a]pyrazin-8-amine

A solution of 3-cyclobutyl-1-iodoimidazo[1,5-a]pyrazin-8-amine (50 mg, 0.159 mmol), styrene (0.022 mL, 0.191 mmol) and triethylamine (0.044 mL, 0.318 mmol) in DMF (3.0 mL) was degassed three times, charged with tetrakis(triphenylphosphine)palladium (0) (18 mg, 0.0159 mmol) degassed twice more and then heated at 75° C. for 16 h. The reaction mixture was then concentrated in vacuo dissolved in MeOH/CH$_3$CN (1:1)(4 mL) and was filtered through a 0.45 μM fritted autovial prior to purification via mass directed preparative HPLC which afforded the title compound. $^1$H NMR (DMSO-d$_6$, 400 MHz) δ 1.87-1.99 (m, 1H), 2.02-2.17 (m, 1H), 2.37-2.47 (m, 4H), 3.18 (s, 2H), 3.83-3.94 (m, 1H), 6.94 (d, J=4.9 Hz, 1H), 7.25 (t, J=7.33 Hz, 1H), 7.32-7.40 (m, 3H), 7.45 (d, J=15.5 Hz, 1H), 7.63 (d, J=15.45 Hz, 1H), 7.73 (d, J=7.46 Hz, 2H); MS (ES+): m/z 291.15 [MH$^{30}$].

EXAMPLE 9

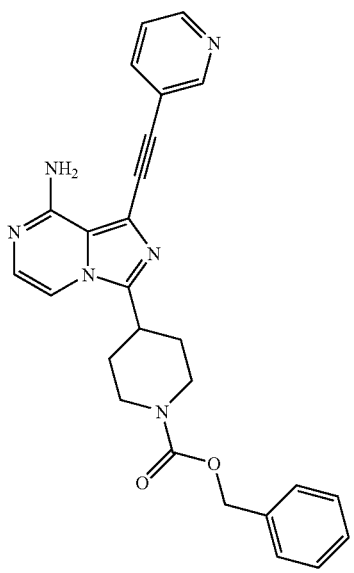

Benzyl 4-(8-amino-1-(pyridin-3-ylethynyl)imidazo[1,5-a]pyrazin-3-yl)piperidine-1-carboxylate To a solution of on benzyl 4-(8-amino-1-iodoimidazo[1,5-a]pyrazin-3-yl)piperidine-1-carboxylate (1.00 g, 0.00210 mol) in DMF (26 mL) was added triethylamine (0.58 mL, 0.0042 mol), 3-ethynylpyridine (1.1 g, 0.010 mol), and copper(I) iodide (66.6 mg, 0.350 mmol). The mixture was degassed three times, charged with tetrakis(triphenylphosphine)palladium(0) (360 mg, 0.00031 mol), degassed again three times and then stirred at rt for 16 h. The reaction mixture was passed through a pad of Celite and the filtrate concentrated in vacuo. The residue was reconstituted in DCM and purified by chromatography over silica get eluting with 20% $CH_3CN$ in DCM to afford the title compound. $^1$H NMR (400 MHz-DMSO-d6) δ 1.62-1.72 (m, 2H), 1.91-1.96 (m, 2H), 3.00-3.06 (m, 2H), 3.35-3.42 (m, 1H), 4.08-4.11 (m, 2H), 5.11 (s, 2H) 6.69 (bs, 2H), 7.12 (d, J=5.2 Hz, 1H), 7.30-7.33 (m, 1H), 7.38-7.40 (m, 4H), 7.46 (m, 1H), 7.74 (d, J=4.8 Hz, 1H), 8.03-8.06 (m, 1H), 8.58 (dd, J=1.6, 4.8, 1H) and 8.81-8.82 (m, 1H); MS (ES+): m/z: 452.91 [MH+].

EXAMPLE 10

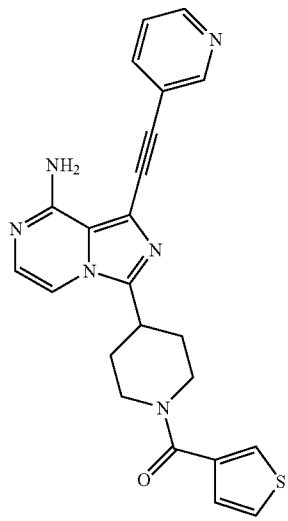

1-(Pyridin-3-ylethynyl)-3-[1-(3-thienylcarbonyl)piperidin-4-yl]imidazo[1,5-a]pyrazin-8-amine Concentrated HCl (10 mL, 10M, 0.3 mol) was added to benzyl 4-(8-amino-1-(pyridin-3-ylethynyl)imidazo[1,5-a]pyrazin-3-yl)piperidine-1-carboxylate (650 mg, 0.0014 mol) and the mixture was left to stir at rt overnight prior to dilution with with water (30 mL) and washing with diethyl ether (3×20 mL). The aqueous layer was concentrated in vacuo, to afford 3-piperidin-4-yl-1-(pyridin-3-ylethynyl)imidazo[1,5-a]pyrazin-8-amine hydrochloride (610 mg, 99%).

This material (100.00 mg, 0.23 mmol) in DMF (4 mL) was treated with thiophene-3-carboxylic acid (36 mg, 0.28 mmol), TBTU (90.1 mg, 0.28 mmol) and DIPEA (0.2 mL, 1 mmol). The mixture was left to stir at rt for 30 min then diluted with DCM (30 mL) and washed with water (3×20 mL). The organic extracts were combined, washed with brine, dried over anhydrous sodium sulfate and concentrated in vacuo. The residue was chromatographed over silica gel eluting with 5% MeOH in DCM to afford the title compound.

$^1$H NMR (400 MHz-DMSO-d6) δ 1.63-1.69 (m, 4H), 1.74-1.77 (m, 4H), 3.48-3.50 (m, 1H), 6.70 (bs, 12), 7.13 (d, J=5.2 Hz, 1H), 7.23 (dd, J=1.2, 4.8 Hz, 1H), 7.46-7.50 (m, 1H), 7.61-7.63 (m, 1H), 7.77 (d, J=5.2 Hz, 1H), 7.81-7.82 (m, 1H), 8.03-8.06 (m, 1H), 8.59 (dd, J=1.2, 4.8 Hz, 1H) and 8.81-8.82 (m, 1H); MS (ES+): m/z: 428.83 [MH+].

What is claimed is:

1. A compound represented by Formula (I)

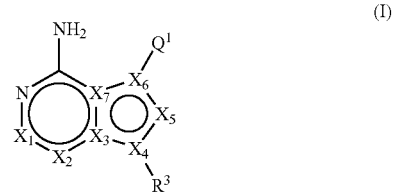

or a pharmaceutically acceptable salt thereof, wherein:

$X_1$ and $X_2$ are both CH;

$X_4$, $X_6$, and $X_7$ are all C;

$X_3$ and $X_5$ are both N;

$R^3$ is cyclo$C_{3-10}$alkyl or heterocyclyl, either of which is optionally substituted by —C(O)O(CH$_2$)$_{aa}$hetaryl, —C(O)(CH$_2$)$_{aa}$hetaryl, —C(O)O(CH$_2$)$_{aa}$aryl, —C(O)(CH$_2$)$_{aa}$aryl, or —C(O)OC$_{0-6}$alkyl;

$Q^1$ is —A—(K)$_m$

A is vinyl or acetylenyl

K is aryl or hetaryl, either optionally substituted by halogen;

m is 1;

aa is 0 or 1; and provided that the compound is not 3-cyclobutyl-1-[(4-phenoxyphenyl)ethynyl]imidazo[1,5-a]pyrazin-8-amine, 3-cyclobutyl-1-[(1-methyl-1H-imidazol-5-yl)ethynyl]imidazo[1,5-a]pyrazin-8-amine, N-{3-[(8-amino-3-cyclobutylimidazo[1,5-a]pyrazin-1-yl)ethynyl]phenyl}-4-chlorobenzamide or 3-cyclobutyl-1-(pyridin-4-ylethynyl)imidazo[1,5-a]pyrazin-8-amine.

2. The compound according to claim 1, selected from
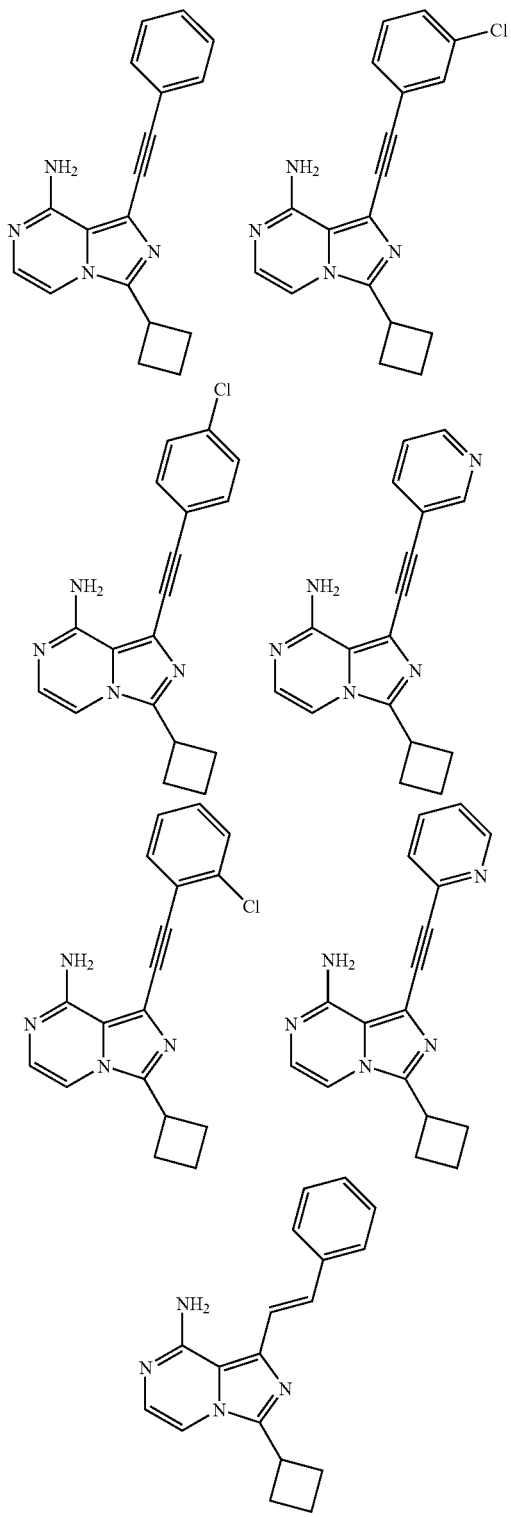
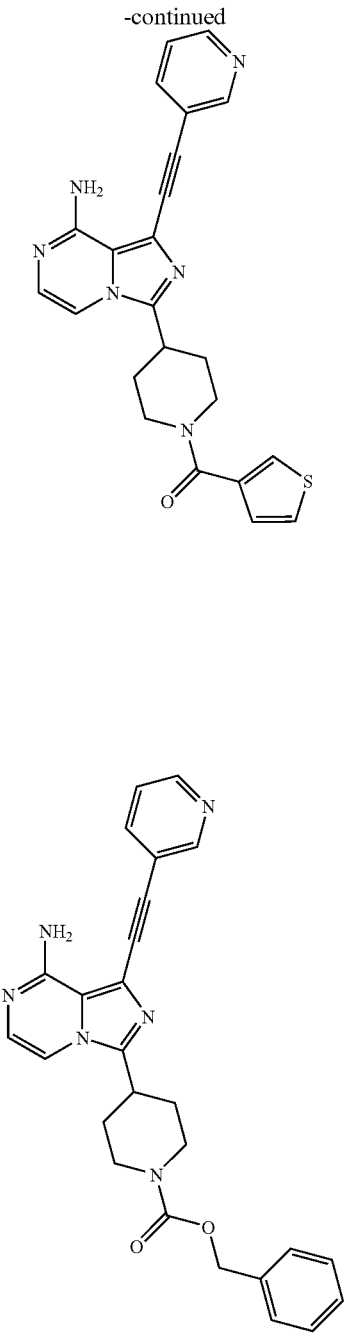
or a pharmaceutically acceptable salt thereof.
3. A pharmaceutical composition comprising a compound according to claim 1, or a pharmaceutically acceptable salt thereof, and a pharmaceutically acceptable carrier.
* * * * *

UNITED STATES PATENT AND TRADEMARK OFFICE
CERTIFICATE OF CORRECTION

| | | |
|---|---|---|
| PATENT NO. | : 7,659,274 B2 | Page 1 of 1 |
| APPLICATION NO. | : 11/657156 | |
| DATED | : February 9, 2010 | |
| INVENTOR(S) | : Crew et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 291 days.

Signed and Sealed this

Thirtieth Day of November, 2010

David J. Kappos
*Director of the United States Patent and Trademark Office*